United States Patent [12]
Baltimore et al.

(10) Patent No.: US 9,290,761 B2
(45) Date of Patent: *Mar. 22, 2016

(54) MICRORNA INHIBITION FOR THE TREATMENT OF INFLAMMATION AND MYELOPROLIFERATIVE DISORDERS

(71) Applicant: California Institute of Technology, Pasadena, CA (US)

(72) Inventors: David Baltimore, Pasadena, CA (US); Ryan M. O'Connell, Pasadena, CA (US); Konstantin Taganov, Pasadena, CA (US); Mark Boldin, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/138,472

(22) Filed: Dec. 23, 2013

(65) Prior Publication Data

US 2014/0220049 A1 Aug. 7, 2014

Related U.S. Application Data

(63) Continuation of application No. 12/122,595, filed on May 16, 2008, now Pat. No. 8,697,672.

(60) Provisional application No. 60/930,461, filed on May 16, 2007.

(51) Int. Cl.
| | |
|---|---|
| *A01N 43/04* | (2006.01) |
| *C12Q 1/68* | (2006.01) |
| *C12N 15/113* | (2010.01) |
| *A61K 31/56* | (2006.01) |
| *A61K 45/06* | (2006.01) |

(52) U.S. Cl.
CPC .............. *C12N 15/113* (2013.01); *A61K 31/56* (2013.01); *A61K 45/06* (2013.01); *C12N 2310/113* (2013.01); *C12N 2310/141* (2013.01)

(58) Field of Classification Search
None
See application file for complete search history.

(56) References Cited

U.S. PATENT DOCUMENTS

2009/0143326 A1 6/2009 Obad et al.

OTHER PUBLICATIONS

Abcam RAW cells [online]. [retrieved on Dec. 14, 2010]. Retrieved from the internet: http://www.abcam.com/RAW-264-7-Mouse-leukaemic-monocyte-macrophage-cell-line-Whole-Cell-Lysate-ab7187.html.
Costinean et al., "Pre-B cell proliferation and lymphoblastic leukemia/high-grade lymphoma in Eu-miR155 transgenic mice", PNAS, vol. 103, No. 18, pp. 7024-7029, 2006.
Doyle et al., "IRF3 Mediates a TLR3/TLR4-Specific Antiviral Gene Program." *Immmunity*. 17:251-263 (2002).
Eis et al., "Accumulation of miR-155 and *BIC* RNA in human B cell lymphomas." *Proc. Nat. Acad. Sci. USA*. 102(10):3627-3632 (2005).
Grimson et al., "MicroRNA Targeting Specificity in Mammals: Determinants beyond Seed Pairing." *Mol. Cell*. 27:91-105 (2007).
Kracht et al., "Transcriptional and Post-Transcriptional Control of Gene Expression in Inflammation." *Cytokine*. 20:91-106 (2002).
Lawrie, C.H., "MicroRNAs and Haematology: Small Molecules, Big Function", British Journal of Haematology, vol. 137, pp. 503-512, 2007.
Lawrie et al., "Detection of Elevated Levels of Tumour-Associated MicroRNAs in Serum of Patients with Diffuse Large B-Cell Lymphoma", British Journal of Haematology, vol. 141, pp. 672-675, 2008.
Lewis et al., "Prediction of Mammalian MicroRNA Targets." *Cell*. 115:787-798 (2003).
Lois et al., "Germline Transmission and Tissue-Specific Expression of Transgenes Delivered by Lentiviral Vectors." *Science* 295:868-872 (2002).
Meister et al., "Sequence-Specific Inhibition of MicroRNA and siRNA-Induced RNA Silencing", RNA, vol. 10, pp. 544-550, 2004.
Nogrady. "Medicinal Chemistry A Biochemical Approach." Oxford University Press, New York, pp. 388-392 (1985).
Taganov, et al. "NF-kB-dependent induction of microRNA miR-146, an inhibitor targeted to signaling proteins of innate immune responses." *Proc. Nat. Acad. Sci. USA*. 103:12481-12486 (2006).
Tong et al., "Modulation of Mirna-Activity in Human Cancer: A New Paradigm for Cancer Gene Therapy?", Cancer Gene Therapy, vol. 15, pp. 341-355, 2008.
Yang et al. "Long-term in vivo provision of antigen-specific T cell immunity by programming hematopoietic stem cells." *Proc. Nat. Acad. Sci. USA*. 102(12):4518-4523 (2005).

*Primary Examiner* — Jennifer Pitrak McDonald
(74) *Attorney, Agent, or Firm* — Knobbe Martens Olson & Bear LLP

(57) ABSTRACT

The present disclosure relates to the finding that microRNA-155 plays a role in inflammation, hematopoiesis and myeloproliferation, and that dysregulation of microRNA-155 expression is associated with particular myeloproliferative disorders. Disclosed herein are methods and compositions for diagnosing an treating disorders, including inflammation and myeloproliferation, modulating the levels of expression of one or more genes selected from the group consisting of Cutl1, Arntl, Picalm, Jarid2, PU.1, Csflr, HIF1α, Sla, Cepbβ, and Bach1, and the like.

20 Claims, 32 Drawing Sheets

MICRORNA INHIBITION FOR THE TREATMENT OF INFLAMMATION AND MYELOPROLIFERATIVE DISORDERS

CROSS-REFERENCE TO RELATED APPLICATIONS

The present application claims priority to U.S. Non-provisional application Ser. No. 12/122,595, filed May 16, 2008, which claims the benefit of U.S. Provisional Application Ser. No. 60/930,461, filed on May 16, 2007, by Baltimore et al., and entitled "Inflammatory Cytokines and Pathogen Associated Molecular Patterns Induce Expression of the Mammalian Oncogene microRNA-155," the entire disclosure of which is herein incorporated by reference in its entirety.

STATEMENT REGARDING FEDERALLY SPONSORED R&D

The U.S. Government has certain rights in this invention pursuant to Grant No. R01 GM039458-16 awarded by National Institutes of Health.

REFERENCE TO SEQUENCE LISTING, TABLE, OR COMPUTER PROGRAM LISTING

The present application is being filed along with a Sequence Listing in electronic format. The Sequence Listing is provided as a file entitled Sequence_Listing-REGLS_001C1.TXT, created Dec. 20, 2013, which is 15.1 KB in size. The information in the electronic format of the Sequence Listing is incorporated herein by reference in its entirety.

BACKGROUND

1. Field of the Invention

Embodiments disclosed herein relate to molecular medicine, and in particular to compositions and methods that can be used for diagnosing and treating inflammation and myeloproliferative disorders, among other things.

2. Description of the Related Art

MicroRNAs (miRNAs) are a class of small noncoding RNAs that negatively regulate their mRNA targets by binding with imperfect complementarity in the 3'-untranslated region. Largely unrecognized before 2001, it is now clear that miRNA represent a widely conserved mechanism of post-transcriptional gene regulation. In mammals, regulatory roles have been identified for miRNA in many areas of biology, pointing to miRNA as an exciting new class of therapeutic targets with broad applications.

SUMMARY OF THE INVENTION

Provided herein are methods of detecting acute myeloid leukemia in a subject, comprising identifying a subject suspected of having acute myeloid leukemia, measuring the levels of microRNA-155 (miR-155) in the bone marrow of said subject, and identifying the subject as having acute myeloid leukemia (AML) if said levels of miR-155 are elevated compared to control levels. In certain embodiments, the control levels can be the miR-155 levels in the bone marrow of a subject that does not have AML or other myeloproliferative disorder. In certain embodiments, the control levels can be the average levels of miR-155 in a population of subjects that do not have AML or other myeloproliferative disorder. In certain embodiments, the control can be the average miR-155 level of a population of subjects that do not have AML or other myeloproliferative disorder. In certain embodiments, the AML is acute myelomonocytic leukemia. In certain embodiments, the AML is acute monocytic leukemia. In certain embodiments, the measuring step comprises performing quantitative PCR. In certain embodiments, the measuring step comprises performing a microarray analysis.

Provided herein are methods of treating or preventing an miR-155 associated condition, such as a myeloproliferative disorder or inflammation. Provided herein are methods of treating or preventing a myeloproliferative disorder, comprising identifying a subject having, or suspected of having a myeloproliferative disorder, and administering to said subject an miR-155 antagonist. In certain embodiments, the myeloproliferative disorder is acute myeloid leukemia. In certain embodiments, the acute myeloid leukemia is acute myelomonocytic leukemia. In certain embodiments, the acute myeloid leukemia is acute monocytic leukemia.

Also provided herein are methods of treating inflammation in a subject in need thereof, comprising identifying a subject in need of a reduction in inflammation and administering to said subject an miR-155 antagonist. In certain embodiments, the inflammation is mediated by a Toll-like receptor (TLR). In certain embodiments, the TLR may be TLR2, TLR3, TLR, 4 or TLR9.

Methods of modulating the expression of one or more miR-155 target genes related hematopoiesis and/or myeloproliferation are also provided herein. The gene may be Cutl1, Arntl, Picalm, Jarid2, PU.1, Csf1r, HIF1α, Sla, Cepbβ, or Bach1. The modulation may be achieved by contacting a target cell with a miR-155 antagonist. The target cell may be a hematopoietic stem cell, a bone marrow cell, a myeloid precursor cell, and a myeloid cell. The myeloid cell may be a monocyte, a macrophage, or a neutrophil. In certain embodiments, the modulation comprises increasing expression of one or more of the target genes.

Further provided herein are methods for modulating cell proliferation in a granulocyte/monocyte population comprising contacting the granulocyte/monocyte population with a miR-155 antagonist. In certain embodiments, cell proliferation is inhibited. In certain embodiments, the rate of cell proliferation is reduced, i.e. cell proliferation is slowed.

Also provided herein are methods for modulating proliferation of hematopoietic cells comprising contacting the hematopoietic cells with a miR-155 antagonist. In certain embodiments, cell proliferation is inhibited. In certain embodiments, the rate of cell proliferation is reduced, i.e., cell proliferation is slowed. In certain embodiments, the hematopoietic cell is a myeloid cell.

In certain embodiments, the miR-155 antagonist comprises an miR-155 antisense compound. In certain embodiments, the miR-155 antisense compound comprises a modified oligonucleotide consisting of 12 to 30 linked nucleosides, wherein the nucleobase sequence of the modified oligonucleotide is complementary to a sequence at least 80% identical to mature microRNA-155 (SEQ ID NO: 72), pre-microRNA-155 (SEQ ID NO: 73), or a microRNA-155 seed sequence (SEQ ID NOs: 43-56). In certain embodiments, the nucleobase sequence of the miR-155 oligonucleotide has no more than two mismatches to the nucleobase sequence of mature miR-155 (SEQ ID NO: 72), or pre-miR-155 (SEQ ID NO: 73). In certain embodiments, the modified oligonucleotide is conjugated to a ligand. In certain embodiments, at least one internucleoside linkage of the modified oligonucleotide is a modified internucleoside linkage. In certain embodiments, at least one nucleoside of the modified oligonucleotide comprises a modified sugar. In certain embodiments, each nucleoside of the modified oligonucleotide comprises a modified sugar. In certain embodiments, at least one nucleoside of the modified oligonucleotide comprises a modified nucleobase. In certain embodiments, each internucleoside linkage of the modified oligonucleotide comprises a modified internucleoside linkage. In certain embodiments, the internucleoside linkage is a phosphorothioate internucleoside linkage. In certain embodiments, the nucleobase sequence of the modified oligonucleotide comprises at least 15, 16, 17, 18, 19, 20, or 21 consecutive nucleobases of SEQ ID NO: 74. In certain embodiments, the nucleobase sequence of the modified oligonucleotide consists of the nucleobase sequence of SEQ ID NO: 74.

BRIEF DESCRIPTION OF THE DRAWINGS

FIG. 4A shows the distribution of wild-type murine macrophages expressing cell surface markers CD11b and CD86 following stimulation with culture medium. FIG. 4B shows the distribution of wild-type murine macrophages expressing cell surface markers CD11b and CD86 following stimulation with IFNβ. FIG. 4B shows the distribution of wild-type murine macrophages expressing cell surface markers CD11b and CD86 following stimulation with poly (I:C).

FIGS. 12A and 12B show the distribution of bone marrow cells isolated from mice that express cell surface markers B220 and Mac1, 72 hours after the mice were injected with phosphate buffered saline (PBS)(FIG. 12A) or LPS (FIG. 12B). FIGS. 12C and 12D show the distribution of bone marrow cells isolated from mice that express Gr1 and Mac1, 72 hours after the mice were injected with PBS (FIG. 12C) or LPS (FIG. 12D). FIGS. 12E and 12F show the distribution of bone marrow cells isolated from mice that express CD4 and Ter-119, 72 hours after the mice were injected with PBS (FIG. 12E) or LPS (FIG. 12F).

FIGS. 14B and 14C show the distribution GFP$^+$ bone marrow cells isolated from mice reconstituted with HSC's transformed with a control vector (Cont, FIG. 14B), or an miR-155 expression vector MG155 (MG155, FIG. 14C) compared to control (non-reconstituted) mice.

FIG. 17(5) is a bar graph showing the number of cells expressing Mac1/GR1; Ter-119, CD4 or B220 cell surface markers in the bone marrow of control mice (grey) or mice reconstituted with HSC's transformed with MG155 (black). The bar indicates 25 µm.

DETAILED DESCRIPTION OF THE PREFERRED EMBODIMENT

Definitions

Figure 1:
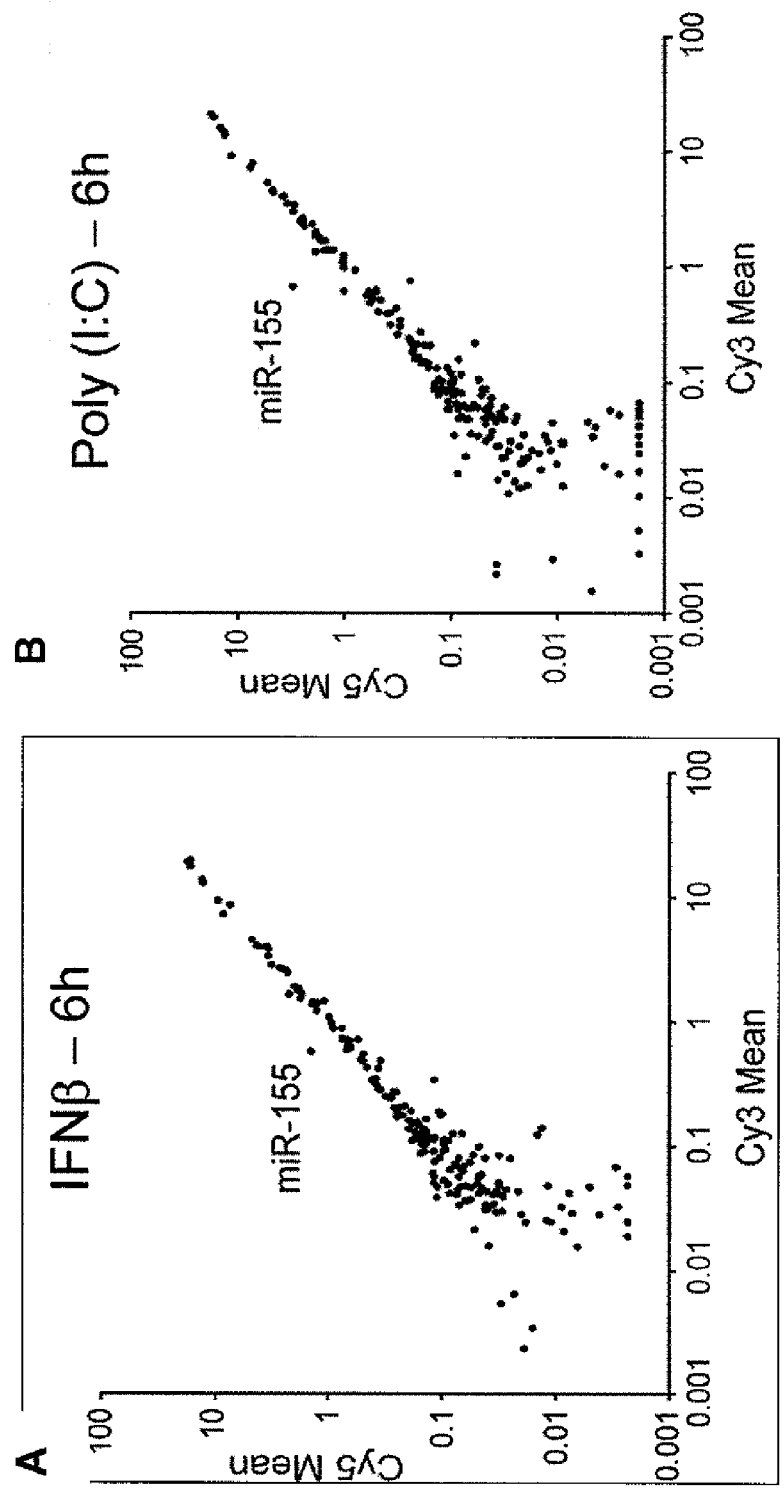
FIGS. 1A-1B are scatter plots showing $\log_{10}$-transformed signal intensities reflecting the amount of microRNA's in wild-type murine macrophages stimulated with media (FIGS. 1A and 1B, Cy3), or stimulated with IFNβ (FIG. 1A, Cy5) or Poly (I:C) (FIG. 1B, Cy3), assessed using a microarray of miRNA's. miR-155 signals are indicated in each plot.

"Subject" means a human or non-human animal selected for treatment or therapy.

"Subject suspected of having" means a subject exhibiting one or more clinical indicators of a disease or condition. In certain embodiments, the disease or condition is inflammation. In certain embodiments, the disease or condition is a myeloproliferative disorder.

"Subject suspected of having inflammation" means a subject exhibiting one or more clinical indicators of inflammation.

"Subject suspected of having a myeloproliferative disorder" means a subject exhibiting one or more clinical indicators of a myeloproliferative disorder.

"Preventing" or "prevention" refers to delaying or forestalling the onset, development or progression of a condition or disease for a period of time, including weeks, months, or years.

"Treatment" or "treat" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Subject in need thereof" means a subject identified as in need of a therapy or treatment.

"Administering" means providing a pharmaceutical agent or composition to a subject, and includes, but is not limited to, administering by a medical professional and self-administering.

"Parenteral administration," means administration through injection or infusion.

Parenteral administration includes, but is not limited to, subcutaneous administration, intravenous administration, intramuscular administration, intraarterial administration, and intracranial administration.

"Subcutaneous administration" means administration just below the skin.

"Intravenous administration" means administration into a vein.

"Intraarterial administration" means administration into an artery.

"Improves liver function" means the changes liver function toward normal parameters. In certain embodiments, liver function is assessed by measuring molecules found in a subject's blood. For example, in certain embodiments, improved liver function is measured by a reduction in blood liver transaminase levels.

"Pharmaceutical composition" means a mixture of substances suitable for administering to an individual that includes a pharmaceutical agent. For example, a pharmaceutical composition may comprise a modified oligonucleotide and a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Target nucleic acid," "target RNA," "target RNA transcript" and "nucleic acid target" all mean a nucleic acid capable of being targeted by antisense compounds.

"Targeting" means the process of design and selection of nucleobase sequence that will hybridize to a target nucleic acid and induce a desired effect.

"Targeted to" means having a nucleobase sequence that will allow hybridization to a target nucleic acid to induce a desired effect. In certain embodiments, a desired effect is reduction of a target nucleic acid.

"Modulation" means to a perturbation of function or activity. In certain embodiments, modulation means an increase in gene expression. In certain embodiments, modulation means a decrease in gene expression.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid. In certain embodiments, a modified oligonucleotide has a nucleobase sequence that is complementary to a region of a target nucleic acid. For example, in certain such embodiments a modified oligonucleotide is complementary to a region of a miRNA stem-loop sequence. In certain such embodiments, a modified oligonucleotide is 100% identical to a region of a miRNA sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means a first nucleobase sequence is at least 60%, 65%, 70%, 75%, 80%, 85%, 90%, 95%, 97%, 98% or 99% identical, or is 100% identical, to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. In certain embodiments a modified oligonucleotide that has a nucleobase sequence which is 100% complementary to a miRNA, or precursor thereof, may not be 100% complementary to the miRNA, or precursor thereof, over the entire length of the modified oligonucleotide.

"Complementarity" means the nucleobase pairing ability between a first nucleic acid and a second nucleic acid.

"Full-length complementarity" means each nucleobase of a first nucleic acid is capable of pairing with each nucleobase at a corresponding position in a second nucleic acid. For example, in certain embodiments, a modified oligonucleotide wherein each nucleobase has complementarity to a nucleobase in an miRNA has full-length complementarity to the miRNA.

"Percent complementary" means the number of complementary nucleobases in a nucleic acid divided by the length of the nucleic acid. In certain embodiments, percent complementarity of a modified oligonucleotide means the number of nucleobases that are complementary to the target nucleic acid, divided by the number of nucleobases of the modified oligonucleotide. In certain embodiments, percent complementarity of a modified oligonucleotide means the number of nucleobases that are complementary to a miRNA, divided by the number of nucleobases of the modified oligonucleotide.

"Percent region bound" means the percent of a region complementary to an oligonucleotide region. Percent region bound is calculated by dividing the number of nucleobases of the target region that are complementary to the oligonucleotide by the length of the target region. In certain embodiments, percent region bound is at least 80%, at least 85%, at least 90%, at least 95%, at least 96%, at least 97%, at least 98%, at least 99%, or 100%.

"Percent identity" means the number of nucleobases in first nucleic acid that are identical to nucleobases at corresponding positions in a second nucleic acid, divided by the total number of nucleobases in the first nucleic acid.

"Substantially identical" used herein may mean that a first and second nucleobase sequence are at least 60%, 65%, 70%, 75%, 80%, 85%, 90%, 95%, 97%, 98% or 99% identical, or 100% identical, over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Non-complementary nucleobase" means two nucleobases that are not capable of pairing through hydrogen bonding.

"Identical" means having the same nucleobase sequence.

"miRNA" or "miR" means a non-coding RNA between 18 and 25 nucleobases in length which hybridizes to and regulates the expression of a coding RNA. In certain embodiments, a miRNA is the product of cleavage of a pre-miRNA by the enzyme Dicer. Examples of miRNAs are found in the miRNA database known as miRBase (http://microrna.sanger.ac.uk/).

"Pre-miRNA" or "pre-miR" means a non-coding RNA having a hairpin structure, which contains a miRNA. In certain embodiments, a pre-miRNA is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (http://microrna.sanger.ac.uk/).

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"Monocistronic transcript" means a miRNA precursor containing a single miRNA sequence.

"Polycistronic transcript" means a miRNA precursor containing two or more miRNA sequences.

"Seed region" means nucleotides 2 to 6 or 2 to 7 from the 5'-end of a mature miRNA sequence.

"Oligomeric compound" means a compound comprising a polymer of linked monomeric subunits.

"Antisense compound" means a compound having a nucleobase sequence that will allow hybridization to a target nucleic acid. In certain embodiments, an antisense compound is an oligonucleotide having a nucleobase sequence complementary to a target nucleic acid.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"miR antagonist" means an agent designed to interfere with or inhibit the activity of a miRNA. In certain embodiments, a miR antagonist comprises an antisense compound targeted to a miRNA. In certain embodiments, a miR antagonist comprises a modified oligonucleotide having a nucleobase sequence that is complementary to the nucleobase sequence of a miRNA, or a precursor thereof. In certain embodiments, a miR antagonist is a miR-155 antagonist. In other embodiments, an miR-155 antagonist comprises a small molecule, or the like that interferes with or inhibits the activity of an miRNA.

"miR-155 antagonist" means an agent designed to interfere with or inhibit the activity of miR-155.

"Modified oligonucleotide" means an oligonucleotide having one or more modifications relative to a naturally occurring terminus, sugar, nucleobase, and/or internucleoside linkage.

"Single-stranded modified oligonucleotide" means a modified oligonucleotide which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro sugar" or "2'-F sugar" means a sugar having a fluoro modification of the 2' position.

"Bicyclic sugar moiety" means a sugar modified by the bridging of two non-geminal ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"Motif" means a pattern of modified and/or unmodified nucleobases, sugars, and/or internucleoside linkages in an oligonucleotide.

A "fully modified oligonucleotide" means each nucleobase, each sugar, and/or each internucleoside linkage is modified.

A "uniformly modified oligonucleotide" means each nucleobase, each sugar, and/or each internucleoside linkage has the same modification throughout the modified oligonucleotide.

A "stabilizing modification" means a modification to a nucleoside that provides enhanced stability to a modified oligonucleotide, in the presence of nucleases, relative to that provided by 2'-deoxynucleotides linked by phosphodiester internucleoside linkages. For example, in certain embodiments, a stabilizing modification is a stabilizing nucleoside modification. In certain embodiments, a stabilizing modification is a internucleoside linkage modification.

A "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

A "stabilizing internucleoside linkage" means an internucleoside linkage that provides enhanced nuclease stability to an oligonucleotide relative to that provided by a phosphodiester internucleoside linkage. In one embodiment, a stabilizing internucleoside linkage is a phosphorothioate internucleoside linkage.

Certain Diseases, Conditions, and Cellular Phenotypes

MiR-155 is strongly induced in cells of the innate immune system after exposure to inflammatory stimuli. As described herein, miR-155 expression in bone marrow-derived macrophages is increased by several Toll-like receptor (TLR) ligands through MyD88 or TRIF signaling and by interferons through TNF-alpha autocrine or paracrine signaling. Thus, miR-155 is a common target of a broad range of inflammatory mediators.

The inflammatory response to infection must be carefully regulated to achieve pathway clearance and prevent the consequences of unrelated gene expression. The inflammatory process is known to have a significant impact on the generation of blood cells from a common hematopoietic stem cell (hematopoiesis) by enhancing the production of granulocyte/monocyte (GM) populations to replenish the cells that become depleted while fighting infection. However, dysregulation of hematopoiesis can lead to excess proliferation of cells, which can in turn lead to various types of malignancies. As described herein, miR-155 expression in bone marrow is induced following exposure to inflammatory stimuli and is correlated with granulocyte/monocyte (GM) expansion. The sustained expression of miR-155 in bone marrow led to profound myeloid proliferation with dysplastic changes, as evidenced by the miR-155-induced GM population of cells displaying pathological features characteristic of myeloid neoplasia (i.e., a myeloproliferative disorder). A comparison of bone marrow from patients with certain subtypes of acute myeloid leukemia (AML) revealed that miR-155 is overexpressed in the bone marrow of these patients, relative to bone marrow samples of healthy donors. Thus, it is demonstrated herein that miR-155 contributes to physiological GM expansion during inflammation and to certain pathological features associated with AML. Accordingly, miR-155 is implicated as a link between the inflammatory response and cancer. Further, miR-155 levels can be used in the diagnosis and/or classification of certain myeloproliferative disorders such as AML. For example, miR-155 can be used in the diagnosis and identification of FAB-ALM-M4 and FAB-AML-M5. The data provided herein demonstrate the importance of proper regulation of miR-155 in developing myeloid cells during the inflammatory response, to avoid excessive activation of the inflammatory response and/or the development of cancer.

Accordingly, miR-155 can be regulated to modulate the innate immune system, for example, in the treatment, prevention or amelioration of diseases characterized by activation, particularly excessive activation, of the innate immune system. In certain embodiments, treatment is provided to a subject suffering from inflammation, or inflammatory-related conditions, such as inflammation arising from a macrophage-induced inflammatory response, mediated through a Toll-like Receptor(s) (TLRs). The inflammation can arise as a result of activation of TLR2, TLR3, TLR4, TLR9, pathways, or the like, for example caused by cancer, viral infection, microbial infection or the like, as described herein. Additional inflammatory-related conditions include, for example, sepsis and septic shock, neurodegeneration, neutrophilic alveolitis, asthma, hepatitis, inflammatory bowel disease, ischemia/reperfusion, septic shock, glomerulonephritis, rheumatoid arthritis, or Crohn's disease. The administration of miR-155 antagonists, such as antisense oligonucleotides, can be used to interfere with or inhibit the activity of miR-155 and thus inhibit or attenuate inflammation.

Further, miR-155 can be regulated to treat, prevent or ameliorate myeloproliferative disorders. Such myeloproliferative disorders include, without limitation, acute myeloid leukemia. In certain embodiments, the acute myeloid leukemia is acute myelomonocytic leukemia or acute monocytic leukemia. MiR-155 antagonists, such as a modified oligonucleotide having a nucleobase sequence complementary to miR-155, can be used to interfere with or inhibit the activity of miR-155, thus inhibiting the excessive proliferation of myeloid cells.

Microarray analyses were employed to identify target genes that are modulated by miR-155. These studies revealed that miR-155 can directly regulate several genes relevant to hematopoiesis and myeloproliferation, including but not limited to Bach1, PU.1, Cutl1, Picalm, Arntl, Csflr, Sla, Jarid2, and HIfla. Accordingly, miR-155 antagonists can be used to modulate the expression of genes involved in hematopoiesis and myeloproliferation. MiR-155 antagonists, such as a modified oligonucleotide having a nucleobase sequence complementary to miR-155, can be delivered to myeloid cells to modulate the expression of miR-155 target genes.

Antagonists of miR-155 can also be used to slow, prevent or inhibit the proliferation of cells in a granulocyte/monocyte cell population. In certain embodiments, the granulocyte/monocyte cell expansion occurs during the inflammatory response.

Additionally, antagonists of miR-155 can be used to slow, prevent or inhibit hematopoietic cell proliferation. In certain embodiments, the hematopoietic cell proliferation comprises myeloid cell proliferation. In certain embodiments, the myeloid cell proliferation is associated with the inflammatory response. In certain embodiments, the myeloid cell proliferation is associated with a myeloproliferative disorder, such as acute myeloid leukemia.

As illustrated herein, elevated miR-155 levels are associated with inflammation. As such, provided herein are methods of detecting miR-155-mediated inflammation in a subject, comprising measuring miR-155 levels in the cells of a subject suspected of having miR-155-mediated inflammation. As further illustrated herein, elevated miR-155 levels are observed in connection with myeloid cell proliferation. Accordingly, provided herein are methods of detecting a miR-155 mediated myeloproliferative disorder in a subject, comprising measuring miR-155 levels in the bone marrow of a subject suspected of having a miR-155-mediated myeloproliferative disorder.

Certain Routes of Administration

In certain embodiments, administering to a subject comprises parenteral administration. In certain embodiments, administering to a subject comprises intravenous administration. In certain embodiments, administering to a subject comprises subcutaneous administration.

In certain embodiments, administration includes pulmonary administration. In certain embodiments, pulmonary administration comprises delivery of aerosolized oligonucleotide to the lung of a subject by inhalation. Following inhalation by a subject of aerosolized oligonucleotide, oligonucleotide distributes to cells of both normal and inflamed lung tissue, including alveolar macrophages, eosinophils, epithelium, blood vessel endothelium, and bronchiolar epithelium. A suitable device for the delivery of a pharmaceutical composition comprising a modified oligonucleotide includes, but is not limited to, a standard nebulizer device. Formulations and methods for modulating the size of droplets using nebulizer devices to target specific portions of the respiratory tract and lungs are well known to those skilled in the art. Additional suitable devices include dry powder inhalers or metered dose inhalers.

In certain embodiments, pharmaceutical compositions are administered to achieve local rather than systemic exposures. For example, pulmonary administration delivers a pharmaceutical composition to the lung, with minimal systemic exposure.

Additional suitable administration routes include, but are not limited to, oral, rectal, transmucosal, intestinal, enteral, topical, suppository, intrathecal, intraventricular, intraperitoneal, intranasal, intraocular, intramuscular, intramedullary, and intratumoral.

Certain Additional Therapies

Treatments for disorders listed herein may comprise more than one therapy. As such, in certain embodiments provided herein are methods for treating a subject having or suspected of having an inflammatory disorder described herein comprising administering at least one therapy in addition to administering a miR-155 antagonist. In certain embodiments, provided herein are methods for treating a subject having or suspected of having a myeloproliferative disorder described herein comprising administering at least one therapy in addition to administering a miR-155 antagonist.

In certain embodiments, the at least one additional therapy comprises a chemotherapeutic agent. In certain embodiments, chemotherapeutic agents include, but are not limited to, cytarabine (also known as cytosine arabinoside or ara-C (Cytosar)), daunorubicin (also known as daunomycin (Cerubidine), idarubicin (e.g., Idamycin), mitoxantrone (e.g., Novantrone), 6-thioguanine (also known as 6-TG), 6-mercaptopurine, (also known as 6-MP; e.g., Purinethol), fludarabine (e.g., Fludara), vincristine (e.g., Oncovin), and etoposide (e.g., VePesid, others).

In certain embodiments, the at least one additional therapy comprises an immunosuppressant. In certain embodiments, an immunosuppressant includes, but is not limited to, a glucocorticoid, a cytostatic, and an antibody. In certain embodiments, an immunosuppressant is a corticosteroid, such as prednisone.

In certain embodiments, the methods provided herein comprise administering one or more additional pharmaceutical agents. In certain embodiments, additional pharmaceutical agents include, but are not limited to, diuretics (e.g. sprionolactone, eplerenone, furosemide), inotropes (e.g. dobutamine, milrinone), digoxin, vasodilators, angiotensin II converting enzyme (ACE) inhibitors (e.g. are captopril, enalapril, lisinopril, benazepril, quinapril, fosinopril, and ramipril), angiotensin II receptor blockers (ARB) (e.g. candesartan, irbesartan, olmesartan, losartan, valsartan, telmisartan, eprosartan), calcium channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide).

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more pharmaceutical compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

Certain Pharmaceutical Compositions

In certain embodiments, a compound comprising a modified oligonucleotide complementary to a miRNA, or precursor thereof, described herein is prepared as a pharmaceutical composition for the treatment of a disorder described herein. In certain embodiments, a compound comprising a modified oligonucleotide having a nucleobase sequence complementary to a miRNA or a precursor thereof is prepared as a pharmaceutical composition for the prevention of a disorder described herein.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising a modified oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention is formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Compounds

In certain embodiments, the methods provided herein comprise administration of a compound comprising a modified oligonucleotide. In certain embodiments, the compound consists of a modified oligonucleotide.

In certain such embodiments, a compound comprises a modified oligonucleotide hybridized to a complementary strand, i.e. a compound comprises a double-stranded oligomeric compound. In certain embodiments, the hybridization of a modified oligonucleotide to a complementary strand forms at least one blunt end. In certain such embodiments, the hybridization of a modified oligonucleotide to a complementary strand forms a blunt end at each terminus of the double-stranded oligomeric compound. In certain embodiments, a terminus of a modified oligonucleotide comprises one or more additional linked nucleosides relative to the number of linked nucleosides of the complementary strand. In certain embodiments, the one or more additional nucleosides are at the 5' terminus of a modified oligonucleotide. In certain embodiments, the one or more additional nucleosides are at the 3' terminus of a modified oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary strand comprises one or more additional linked nucleosides relative to the number of linked nucleosides of a modified oligonucleotide. In certain embodiments, the one or more additional linked nucleosides are at the 3' terminus of the complementary strand. In certain embodiments, the one or more additional linked nucleosides are at the 5' terminus of the complementary strand. In certain embodiments, two additional linked nucleosides are linked to a terminus. In certain embodiments, one additional nucleoside is linked to a terminus.

In certain embodiments, a compound comprises a modified oligonucleotide conjugated to one or more moieties which enhance the activity, cellular distribution or cellular uptake of the resulting antisense oligonucleotides. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to a modified oligonucleotide. In certain embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

Certain Nucleobase Sequences

Provided herein are methods for the treatment or prevention of a disorder such as an inflammatory disorder or a myeloproliferative disorder. In certain embodiments, the methods comprise administration of a pharmaceutical composition comprising a modified oligonucleotide. In certain embodiments, the methods comprise administration of a compound comprising a modified oligonucleotide. In certain embodiments, a modified oligonucleotide has a sequence that is complementary to a miRNA or a precursor thereof. In certain embodiments, the miRNA is miR-155.

Nucleobase sequences of mature miRNAs and their corresponding stem-loop sequences described herein are the sequences found in miRBase, an online searchable database of miRNA sequences and annotation, found at http://microrna.sanger.ac.uk/. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compounds of the present invention encompass modified oligonucleotides that are complementary any nucleobase sequence version of the miRNAs described herein.

It is understood that any nucleobase sequence set forth herein is independent of any modification to a sugar moiety, an internucleoside linkage, or a nucleobase. It is further understood that a nucleobase sequence comprising U's also encompasses the same nucleobase sequence wherein 'U' is replaced by 'T' at one or more positions having 'U.' Conversely, it is understood that a nucleobase sequence comprising T's also encompasses the same nucleobase sequence wherein 'T; is replaced by 'U' at one or more positions having 'T.'

In certain embodiments, a modified oligonucleotide has a nucleobase sequence that is complementary to a miRNA or a precursor thereof, meaning that the nucleobase sequence of a modified oligonucleotide is a least 60%, 65%, 70%, 75%, 80%, 85%, 90%, 95%, 97%, 98% or 99% identical to the complement of a miRNA or precursor thereof over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleobases, or that the two sequences hybridize under stringent hybridization conditions. Accordingly, in certain embodiments the nucleobase sequence of a modified oligonucleotide may have one or more mismatched basepairs with respect to its target miRNA or target miRNA precursor sequence, and is capable of hybridizing to its target sequence. In certain embodiments, a modified oligonucleotide has a nucleobase sequence that is 100% complementary to a miRNA or a precursor thereof. In certain embodiments, the nucleobase sequence of a modified oligonucleotide has full-length complementary to a miRNA.

In certain embodiments, miR-155 has the nucleobase sequence of SEQ ID NO: 72. In certain embodiments pre-miR-155 has the nucleobase sequence of SEQ ID NO: 72.

In certain embodiments, a modified oligonucleotide has a sequence that is complementary to the nucleobase sequence of miR-155 set forth as SEQ ID NO: 73. In certain embodiments, a modified oligonucleotide has a sequence that is complementary to the nucleobase sequence of pre-miR-155 set forth as SEQ ID NO: 72.

In certain embodiments, a modified oligonucleotide has a nucleobase sequence comprising the nucleobase sequence 5'-CCCCUAUCACGAUUAGCAUUAA-3' (SEQ ID NO: 74).

In certain embodiments, a modified oligonucleotide has a nucleobase sequence consisting of the nucleobase sequence set forth as SEQ ID NO: 74.

In certain embodiments, a modified oligonucleotide has a nucleobase sequence that is complementary to a nucleobase sequence of pre-miR-155 set forth as SEQ ID NO: 72.

In certain embodiments, a modified oligonucleotide has a nucleobase sequence that is complementary to a nucleobase sequence having at least 80% identity to the nucleobase sequence set forth in SEQ ID NO: 73. In certain embodiments, a modified oligonucleotide has a nucleobase sequence that is complementary to a nucleobase sequence having at least 85%, at least 90%, at least 92%, at least 94%, at least 96%, or at least 98% identity to the nucleobase sequence set forth in SEQ ID NO: 73.

In certain embodiments, a modified oligonucleotide has a nucleobase sequence that is complementary to a nucleobase sequence having at least 80% identity to a nucleobase sequence of pre-miR-155 set forth in SEQ ID NO: 72. In certain embodiments, a modified oligonucleotide has a nucleobase sequence that is complementary to a nucleobase sequence having at least 85%, at least 90%, at least 92%, at least 94%, at least 96%, or at least 98% identity to a nucleobase sequence of pre-miR-155 set forth in SEQ ID NO: 72.

In certain embodiments, a nucleobase sequence of a modified oligonucleotide has full-length complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA to which it is complementary.

In certain embodiments, the number of linked nucleosides of a modified oligonucleotide is less than the length of the mature miRNA to which it is complementary. In certain such embodiments, the number of linked nucleosides of a modified oligonucleotide is one less than the length of the mature miRNA to which it is complementary. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in a miRNA, is considered to be a modified oligonucleotide having a nucleobase sequence 100% complementary to a portion of a miRNA sequence.

In certain embodiments, the number of linked nucleosides of a modified oligonucleotide is greater than the length of the miRNA to which it is complementary. In certain such embodiments, the nucleobase of an additional nucleoside is complementary to a nucleobase of a miRNA stem-loop sequence. In certain embodiments, the number of linked nucleosides of a modified oligonucleotide is one greater than the length of the miRNA to which it is complementary. In certain such embodiments, the additional nucleoside is at the 5' terminus of a modified oligonucleotide. In certain such embodiments, the additional nucleoside is at the 3' terminus of a modified oligonucleotide. In certain embodiments, the number of linked nucleosides of a modified oligonucleotide is two greater than the length of the miRNA to which it is complementary. In certain such embodiments, the two additional nucleosides are at the 5' terminus of a modified oligonucleotide. In certain such embodiments, the two additional nucleosides are at the 3' terminus of a modified oligonucleotide. In certain such embodiments, one additional nucleoside is located at the 5' terminus and one additional nucleoside is located at the 3' terminus of a modified oligonucleotide.

In certain embodiments, a portion of the nucleobase sequence of a modified oligonucleotide is 100% complementary to the nucleobase sequence of the miRNA, but the modified oligonucleotide is not 100% complementary over its entire length. In certain such embodiments, the number of nucleosides of a modified oligonucleotide having a 100% complementary portion is greater than the length of the miRNA. For example, a modified oligonucleotide consisting of 24 linked nucleosides, where the nucleobases of nucleosides 1 through 23 are each complementary to a corresponding position of a miRNA that is 23 nucleobases in length, has a 23 nucleoside portion that is 100% complementary to the nucleobase sequence of the miRNA and approximately 96% overall complementarity to the nucleobase sequence of the miRNA.

In certain embodiments, the nucleobase sequence of a modified oligonucleotide is 100% complementary to a portion of the nucleobase sequence of a miRNA. For example, a modified oligonucleotide consisting of 22 linked nucleosides, where the nucleobases of nucleosides 1 through 22 are each complementary to a corresponding position of a miRNA that is 23 nucleobases in length, is 100% complementary to a 22 nucleobase portion of the nucleobase sequence of a miRNA. Such a modified oligonucleotide has approximately 96% overall complementarity to the nucleobase sequence of the entire miRNA, and has 100% complementarity to a 22 nucleobase portion of the miRNA.

In certain embodiments, a portion of the nucleobase sequence of a modified oligonucleotide is 100% complementary to a portion of the nucleobase sequence of a miRNA, or a precursor thereof. In certain such embodiments, 15 contiguous nucleobases of a modified oligonucleotide are each complementary to 15 contiguous nucleobases of a miRNA, or a precursor thereof. In certain such embodiments, 16 contiguous nucleobases of a modified oligonucleotide are each complementary to 16 contiguous nucleobases of a miRNA, or a precursor thereof. In certain such embodiments, 17 contiguous nucleobases of a modified oligonucleotide are each complementary to 17 contiguous nucleobases of a miRNA, or a precursor thereof. In certain such embodiments, 18 contiguous nucleobases of a modified oligonucleotide are each complementary to 18 contiguous nucleobases of a miRNA, or a precursor thereof. In certain such embodiments, 19 contiguous nucleobases of a modified oligonucleotide are each complementary to 19 contiguous nucleobases of a miRNA, or a precursor thereof. In certain such embodiments, 20 contiguous nucleobases of a modified oligonucleotide are each complementary to 20 contiguous nucleobases of a miRNA, or a precursor thereof. In certain such embodiments, 22 contiguous nucleobases of a modified oligonucleotide are each complementary to 22 contiguous nucleobases of a miRNA, or a precursor thereof. In certain such embodiments, 23 contiguous nucleobases of a modified oligonucleotide are each complementary to 23 contiguous nucleobases of a miRNA, or a precursor thereof. In certain such embodiments, 24 contiguous nucleobases of a modified oligonucleotide are each complementary to 24 contiguous nucleobases of a miRNA, or a precursor thereof.

Certain Modified Oligonucleotides

In certain embodiments, a modified oligonucleotide consists of 12 to 30 linked nucleosides. In certain embodiments, a modified oligonucleotide consists of 15 to 25 linked nucleosides. In certain embodiments, a modified oligonucleotide consists of 19 to 24 linked nucleosides. In certain embodiments, a modified oligonucleotide consists of 21 to 24 linked nucleosides.

In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides. In certain such embodiments, a modified oligonucleotide comprises linked nucleosides selected from contiguous nucleobases of SEQ ID NO: 74.

Certain Modifications

Modified oligonucleotides of the present invention comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the 2' and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —$C(R^1)=C(R_1)$—, —$C(R_1)=N$—, —$C(=NR_1)$—, —$Si(R_1)(R_2)$—, —$S(=O)_2$—, —$S(=O)$—, —$C(=O)$— and —$C(=S)$—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl ($S(=O)_2$—H), substituted sulfonyl, sulfoxyl ($S(=O)$—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—$(CH_2)_p$—, —O—$CH_2$—, —O—$CH_2CH_2$—, —O—CH(alkyl)-, —NH—$(CH_2)_p$—, —N(alkyl)-$(CH_2)_p$—, —(CH(alkyl))—$(CH_2)_p$—, —NH—O—$(CH_2)_p$—, —N(alkyl)-O—$(CH_2)_p$—, or —O—N(alkyl)-$(CH_2)_p$—, wherein p is 1, 2, 3, 4 or 5 and each alkyl group can be further substituted. In certain embodiments, p is 1, 2 or 3.

In certain embodiments, a 2'-modified nucleoside comprises a 2'-substituent group selected from halo, allyl, amino, azido, SH, CN, OCN, $CF_3$, $OCF_3$, O—, S—, or $N(R_m)$-alkyl; O—, S—, or $N(R_m)$-alkenyl; O—, S— or $N(R_m)$-alkynyl; O-alkylenyl-O-alkyl, alkynyl, alkaryl, aralkyl, O-alkaryl, O-aralkyl, $O(CH_2)_2SCH_3$, O—$(CH_2)_2$—O—$N(R_m)(R_n)$ or O—$CH_2$—C(=O)—$N(R_m)(R_n)$, where each $R_m$ and $R_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro ($NO_2$), thiol, thioalkoxy (S-alkyl), halogen, alkyl, aryl, alkenyl and alkynyl.

In certain embodiments, a 2'-modified nucleoside comprises a 2'-substituent group selected from F, $NH_2$, $N_3$, $OCF_3$, O—$CH_3$, $O(CH_2)_3NH_2$, $CH_2$—CH=$CH_2$, O—$CH_2$—CH=$CH_2$, $OCH_2CH_2OCH_3$, $O(CH_2)_2SCH_3$, O—$(CH_2)_2$—O—$N(R_m)(R_n)$, —$O(CH_2)_2O(CH_2)_2N(CH_3)_2$, and N-substituted acetamide (O—$CH_2$—C(=O)—$N(R_m)(R_n)$) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, $OCF_3$, O—$CH_3$, $OCH_2CH_2OCH_3$, 2'-$O(CH_2)_2SCH_3$, O—$(CH_2)_2$—O—$N(CH_3)_2$, —$O(CH_2)_2O(CH_2)_2N(CH_3)_2$, and O—$CH_2$—C(=O)—N(H)$CH_3$.

In certain embodiments, a 2'-modified nucleoside comprises a 2'-substituent group selected from F, O—$CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a 13-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include 2'-$OCH_3$, 2'-O—$(CH_2)_2$—$OCH_3$, and 2'-F.

In certain embodiments, a modified oligonucleotide of the present invention comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide of the present invention comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and $CH_2$ component parts.

In certain embodiments, a modified oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleotide comprises the same internucleoside linkage modifications throughout. In certain such embodiments, each internucleoside linkage of a uniformly modified oligonucleotide is a phosphorothioate internucleoside linkage.

In certain embodiments, a modified oligonucleotide comprises the same sugar modification at each nucleoside, and further comprises one or more internucleoside linkage modifications. In certain such embodiments, the modified oligonucleotide comprises one modified internucleoside linkage at the 5' terminus and one modified internucleoside linkage at the 3' terminus. In certain embodiments, the modified oligonucleotide comprises two modified internucleoside linkages at the 5' terminus and two modified internucleoside linkages at the 3' terminus. In certain embodiments, the modified oligonucleotide comprises two modified internucleoside linkages at the 5' terminus and three modified internucleoside linkages at the 3' terminus. In certain embodiments, the modified oligonucleotide comprises two modified internucleoside linkages at the 5' terminus and four modified internucleoside linkages at the 3' terminus. In certain such embodiments, the modified internucleoside linkage is a phosphorothioate internucleoside linkage.

In certain embodiments, a modified oligonucleotide is represented by the following formula III:

(5')QxQz$^1$(Qy)$_n$Qz$^2$Qz$^3$Qz$^4$Q-L  (3')

In certain such embodiments, a compound is represented by formula III. In certain embodiments, Q is a 2'-O-methyl modified nucleoside. In certain embodiments, x is phosphorothioate. In certain embodiments, y is phosphodiester. In certain embodiments, each of z1, z2, z3, and z4 is, independently phosphorothioate or phosphodiester. In certain embodiments, n is 6 to 17. In certain embodiments, L is cholesterol. In certain embodiments, n is 12 to 17.

In certain embodiments, x is

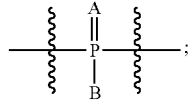

One of A and B is S while the other is O;
y is

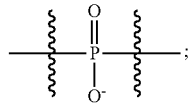 [SMILES: *P(*)(=O)[O-]]

Each of z1, z2, z3, and z4 is independently x or y;
n=6-17
L is

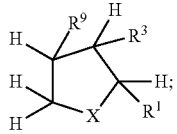

Wherein:
X is N(CO)R$^7$, or NR$^7$;
Each of R$^1$, R$^3$ and R$^9$, is independently, H, OH, or —CH$_2$OR$^b$ provided that at least one of R$^1$, R$^3$ and R$^9$ is OH and at least one of R$^1$, R$^3$ and R$^9$ is —CH$_2$OR$^b$;
R$^7$ is R$^d$ or C$_1$-C$_{20}$ alkyl substituted with NR$^c$R$^d$ or NHC(O)R$^d$;
R$^c$ is H or C$_1$-C$_6$ alkyl;
R$^d$ is a carbohydrate radical; or a steroid radical, which is optionally tethered to at least one carbohydrate radical; and
R$^b$ is

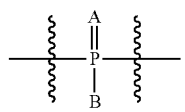

with one of A and B is S while the other is O.
In certain embodiments, R$^d$ is cholesterol. In certain embodiments each of z$^1$, z$^2$, z$^3$, and z$^4$ is

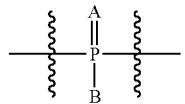

with one of A and B is S while the other is O.
In certain embodiments, R$^1$ is —CH$_2$OR$^b$. In certain embodiments, R$^9$ is OH. In certain embodiments, R$^1$ and R$^9$ are trans. In certain embodiments, R$^9$ is OH. In certain embodiments, R$^1$ and R$^3$ are trans. In certain embodiments, R$^3$ is —CH$_2$OR$^b$. In certain embodiments, R$^1$ is OH. In certain embodiments, R$^1$ and R$^3$ are trans. In certain embodiments, $R^9$ is OH. In certain embodiments, $R^3$ and $R^9$ are trans. In certain embodiments, $R^9$ is $CH_2OR^b$. In certain embodiments, $R^1$ is OH. In certain embodiments, $R^1$ and $R^9$ are trans. In certain embodiments, X is $NC(O)R^7$. In certain embodiments, $R^7$ is —$CH_2(CH_2)_3CH_2NHC(O)R^d$.

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the wings is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2'-O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-O-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different that that of the other external region.

In certain embodiments, the external regions comprise, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiments, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

Certain Quantitation Assays

The effects of antisense inhibition of a miRNA following the administration of modified oligonucleotides may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, antisense inhibition of a miRNA is assessed by measuring the mRNA and/or protein level of a target of a miRNA. Antisense inhibition of a miRNA generally results in the increase in the level of mRNA and/or protein of a target of the miRNA.

Certain Experimental Models

In certain embodiments, the present invention provides methods of using and/or testing modified oligonucleotides of the present invention in an experimental model. In certain embodiments, experimental models are employed to evaluate the effectiveness of modified oligonucleotides of the invention for the treatment of inflammation and/or myeloproliferative disorders. Those having skill in the art are able to select and modify the protocols for such experimental models to evaluate a pharmaceutical agent of the invention.

Modified oligonucleotides may be tested in primary cells or cultured cells. Suitable cell types include those that are related to the cell type to which delivery of a modified oligonucleotide is desired in vivo. For example, suitable cell types for the study of miR-155 antagonists, including modified oligonucleotides, include macrophages, monocytes, granulocytes, lymphocytes, neutrophils, hematopoietic stem cells, and myeloid cells.

In some embodiments, candidate compounds are tested for their activity as miR-155 antagonists in an in vivo model. For example, in some embodiments, a candidate compound can be administered to a mouse, e.g., a mouse that has been irradiated and reconstituted with hematopoietic stem cells (HSC's) that express miR-155 as described, for example, in Example 9 herein. Following administration of a candidate compound to the reconstituted mice, the bone marrow, thymus, spleen and lymph nodes can be removed and assessed for histological changes associated with miR-155 expression in HSC's, such as myeloproliferative disorders present in the bone marrow, splenomegaly, evidence of extramedullary hematopoiesis, and perturbation of peripheral blood cell populations, as described herein. In some embodiments, bone marrow, splenocytes, and peripheral blood cells of the mice can be analyzed for cell surface markers as a means to assess the presence and amount of certain cell types in bone marrow, spleens, peripheral blood, etc. of the mice. For example, bone marrow, splenocytes, and peripheral blood can be analyzed by fluorescence activated cell sorting (FACS) for the presence and amount of $Mac1^+$, $CD4^+$, $B220^+$, $Ter-199^+$, and $Gr1^+$-expressing cells, and the like, as described herein. Levels of miR-155 expression in bone marrow, splenocytes, peripheral blood cells obtained from the mice treated with the candidate compound can be measured. The histology of organs and tissues, the cell population/distribution, and the gene expression measurements in the mice treated with the candidate compound can be compared to untreated mice (e.g., mice reconstituted with miR155 expressing HSC's) as well as control mice (e.g., non-irradiated, non-reconstituted). A decrease in the expression of miR-155 in certain cell populations, a decrease in the extent of splenomegaly or other histological changes associated with miR-155 expression, or decrease in the cell population changes associated with miR-155 expression compared to reconstituted mice that did not receive the candidate compound indicates that the candidate compound can be used therapeutically as an miR-155 antagonist.

In certain embodiments, the extent to which a modified oligonucleotide inhibits the activity of a miRNA is assessed in primary cells or cultured cells. In certain embodiments, inhibition of miRNA activity may be assessed by measuring the levels of the miRNA. Alternatively, the level of a predicted or validated miRNA target may be measured. An inhibition of miRNA activity may result in the increase in the mRNA and/or protein of a miRNA target. Further, in certain embodiments, certain phenotypic outcomes may be measured. For example, suitable phenotypic outcomes include inhibition of cell proliferation, the induction of cell death, and/or the induction of apoptosis.

Following the in vitro identification of a modified oligonucleotide that effectively inhibits the activity of a miRNA, modified oligonucleotides are further tested in in vivo experimental models, such as those described in the Examples.

The following examples are presented in order to more fully illustrate some embodiments of the invention. They should, in no way be construed, however, as limiting the broad scope of the invention.

EXAMPLES

Example 1

IFN-β and Poly (I:C) Induce Expression of miR-155 in Macrophages

The following example describes experiments to test whether virally relevant stimuli induce expression of miRNA's.

Macrophages were matured from murine bone marrow and stimulated with either the synthetic viral intermediate poly (I:C) (double-stranded RNA), or the host antiviral response cytokine, IFN-β. To obtain the macrophages, bone marrow cells were isolated from the tibias and femurs of mice as described in Doyle et al. (2002) *Immunity* 17:251-263. For the experiments described herein, WT, $MyD88^{-/-}$, $TRIF^{-/-}$, $IFNAR^{-/-}$, and $TNFR^{-/-}$ mice, all of which are on a C57BL/6 genetic background, were bred and housed in the University of California Division of Laboratory Animal Medicine facility and killed according to established protocols approved by the Animal Research Committee. Bone marrow was collected using routine protocols, and RBCs were lysed by using a RBC lysis buffer (Invitrogen, San Diego, Calif.). The remaining bone marrow cells were plated out in DMEM containing 10% FBS, 100 units/ml penicillin, and 100 units/ml streptomycin and supplemented with macrophage colony-stimulating factor-conditioned medium at a previously established concentration. Cells were cultured in a humidified incubator with 5% $CO_2$ at 37° C. After 7 days of culture, a portion of the macrophages were stained with specific antibodies and analyzed by FACS to ensure proper differentiation ($CD11b^+F4/80^+$ $CD11c^-$) and subsequently used for experiments.

For FACS, RBC-depleted splenocytes were stained in FACS buffer (1×PBS/0.1% BSA/2% FBS/0.1% normal mouse serum) by using phycoerythrin-conjugated anti-CD11b or FITC-conjugated anti-CD86 (eBiosciences, San Diego, Calif.) and fixed with paraformaldehyde (1% final concentration). Surface expression was assayed by using a FACScan® flow cytometer (Becton Dickenson, Franklin Lakes, N.J.).

Primary macrophages were stimulated by using fresh DMEM containing one of the following: 2 µg/ml poly(I:C) (Amersham Pharmacia, Piscataway, N.J.), 1,000 units/ml mIFN-β (R&D Systems, Minneapolis, Minn.). The cells were stimulated for six hours, at which time total RNA was isolated from the cells and used in microarray screening, quantitative PCR (qPCR), or Northern Blotting.

The microarray screening procedure is the same as described in Taganov, et al. (2006) *Proc. Nat. Acad. Sci. USA* 103:12481-12486. RNA from stimulated macrophages was collected by using the mirVana® RNA isolation kit (Ambion, Austin, Tex.); 30 µg was enriched for small RNAs, tailed by using the mirVana® miRNA labeling kit (Ambion), and labeled with either Cy3 (control samples) or Cy5 (stimulated samples) fluorescent dyes (Amersham Pharmacia, Piscataway, N.J.). The stimulated and control samples were next mixed and incubated for 14 h with miRNA array slides. The epoxy-coated slides (Schott-Nexterion, Louisville, Ky.) were prepared in quadruplicate by using robotics for the spotting of 200 mouse and human sequences complimentary to different mammalian miRNAs (mirVana® miRNA Probe Set; Ambion, Austin, Tex.). After hybridization, microarrays were scanned with a GenePix®c 4200A scanner (Axon Instruments, Foster City, Calif.) by using Gene Pix 5.0 software (Axon Instruments). Raw data were imported into the Resolver gene expression data analysis system version 4.0

(Rosetta Biosoftware, Seattle, Wash.) for further processing. The microarray data for IFN-β stimulated cells are shown in FIG. 1A. The microarray data for poly (I:C) stimulated cells are shown in FIG. 1B. miR-155 was the only miRNA substantially induced by both poly (I:C) and IFN-β. FIGS. 1A and 1B.

Figure 2:
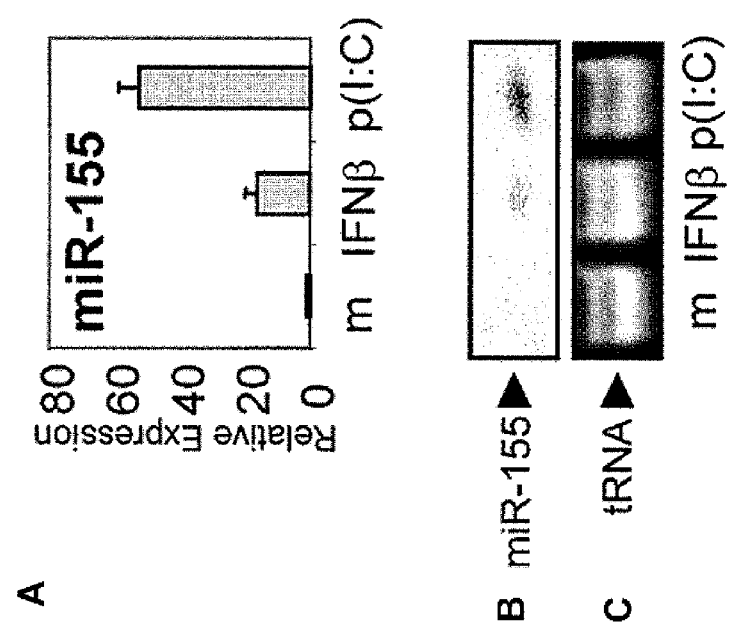
FIG. 2A is a graph showing the relative expression of miRNA-155 in wild-type murine macrophages stimulated with media alone (m), IFNβ, or poly (I:C), as measured by quantitative PCR.
FIG. 2B is an image of a Northern Blot probing for miRNA-155 in wild-type murine macrophages stimulated with media (m), IFNβ, or poly (I:C).
FIG. 2C is an image of the gel used for the Northern Blot shown in FIG. 2B. Shown is the band corresponding to tRNA for each of the murine macrophage cultures, media (m), IFNβ, and poly (I:C).
Figure 3:
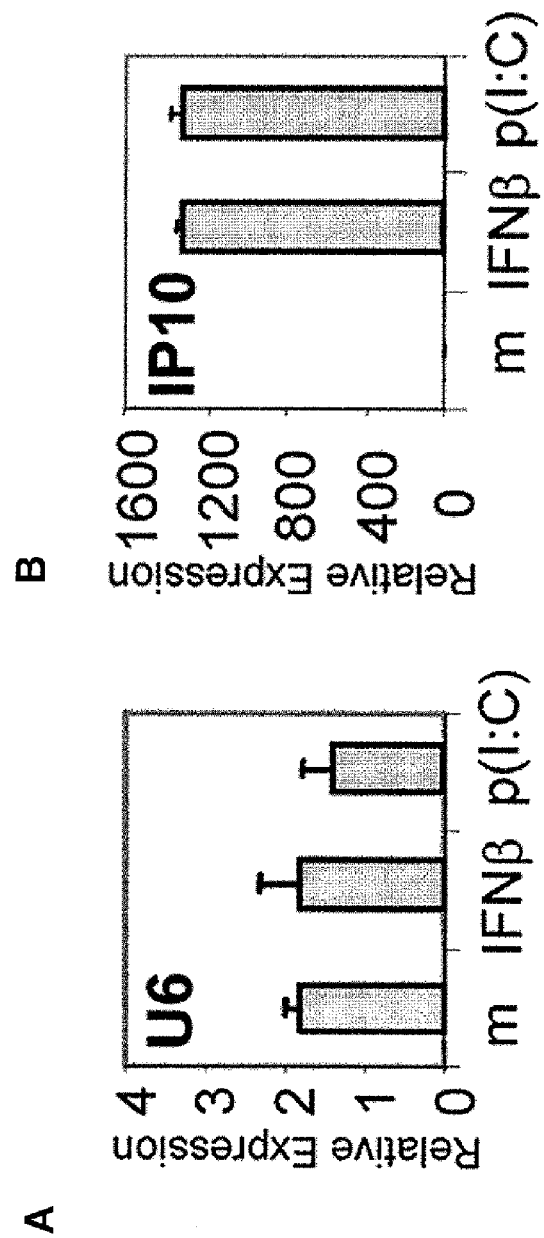
FIGS. 3A-3B are graphs showing the relative expression of U6 (FIG. 3A) and IP10 (FIG. 3B) mRNA's in wild-type murine macrophages stimulated with media (m), IFNβ, or poly (I:C), as measured by quantitative PCR.

To confirm the microarray data showing that miR-155 transcript was induced by IFN-β and poly (I:C), the total RNA isolated as described above was used in quantitative PCR (qPCR) and Northern Blot analysis. For qPCR, total RNA was harvested from bone-marrow-derived macrophages by using the TRIzol® Reagent (Invitrogen) according to the manufacturer's protocol. 1 µg of total RNA was converted to cDNA by using iScript® (Invitrogen, Carlsbad, Calif.) according to the manufacturer's protocol. Cybergreen-based real-time qPCR was performed by using the 7300 Real-Time PCR system (Applied Biosystems, Foster City, Calif.) and gene-specific primers for TNF-α, IP10, and L32 as described in Doyle, et al. (2002) *Immunity* 17:251-263; Kracht et al., (2002) *Cytokine* 20:91-106. All qPCR data were normalized to L32 values. To detect the expression of L32 mRNA, cDNA was subjected to PCR and run out on a 2% agarose gel containing ethidium bromide at 1 µg/ml. The primer sequences used to detect BIC were 5'-ttggcctctgactgactcct-3' (forward) (SEQ ID NO: 1) and 5'-gcagggtgactcttggactt-3' (reverse) (SEQ ID NO: 2). The relative levels of expression of miR-155 in cultures stimulated with culture medium alone (m), INF-β, or poly (I:C) were determined. The data are shown in FIG. 2A. qPCR confirmed induction of miR-155 expression in macrophages in response to stimulation with IFN-β and poly (I:C). qPCR also confirmed that the small nuclear RNA U6 is not induced in macrophages by either IFN-β or poly (I:C) stimulation (FIG. 3A). As expected, IP10 is an IFN-β target. IP10 mRNA was induced by both IFN-β and poly (I:C) (FIG. 3B).

For detection of miR-155 by Northern blotting, RNA was extracted by using the TRIzol® RNA extraction reagent (Invitrogen, Carlsbad, Calif.) according to the manufacturer's protocol. 15 µg of total RNA was electrophoretically separated on a 12% polyacrylamide denaturing gel, and tRNA was visualized by using ethidium bromide staining to ensure the quality and relative amount of the RNA. (FIG. 2C). Total RNA was next transferred to a GeneScreenPlus membrane (PerkinElmer, Boston, Mass.) by using a semidry Transblot electrophoresis apparatus (Bio-Rad, Hercules, Calif.). The RNA was crosslinked to the membrane by using UV radiation. Hybridization was carried out by using ULTRAHybOligo® solution (Ambion, Austin, Tex.) according to the manufacturer's instructions. The probe sequence was complementary to the mature form of miR-155, and was labeled with γ-$^{32}$P. After washing, the membranes were imaged by using a STORM® phosphorimager (GE Healthcare Life Sciences, Piscataway, N.J.). Detection of miR-155 and U6 was also performed by using the mirVana® qRT-PCR miRNA detection kit (Ambion, Austin, Tex.) according to the manufacturer's instructions. FIG. 2B is an image of the Northern Blot. The Northern Blot confirmed the induced expression of miR-155 in macrophages stimulated with either IFN-β or poly (I:C).

Figure 4:
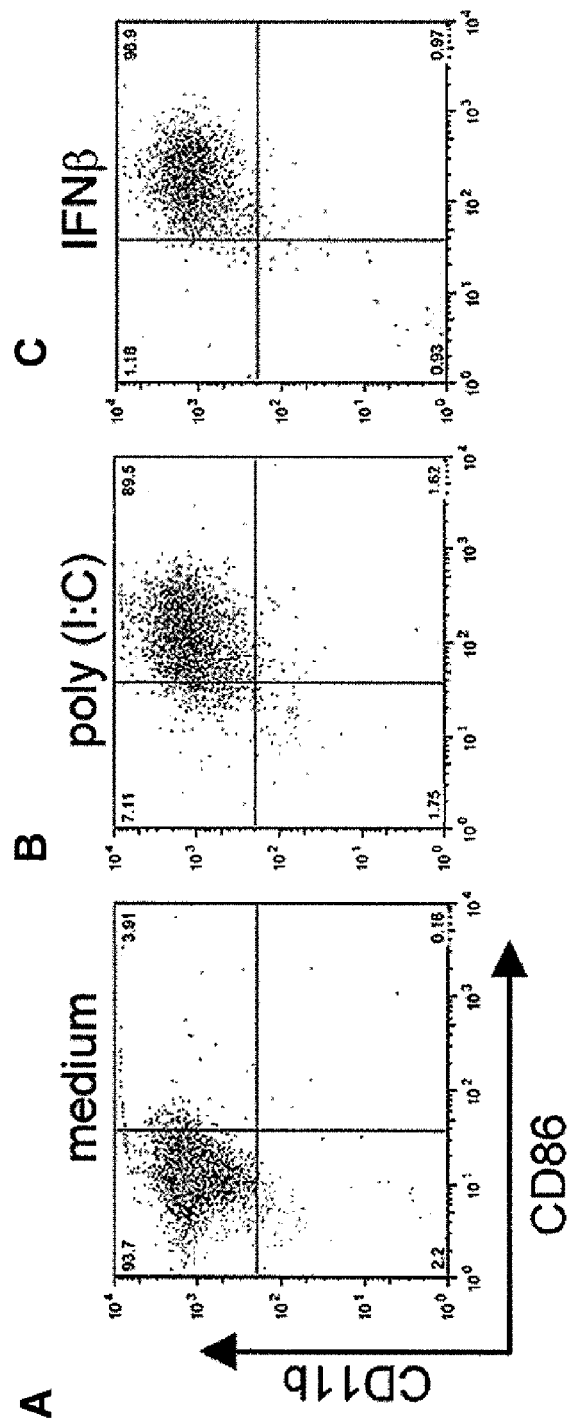
FIGS. 4A-4C are plots of fluorescence activated cell sorting (FACS).

To determine whether the macrophage marker CD11b and the IFN-β target gene were induced after 24 hours of stimulation with either IFN-β or poly (I:C), RBC-depleted splenocytes were stained in FACS buffer (1×PBS/0.1% BSA/2% FBS/0.1% normal mouse serum) by using phycoerythrin-conjugated anti-CD11b or FITC-conjugated anti-CD86 (eBiosciences, San Diego, Calif.) and fixed with paraformaldehyde (1% final concentration). Surface expression was assayed by using a FACScan® flow cytometer (Becton Dickenson, Franklin Lakes, N.J.). The FACS data are presented in FIGS. 4A-4C. Expression of the cell surface marker CD86 was up-regulated following stimulation with both poly (I:C) (FIG. 4B) and IFN-β (FIG. 4D).

The data presented in this example indicate that macrophages respond to viral cues by strongly up-regulating miR-155, an miRNA that is known from other studies to function as an oncogene.

Example 2

Figure 5:
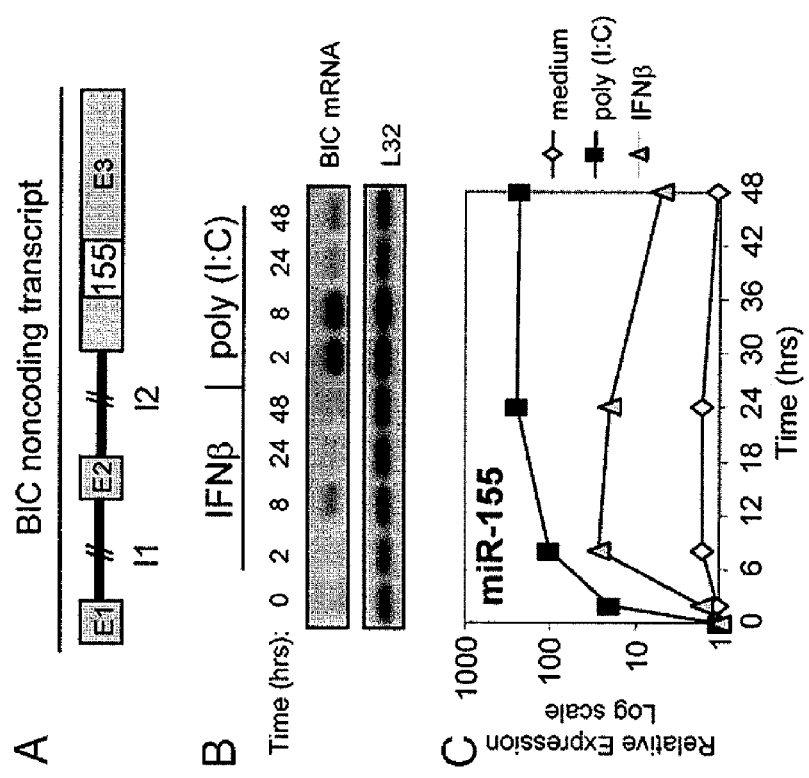
FIG. 5A is a graphical depiction of the human BIC non-coding RNA gene showing the location of miR-155 in exon 3. "E" represents "exon", "I" represents "intron".
FIG. 5B is an image of an agarose gel showing BIC mRNA levels in wild-type murine macrophage cells treated with media supplemented with IFNβ or poly (I:C), as measured by RT-PCR, at indicated time points following treatment. Levels of L32 RNA prepared from mRNA from the same cultures are also shown.
FIG. 5C is a graph showing the relative expression levels (logarithmic scale) of miR-155 over time in wild-type murine macrophage cells treated with media (m), IFNβ, or poly (I:C), as measured by quantitative PCR.

Kinetics of miR-155 Induction in Macrophages Following Poly (I:C) and IFN-β Stimulation miR-155 is found within the BIC gene on chromosome 21 in humans and 16 in mice. The genomic structure of human BIC consists of three exons, and its transcript is transcribed and processed into two differently sized mRNA molecules through alternative polyadenylation. BIC lacks a large ORF and therefore is unlikely to encode a protein. Without intending to be bound by any particular theory, it is possible that the sole function of BIC may be to give rise to miR-155 encoded within exon 3. An unscaled graphical depiction of the genomic structure of the human BIC noncoding RNA gene is shown in FIG. 5A. The location of miR-155 within exon 3 is shown (155). The sequence of human BIC cDNA (SEQ ID NO: 71), pre-miR-155 (SEQ ID NO: 72) and mature miR-155 (SEQ ID NO: 73) from *homo sapiens* are known. E is et al. (2005) *Proc. Nat. Acad. Sci. USA* 102:3627-3632.

To monitor the kinetics of miR-155 induction, both BIC mRNA and mature miR-155 were assayed over a 48-h time course after poly(I:C) or IFN-β stimulation of primary macrophages. Briefly, murine macrophages were isolated and stimulated with culture medium (medium), poly (I:C), or IFN-β over 48 hours as described in Example 1. Samples of the cultures were harvested for RNA isolation at 0 hours, 8 hours, 24 hours, and 48 hours post-stimulation. Total RNA was isolated as described in Example 1. Reverse transcription with an oligonucleotiide dT primer was performed as described in Example 1. The cDNA was used as a template in PCR and run out on a 2% agarose gel containing ethidium bromide at 1 µg/ml. The primer sequences used to detect BIC were 5'-ttggcctctgactgactcct-3' (forward) (SEQ ID NO: 1) and 5'-gcagggtgactcttggactt-3' (reverse) (SEQ ID NO: 2). The relative levels of expression of miR-155 in cultures stimulated with culture medium alone (m), INF-β, or poly (I:C) were determined. Detection of L32 was determined as described in Example 1. The data are shown in FIG. 5B.

A portion of the RNA was used in qPCR to detect miR-155 (mature) over the same 48 hour time period. qPCR was performed as described in Example 1. The relative expression of miR-155 mRNA is shown on a logarithmic scale at the indicated time points, in FIG. 5C. In response to poly(I:C), BIC mRNA became detectable by 2 h, remained elevated to 8 h, and was still present at reduced levels by 24 and 48 h after stimulation. FIG. 5B. miR-155 induction by poly(I:C) followed a similar pattern of expression as BIC, with the exception of remaining at its highest levels at the 24- and 48-h time points. FIG. 5C. IFN-β did not induce BIC mRNA by 2 h, but it was detected by 8 h and was nearly undetectable by 24 and 48 h. FIG. 5B. IFN-β induction of miR-155 followed the same delayed pattern of induction as BIC, reaching its highest levels by 8 h and slowly decreasing by 24 and 48 h after stimulation. FIG. 5C.

These findings demonstrate that the regulation of miR-155 levels involves BIC mRNA up-regulation by poly(I:C) or IFN-β Furthermore, these data show that miR-155 is an immediate early target gene of poly(I:C)-induced signaling, whereas its induction is relatively delayed downstream from IFN-β stimulation.

Example 3

Various Toll-Like Receptor (TLR) Ligands Induce miR-155 in Macrophages

TLR3 is a receptor for poly(I:C). The following experiments were conducted to determine whether other TLR ligands induce miR-155. Specifically, the experiments described below assess the affects of stimulation with LPS, which signals through TLR4; hypomethylated DNA (CpG), a TLR9 ligand; and Pam3CSK4, a synthetic lipoprotein that activates TLR2, on miR-155 expression in primary macrophages.

Figure 6:
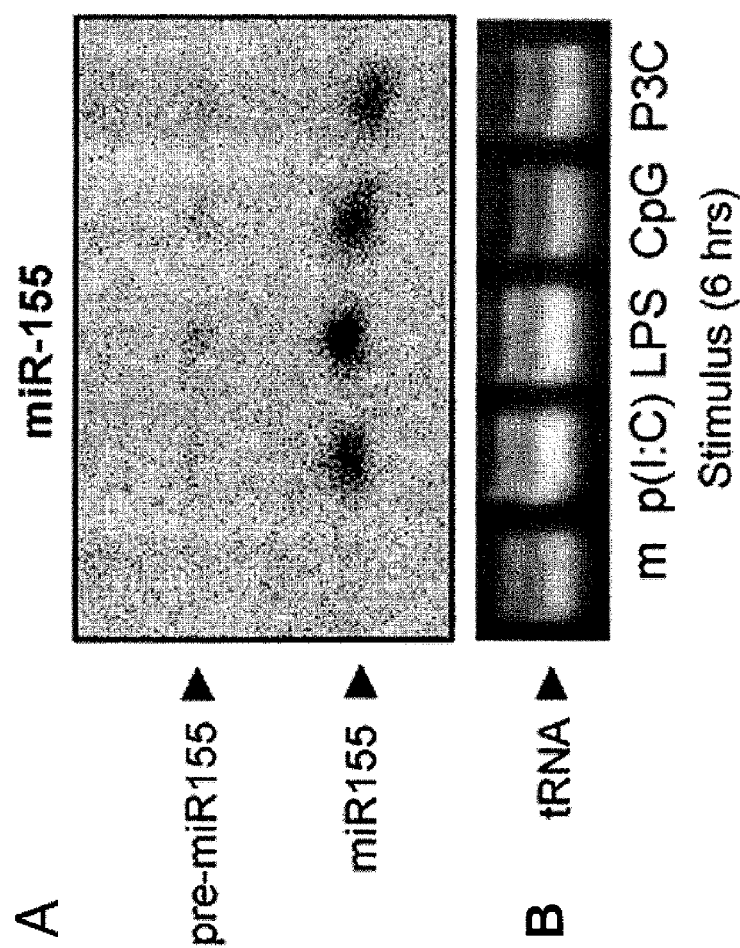
FIG. 6 is an image of a Northern Blot of RNA isolated from wild-type murine macrophages stimulated with media (m), poly (I:C), LPS, CpG, or Pam3CSK4 (P3C), using probes for miR-155. The bands corresponding to mature miR-155 and miR-155 are shown. Also shown is an image of the agarose gel used in the Northern Blotting experiments, stained with ethidium bromide. The band corresponding to tRNA is shown on the agarose gel.

Macrophages were isolated from murine bone marrow as described in Example 1. The macrophages were stimulated by using fresh DMEM containing one of the following: 2 μg/ml poly(I:C) (Amersham Pharmacia, Piscataway, N.J.); 5 ng/ml 055-B5 LPS (Sigma, St. Louis, Mo.), 100 nM CpG 1668 oligonucleotides (Invitrogen, Carlsbad, Calif.), 2 μg/ml Pam3CSK4 (Invitrogen, Carlsbad, Calif.). After 6 h, RNA was harvested from these cells and analyzed by Northern Blot to detect BIC mRNA, or mature miR-155, as described in Example 1. The data are shown in FIG. 6. These data demonstrate that all four TLR ligands tested strongly induced miR-155 expression, and show that miR-155 is induced by the same TLR's that recognize pathogen-associated molecular patterns from viruses and other pathogens.

Example 4

Toll-Like Receptor Adaptors are Required for miR-155 Induction in Response to TLR Ligands in Macrophages TLRs signal through the MyD88 family of adaptor proteins. Of these adaptors, TLR2 and TLR9 signaling is known to require MyD88, whereas TLR3 utilizes TRIF. Adaptors can also play partially redundant roles; for instance, TLR4 signals through either MyD88 or TRIF. This example describes experiments to determine whether MyD88 and TRIF adaptors are required for TLR induction of miR-155.

Figure 7:
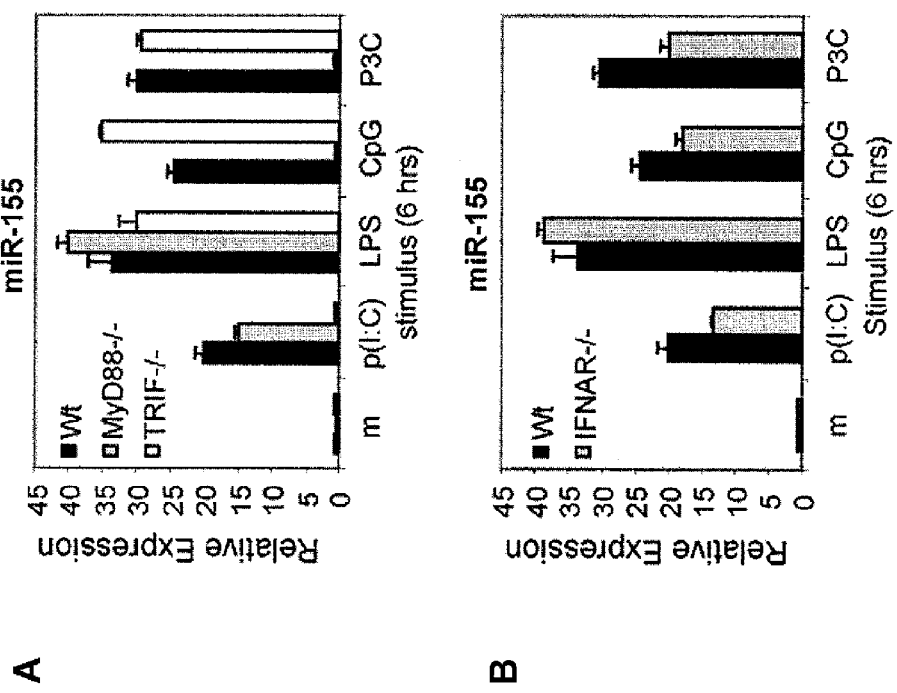
FIG. 7A is a graph showing relative expression of miR-155 in wild-type, MyD88$^{-/-}$, and TRIF$^{-/-}$ murine macrophages stimulated with medium, poly (I:C), LPS, CpG, or Pam3CSK4 (P3C), as measured by quantitative PCR.
FIG. 7B is a graph showing relative expression of miR-155 in wild-type and IFNAR$^{-/-}$ murine macrophages stimulated with medium, poly (I:C), LPS, CpG, or Pam3CSK4 (P3C), as measured by quantitative PCR.

Briefly, macrophages were isolated from WT mice, or mice deficient in either TRIF or MyD88 as described in Example 1. The isolated macrophages were stimulated for 6 hours with either medium (m), the TLR ligands poly (I:C) (p:(I:C)), LPS, CpG or Pam3CSK4 (P3C), as described in Example 1. Total RNA was isolated from the cells, and relative levels of miR-155 expression were measured by qPCR as described in Example 1. The data are presented in FIG. 7A. CpG (TLR9)- or Pam3CSK4 (TLR2)-treated macrophages required MyD88, but not TRIF, to induce miR-155. FIG. 7A. On the other hand, poly(I:C) (TLR3) required TRIF but not MyD88. TLR4 up-regulated miR-155 in the absence of either single adaptor.

These data confirm the specificity of the TLR ligands used and demonstrate that either MyD88- or TRIF-dependent signaling pathways are sufficient to induce miR-155.

A subset of TLR-responsive genes require IFN-β autocrine/paracrine signaling for their induction. Because miR-155 is up-regulated by both TLRs and IFN-β the following experiments were conducted to determine whether TLR induction of miR-155 required IFN-β autocrine/paracrine signaling. Macrophages were isolated from both wild-type (WT) and IFNAR$^{-/-}$ mice, as described in Example 1. Macrophages were stimulated with poly(I:C), LPS, CpG, or Pam3CSK4 as described above. miR-155 expression was measured by qPCR as described in Example 1. The data are presented in FIG. 7B. TLRs do not require IFN-β production for early up-regulation of miR-155 in response to stimulation with poly (I:C), LPS, CpG, or Pam3CSK4. FIG. 7B.

Example 5

IFN's Induce miR-155 Expression Through TNF-α Autocrine/Paracrine Signaling

Similar to IFN-α, IFN-γ is produced in response to viral and bacterial infections and plays an important role in macrophage activation. Accordingly, the following experiments were carried out to determine whether IFN-γ also induced miR-155 expression in macrophages. Because IFN induction of BIC mRNA and mature miR-155 was delayed compared with that of poly(I:C), it appeared that IFNs might use a protein intermediate to up-regulate miR-155. TNF-α has been shown to have autocrine/paracrine signaling after IFN-γ stimulation of macrophages. Accordingly, experiments set forth below were conducted to determine whether IFN induction of miR-155 required TNF-α autocrine/paracrine signaling.

Figure 8:
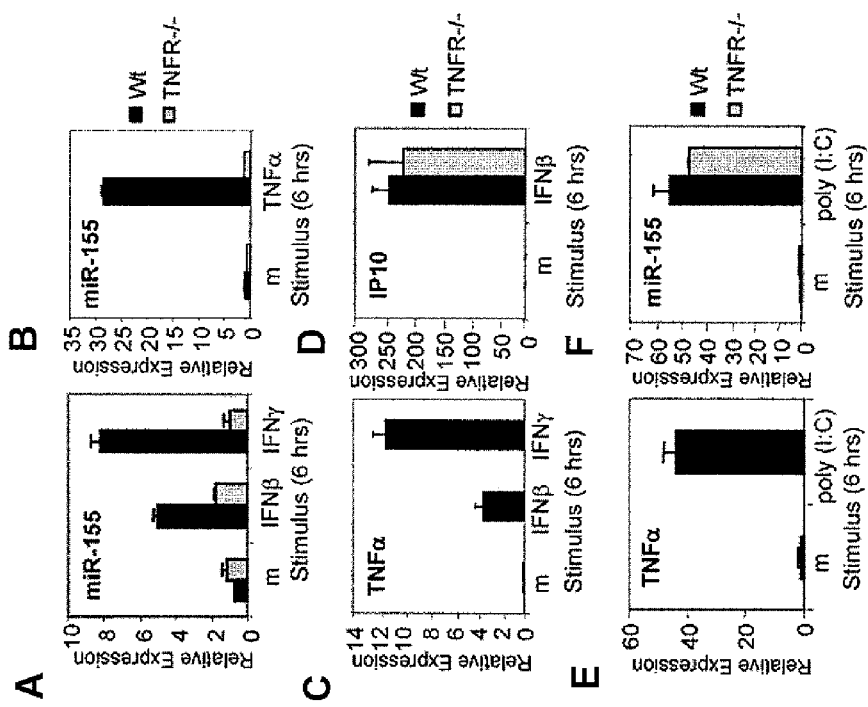
FIG. 8A is a graph showing relative expression of miR-155 in wild-type and TNFR$^{-/-}$ murine macrophages stimulated with medium, IFNβ, or IFNγ as measured by quantitative PCR.
FIG. 8B is a graph showing relative expression of miR-155 in wild-type and TNFR$^{-/-}$ murine macrophages stimulated with medium, or TNFα as measured by quantitative PCR.
FIG. 8C is a graph showing relative expression of TNFα in wild-type and TNFR$^{-/-}$ murine macrophages stimulated with medium, IFNβ, or IFNγ as measured by quantitative PCR.
FIG. 8D is a graph showing relative expression of IP10 in wild-type and TNFR$^{-/-}$ murine macrophages stimulated with medium or IFNβ, as measured by quantitative PCR.
FIG. 8E is a graph showing relative expression of TNFα in wild-type and TNFR$^{-/-}$ murine macrophages stimulated with medium or poly (I:C) as measured by quantitative PCR.
FIG. 8F is a graph showing relative expression of miR-155 in wild-type and TNFR$^{-/-}$ murine macrophages stimulated with medium or poly (I:C) as measured by quantitative PCR.

Briefly, macrophages were isolated from wild-type (WT) and TNFR1$^{-/-}$ mice as described in Example 1. The macrophages were stimulated with medium (m), 1,000 units/ml IFN-β, 50 ng/ml IFN-γ, or 10 ng/ml TNF-α for 6 h, as described in Example 1. miR-155 was assayed by qPCR as described in Examples 1-3. The data are presented in FIGS. 8A and 8B. IFN-γ induced miR-155 in macrophages after 6 hours stimulation. FIG. 8A. This effect was dependent upon TNFR. FIG. 8A. IFN-β and IFN-γ failed to up-regulate miR-1'55 in the absence of TNFR1 signaling as compared with the induction in WT cells. FIG. 8A. TNF-α was sufficient to induce miR-155 expression in a TNFR1-dependent manner. FIG. 8B.

To test whether IFN-β and IFN-γ induced TNF-α expression, WT macrophages were stimulated with culture medium (m), IFN-β, or IFN-γ for 6 h, and TNF-α mRNA levels were determined by qPCR as described in Examples 1-3. The Same RNA was also used in qPCR to measure the amount of IP10 expression following stimulation with culture medium or IFN-β, as described in Example 1. The results are shown in FIGS. 8C and 8D. Both IFN-β and IFN-γ induced TNF-α expression (FIG. 8C). IFN-β induction of IP10 remained intact in TNFR1$^{-/-}$ macrophages (FIG. 8D). These data demonstrate that TNFR1$^{-/-}$ cells can still respond to IFN treatment.

Next, WT macrophages were stimulated with medium or 2 μg/ml poly(I:C) for 6 h and assayed for TNF-α expression by qPCR as described above. In addition, WT and TNFR1$^{-/-}$ macrophages were stimulated with medium or poly(I:C) for 6 h, and miR-155 was assayed by qPCR. Poly (I:C) induced TNF-α expression. The poly (I:C) induction of miR-155 did not require TNF-α auto-signaling (FIGS. 8E, 8F).

Together, these data demonstrate that TNF-α is an inducer of miR-155 and that IFN's require TNF-α. Finally, whereas poly (I:C) induced TNF-α expression, this induction did not require TNF-α autorcine/paracrine signaling to up-regulate miR-155 in macrophages.

Example 6

The JNK Pathway is Involved in Up-Regulation of miR-155 in Response to Poly (I:C) and TNF-α

The following experiments were conducted to identify signaling pathways involved in miR-155 induction. Sequence analysis of the promoter region of the BIC gene conserved between mice and humans, showed two putative AP-1 transcription factor binding sites. The AP-1 transcriptional complex is known to be activated by inflammatory stimuli including TLR ligands and TNF-α. The following experiments were conducted to test whether the JNK pathway is involved in imR-155 induction.

Figure 9:
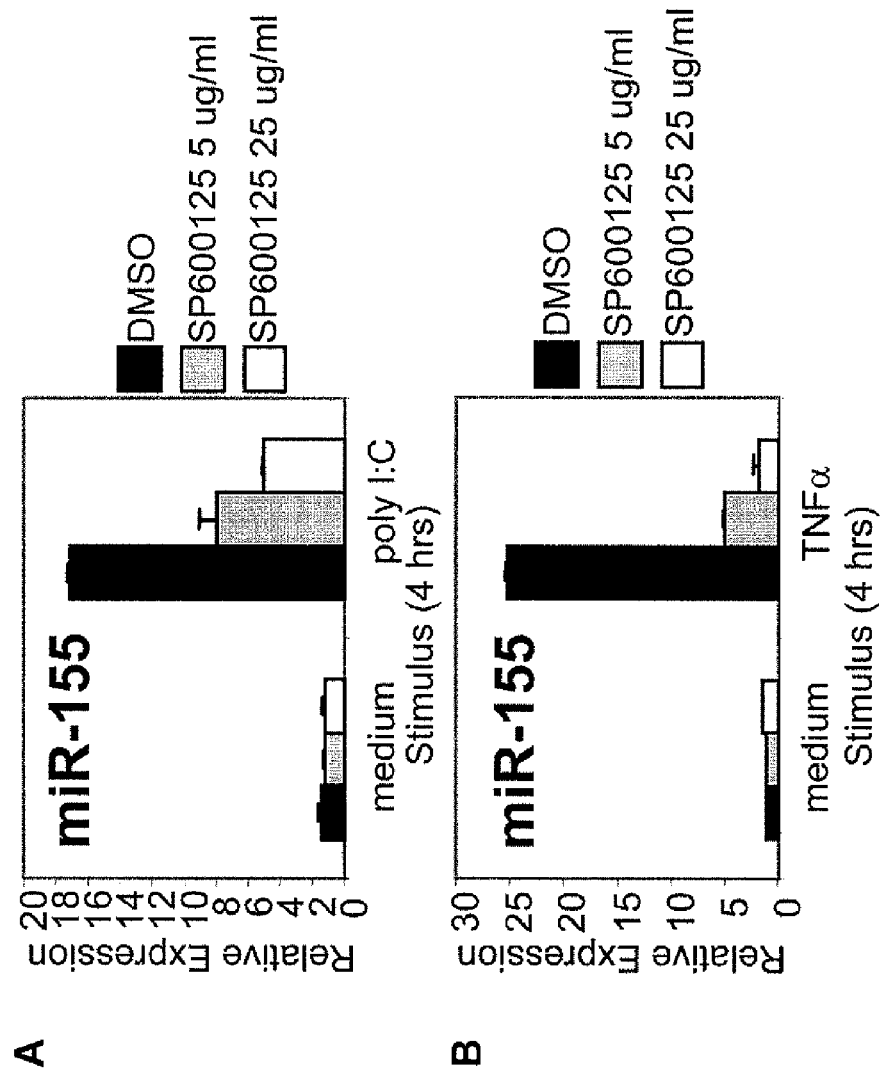
FIGS. 9A-9B are graphs of the relative expression of miR-155 in wild-type murine macrophages pretreated with DMSO or sp6000125, and subsequently stimulated with medium, poly (I:C) (FIG. 9A) or TNFα (FIG. 9B).
Figure 10:
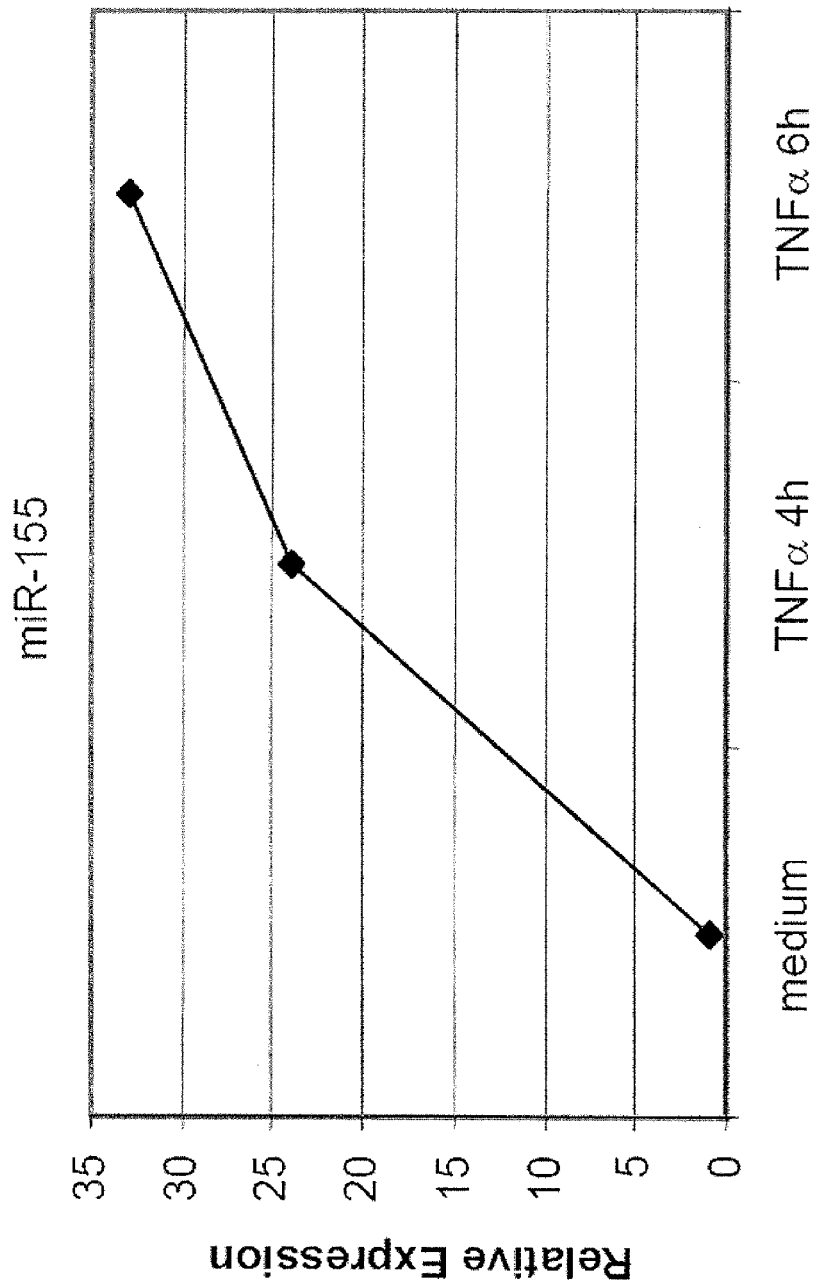
FIG. 10 is a graph showing the relative expression of miR-155 over time in wild-type murine macrophages stimulated with TNFα.

WT murine macrophages were isolated as described in Example 1 and treated for 30 minutes with either 5 μg/mL SP600125, 25 μg/mL SP600125, uo126 (Calbiochem, La Jolla, Calif.) dissolved in DMSO, or DMSO alone. The macrophages were subsequently stimulated with culture medium (m), poly (I:C), or TNF-α, as described in Example 1, for 4 hours. miR-155 expression was measured by qPCR as described in Example 1. The data are presented in FIGS. 9A-9B and 10. Vehicle-treated cells up-regulated miR-155 levels by 4 hours after stimulation, whereas the JNK inhibitor SP600125 blocked miR-155 induction by both poly (I:C) and TNF-α in a dose-dependent manner. FIGS. 9A-9B, 10. As a control, the ERK inhibitor uo126 did not reduce poly (I:C) induction of miR-155 (data not shown).

These data indicate that the JNK pathway is involved in the up-regulation of miR-155 expression in response to poly (I:C) or TNF-α.

Example 7

LPS Induces Bone Marrow Expression of miR155 In Vivo

To confirm the in vitro effects observed in Examples 1-6, the following experiments were conducted to determine whether miR-155 expression is elevated in the bone marrow compartment after the onset of inflammation in vivo.

In the experiments described in the Examples below, wild-type (WT) C57Bl6 mice purchased from The Jackson Laboratory were used. Rag1$^{-/-}$ mice were bred in house. All experiments involved female mice and were performed according to IACUC-approved protocols.

Figure 11:
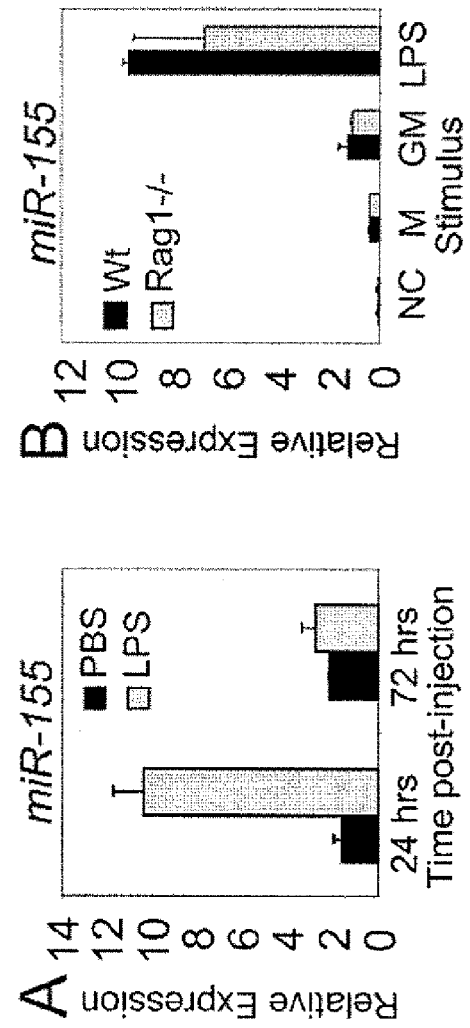
FIG. 11A is a graph showing the relative expression of miR-155 in bone marrow cells of wild-type mice injected with either phosphate buffered saline (PBS) or LPS, at 24 and 72 hours post-injection, as measured by quantitative PCR.
FIG. 11B is a graph showing the relative expression of miR-155 in bone marrow cells from wild-type or Rag1$^{-/-}$ mice, following in vitro stimulation with LPS, GM-CSF (GM), or medium (M), as measured by quantitative PCR.

WT mice were injected i.p. with either 50 μg LPS (Sigma-Aldrich) in phosphate buffered saline (PBS), or with PBS alone. Bone marrow cells were harvested at 24 hours or 72 hours post-treatment as described in Example 1. RNA was isolated from total bone marrow cells as described in Example 1, and analyzed for miR-155 expression using qPCR as described in Example 1. The data are shown in FIG. 11A. miR-155 was strongly induced in bone marrow cells 24 hours after LPS treatment, and returned to control levels by 72 hours post-treatment.

To determine whether up-regulation of miR-155 expression in isolated bone marrow cells by LPS or GM-CSF stimulation was attributable to cells other than mature B and T lymphocytes, miR-155 expression in bone marrow cells isolated from either WT or Rag1$^{-/-}$ mice was measured, following stimulation with culture medium, LPS, or GM-CSF. WT and Rag1$^{-/-}$ mice were injected with 100 ng/ml LPS (Sigma Aldrich), 100 ng/ml GM-CSF (GM) (eBioscience), or culture medium (M), as described in Example 1. Bone marrow was flushed out of the femurs and tibias of WT and Rag1$^{-/-}$ mice (n=3 per group) 24 hours after stimulation, and RNA was isolated from the total bone marrow cells as described in Example 1. qPCR was performed to determine the levels of miR-155 expression as described in Example 1. The data are presented in FIG. 11B. NC corresponds to no template control for the qPCR reaction. Up-regulation of miR-155 expression was detected upon LPS and GM-CSF stimulation in bone marrow cells from both WT and Rag1$^{-/-}$ mice, demonstrating that cells other than mature B and T lymphocytes contribute to this response.

Example 8

LPS Induces Expansion of GM Cells, Reduction in B Cells, and Reduction in Erythroid Precursors The following experiments were conducted to determine whether LPS affects bone marrow cell dynamics in vivo.

Figure 12:
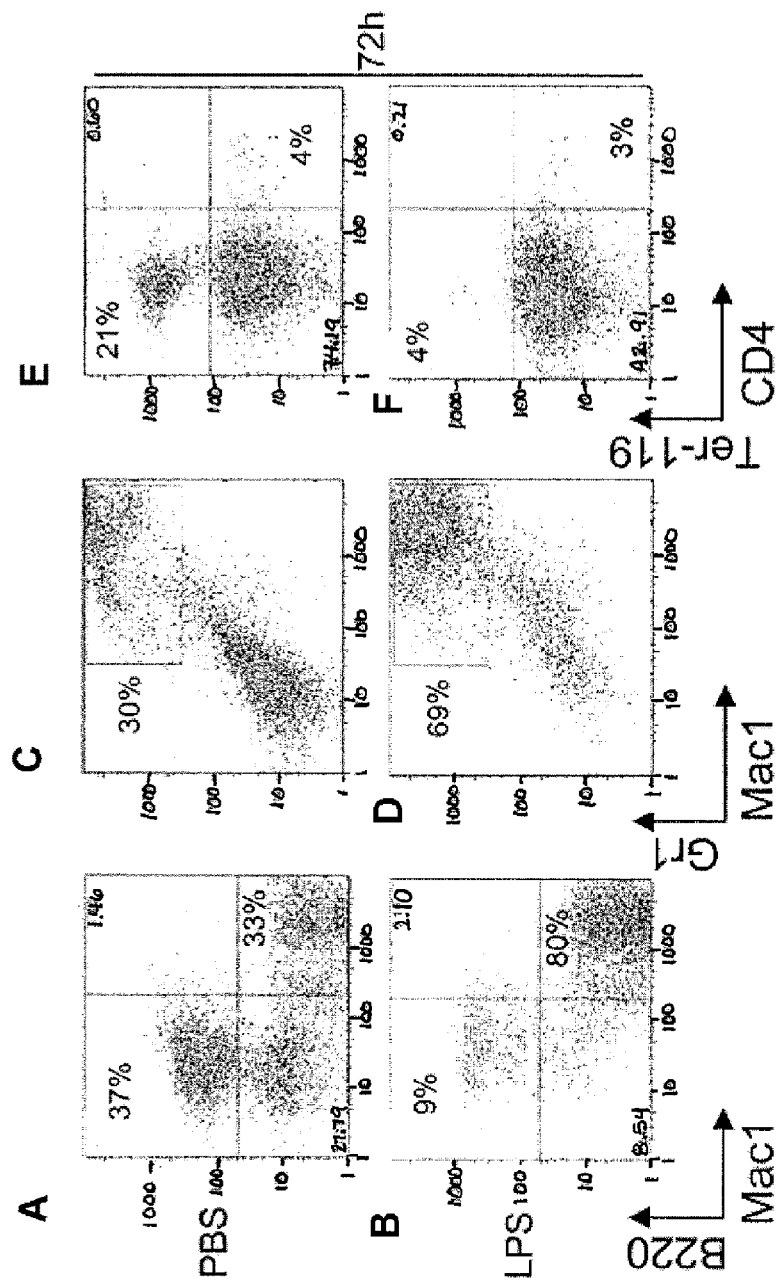
FIGS. 12A-12F are plots of fluorescence activated cell sorting (FACS).
Figure 13:
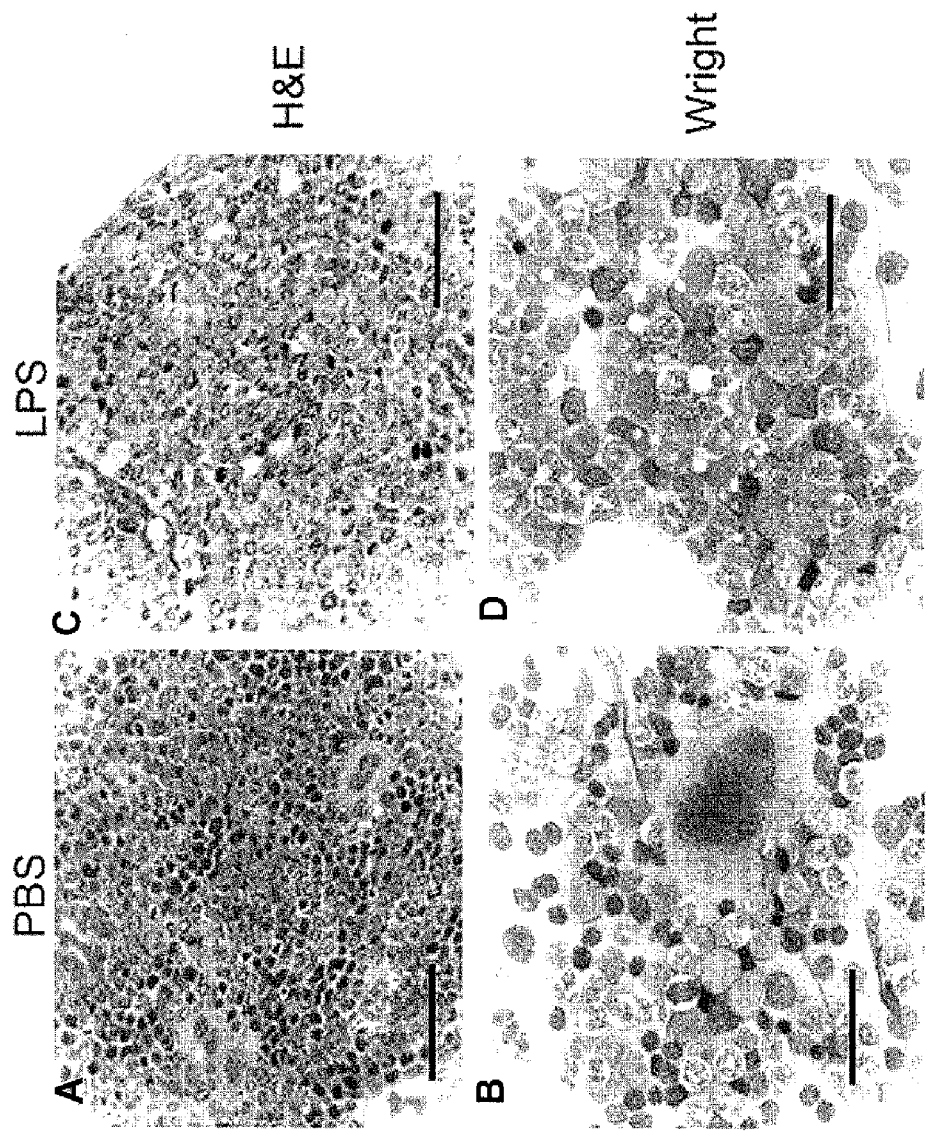
FIGS. 13A-13D are photographs of bone marrow cells isolated from mice injected with PBS and stained with hematoxylin and eosin (H&E)(FIG. 13A) or Wright's stain (FIG. 13B), or of bone marrow cells isolated from mice injected with LPS and stained with H&E (FIG. 13C) or Wright's stain (FIG. 13D).

WT mice were injected i.p. with either PBS or 50 μg/mL LPS dissolved in PBS. 72 hours post-injection, bone marrow cells were isolated from the mice. Fluorophor-conjugated monoclonal antibodies specific for Mac1, Gr1, Ter-199, B220 and CD4 (eBioscience, San Diego, Calif.) were used in various combinations to stain bone marrow cells that were fixed after washing using paraformaldehyde (1% final). Stained cells were assayed using a BD FACSCalibur® flow cytometer (Becton Dickenson, Franklin Lakes, N.J.) and further analyzed with FloJo® FACS analysis software (Becton Disckenson, Franklin Lakes, N.J.). The FACS data are presented in FIGS. 12A-12F. The percentage of GM cells (expressing Mac1 and Gr1 surface markers) was substantially increased 72 hours post-injection with LPS, as compared to PBS-injected control mice. FIGS. 12A-12B. By contrast, there was a substantial reduction in the percentage of B cells (expressing the cell surface marker B220) 72 hours post-injection with LPS, compared to PBS-injected control mice. FIGS. 12C-12D. Similarly, there was a substantial reduction in the percentage of erythroid precursor cells (expressing the cell surface marker Ter-119) 72 hours post-injection with LPS, compared to PBS-injected control mice. FIGS. 12E-12F.

Bone marrow cells isolated from WT mice injected with PBS or 50 μg/mL LPS dissolved in PBS 72 hours post-injection, as described above, were stained with Wright's stain (Wright) or hematoxylin and eosin (H&E) stains using routine protocols. The results are shown in FIGS. 13A-13D. The micro-photographs of bone marrow from LPS-treated mice showed myeloid preponderance and hyperplasia, with relative erythroid hyperplasia.

These data, along with the data showing maximal induction of miR-155 expression at 24 hours post-LPS treatment (Example 7), indicate that LPS-induced miR-155 expression in the bone marrow precedes GM cell expansion.

Example 9

Forced Expression of miR-155 in HSC's Causes Myeloproliferative Disorder in Bone Marrow The following experiments were conducted to determine whether miR-155 is sufficient to mediate GM expansion in vivo in mouse bone marrow.

To generate vectors for expression miR-155, an miR-155 expression cassette containing the human miR-155 hairpin sequence and flanking regions was cloned from a cDNA library into pcDNA3 as described in E is, P. S., et al. (2005) *Proc. Natl. Acad. Sci. USA* 102:3627-3632, herein expressly incorporated by reference in its entirety. The cassette was subcloned into pMSCVpuro (Clonetech, Mountainview, Calif.), FUW (Lois et al., (2002) *Science* 295:868-872), or pMG (Invivogen, San Diego, Calif.), using routine molecular cloning techniques. pMG155 is a modified pMSCV vector whereby GFP was placed downstream from the 5'LTR, and the miR-155 expression cassette was cloned downstream from the GFP stop codon using routine cloning techniques.

Figure 14:
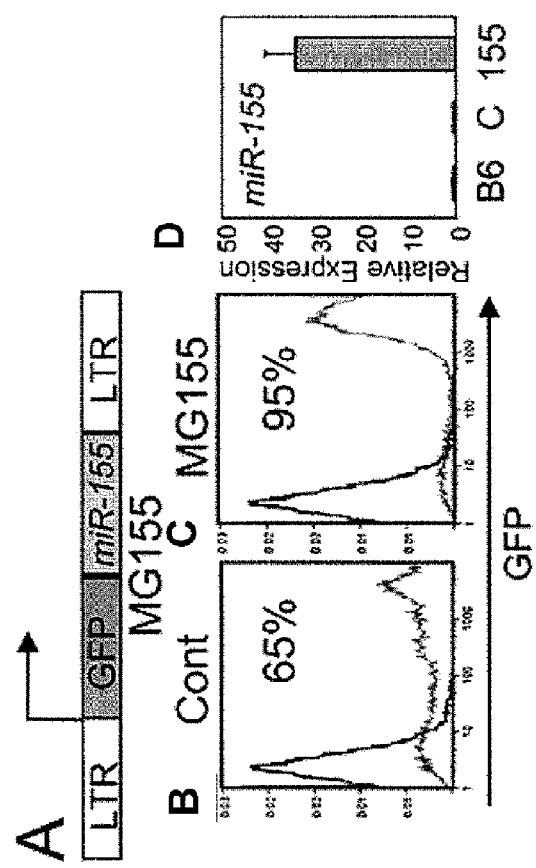
FIG. 14A is a graphical representation (not to scale) of the expression vector used to transform hematopoietic stem cells (HSC's) to induce expression of an miR-155-GFP fusion protein, MG155.
FIGS. 14B-14C are plots of fluorescence activated cell sorting (FACS).
FIG. 14D is a graph showing the expression of MG155 in the bone marrow of mice reconstituted with MG155, or a control vector, as measured by FACS. B6 corresponds to untreated mice, C corresponds to mice reconstituted with HSC's transformed with the control vector, and MG155 corresponds to mice reconstituted with the MG155 transformed HSC's.

FIG. 14A is graphical depiction (not to scale) of the retroviral construct used to enable both mir-155 and GFP expression in HSCs.

HSC-enriched bone marrow cells were obtained by injecting mice i.p. with 5 μg 5-fluorouracil for 5 days before bone marrow harvest, as described in Yang et al. (2005) *Proc. Nat. Acad. Sci. USA* 102:4518-4523, the contents of which is herein expressly incorporated by reference in its entirety. Cells were collected from the bone marrow, and RBCs were removed using an RBC lysis solution (Invitrogen, Carlsbad, Calif.) as described in Example 1. Cells were cultured for 24 h. in 20 ng/ml IL-3, 50 ng/ml IL-6, and 50 ng/ml SCF (all from eBioscience, San Diego, Calif.) containing complete RPMI (10% FBS, 100 U/ml penicillin, 100 U/ml streptomycin and 50 μM β-mercaptoethanol) before initial retroviral infection. To generate retroviurses for infecting HSC-enriched bone marrow cells, 293T cells were transfected with pMG155 and pCL-Eco (Imgenex, San Diego, Calif.) using a standard calcium phosphate protocol. After 48 h, 8 μg/ml polybrene was added to culture supernatant-containing retroviruses. The culture supernatant was used to spin-infect $10^6$ HSC-enriched cells per donor for 1.5 h at 2,500 RPM and 30° C. This procedure was repeated three times once daily, followed by injection of $10^6$ retrovirally infected HSC-enriched cells per lethally irradiated (1,100 rads from Cesium 137 source at 50 rads/minute) recipient mice. Recipient mice were maintained on Septra throughout the reconstitution period.

Two months after reconstitution, mice were sacrificed. Bone marrow, thymus, spleen and lymph nodes were analyzed for GFP and miR-155 co-expression. Bone marrow was isolated as described in Example 1. A portion of the bone marrow was analyzed by FACs, as described in Example 1, to assess GFP-expression. The FACS data are presented in FIGS. 14B and 14C. The percentage of GFP bone marrow cells of mice reconstituted with control vector (Cont, FIG. 14B) and MG155 vector (MG155, FIG. 14C) is indicated. Total RNA was isolated from whole bone marrow and used to generate cDNA for quantitative PCR as described in Example 1. miR-155 RNA levels were measured as described in Example 1. The data are presented in FIG. 14D. The data show that control mice, or mice injected with the GFP control vector did not show detectable levels of miR-155. By contrast, miR-155 expression was detected in cells isolated from mice reconstituted with HSC's transfected with the MG155 vector.

Figure 15:
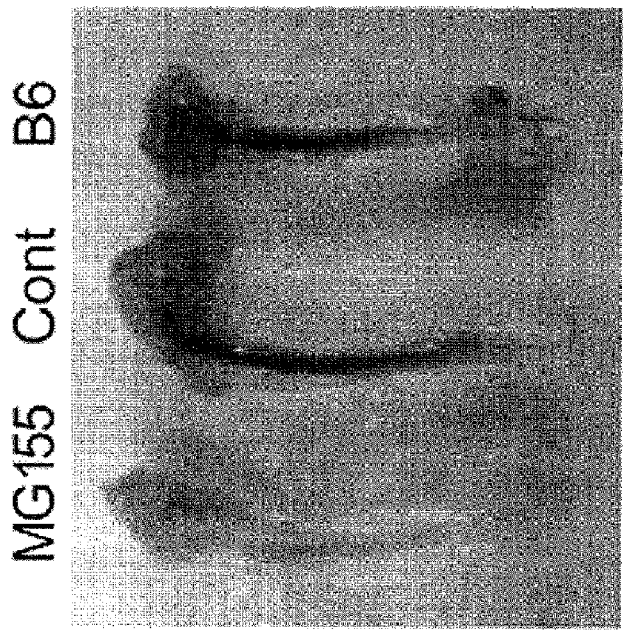
FIG. 15 is a photograph showing the tibias from mice reconstituted with HSC's transformed with MG155 (MG155) or control vector (Cont), two months following reconstitution, compared to untreated mice (B6).

Tibias and femurs were removed from mice reconstituted with MG155 or control vector HSCs for two months, or untreated C57BL6 control (B6) mice. FIG. 15 is a photograph of an exemplary tibia from each group of mice. Mice expressing miR-155 exhibited white-tan bone marrow coloration, whereas the control mice exhibited vibrant red bone marrow coloration.

Figure 16:
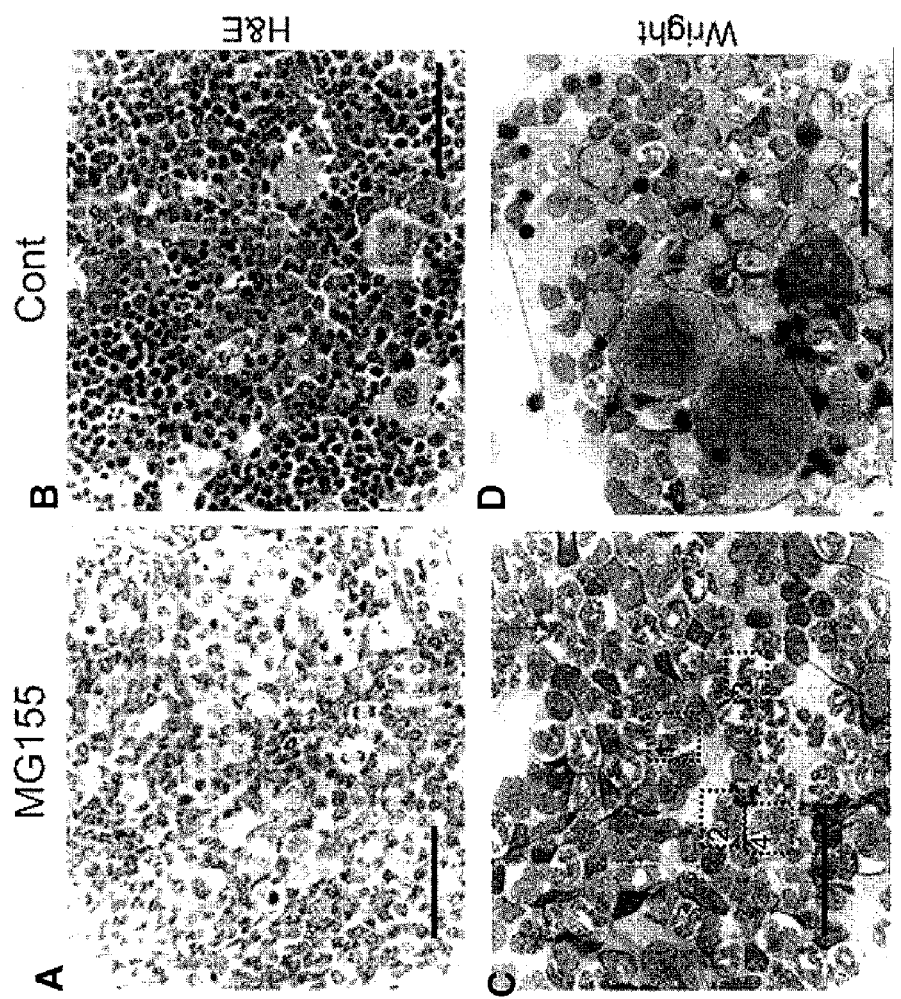
FIGS. 16A-16D are photographs of Hematoxylin and Eosin stained bone marrow sections from mice reconstituted with miR-155 expressing HSC's (FIG. 16A) compared to control mice (FIG. 16B); and Wright's stained bone marrow sections from mice reconstituted with miR-155 expressing HSC's (FIG. 16C) compared to control mice (FIG. 16D).
Figure 17:
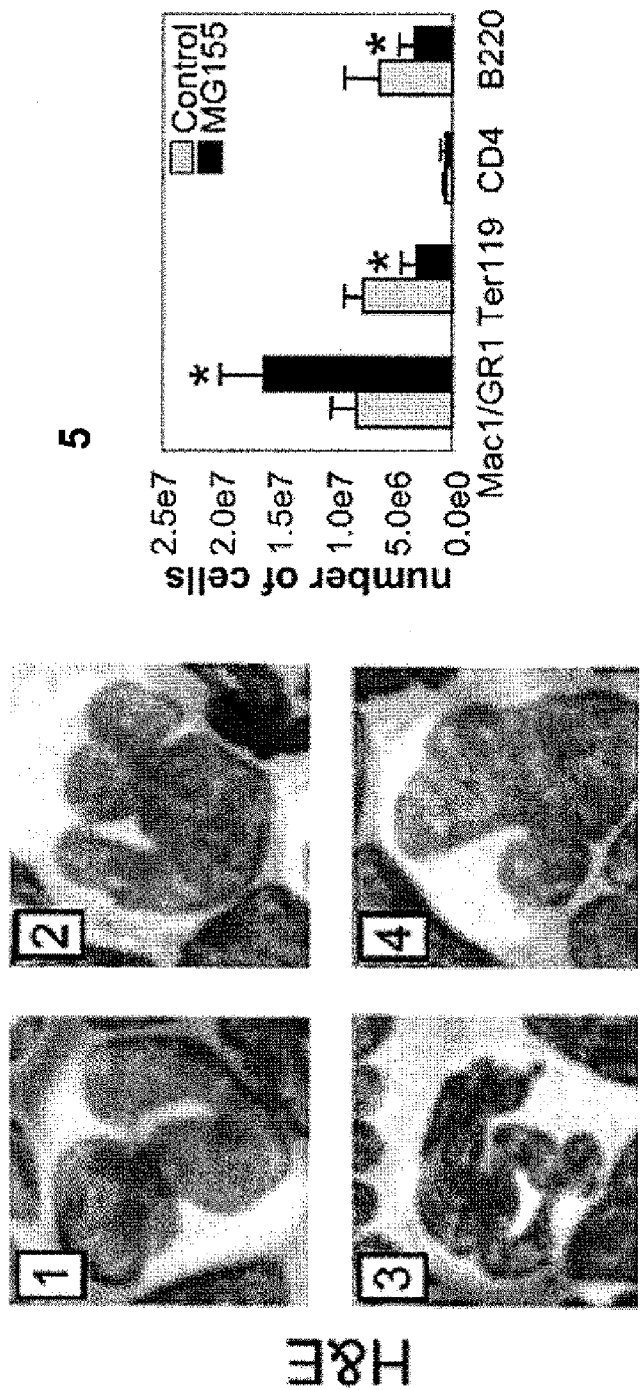
FIG. 17(1)-17(4) are photographs of dysplastic myeloid cells observed in miR-155-expressing bone marrow.

Bone marrow smears were prepared from extracted bone marrow of mice reconstituted with HSC's transfected with the control vector or the MG155 vector. The preparation was air-dried and stained with Hematoxylin & Eosin (H&E) (FIGS. 16A-16B) or Wright's stain (FIGS. 16C-16D). The preparations were examined on an Olympus BX-511 microscope and photographed using a Spot Digital Camera and software. The morphology of the bone marrow cells revealed that miR-155 expressing bone marrow was dominated by GM cells at a variety of either normal or abnormal developmental stages. Bone marrow of mice reconstituted with miR-155 expressing HSC's also exhibited a reduction in erythrocytes, megakaryocytes, and lymphocytes. FIGS. 17A-17E are photographs showing an enlarged view of examples of dysplastic myeloid cells in miR-155 expressing bone marrow (enlargement of indicated sections of FIG. 16C). Many of the cells that appeared to be granulocytic precursors showed irregular segmentation of the nuclei and lacked condensation of nuclear chromatin.

Figure 18:
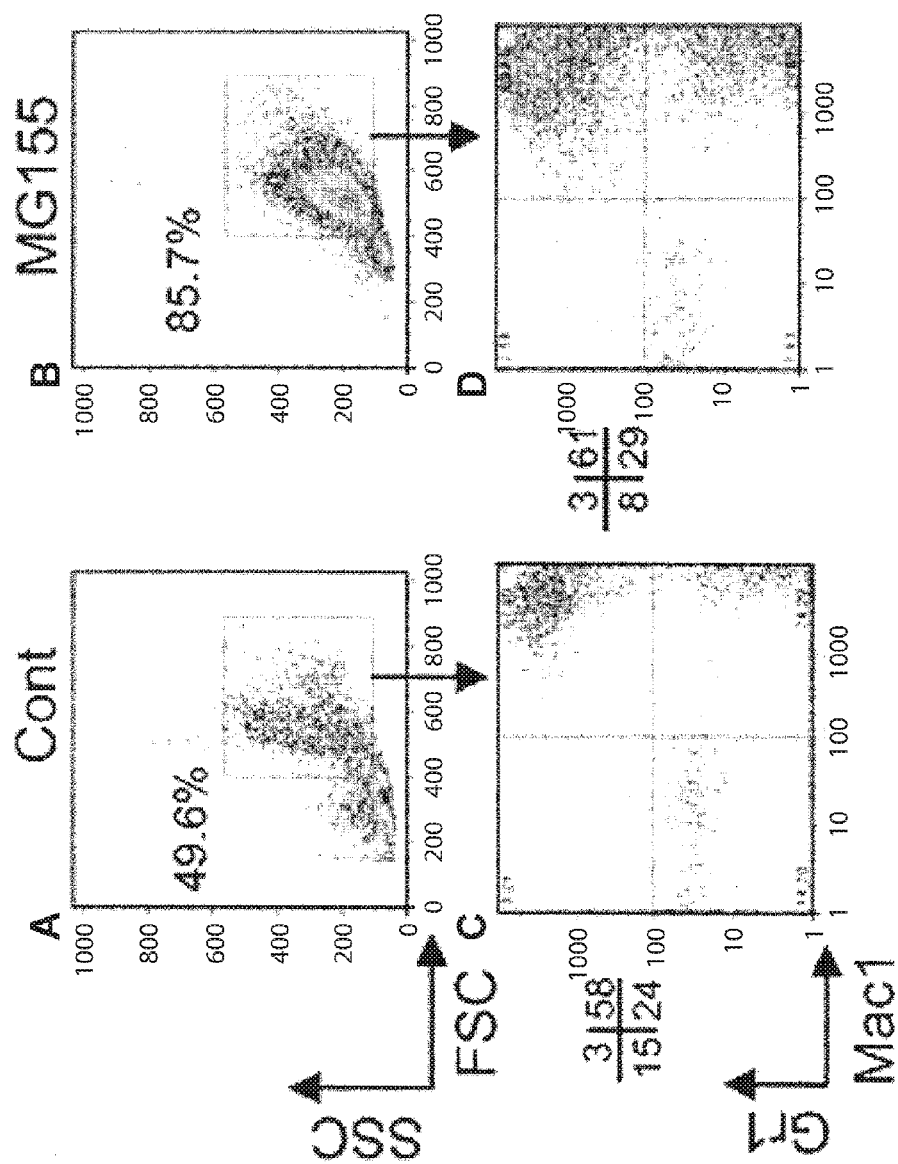
FIGS. 18A-18D are plots showing the distribution of GFP-gated cells expressing SSC and FSC cell surface markers in control mice (FIG. 18A) or mice reconstituted with MG155 HSC's (FIG. 18B); and the distribution of cells expressing Gr1 and Mac1 cell surface markers in control mice (FIG. 18C) or mice reconstituted with MG155 HSC's (FIG. 18D).

A portion of the bone marrow isolated from mice reconstituted with HSC's transfected with the control vector or MG155 vector was depleted of RBC's as described in Example 1. The cells were treated with fluorophor-conjugated Mac1, Gr1, Ter-119, B220 and CD4 monoclonal antibodies as described in Example 1. The cell preparations were analyzed by FACS, as described in Example 1. The number of Mac1/Gr1, Ter-119, CD4, and B220 expressing bone marrow cells is graphically represented in FIG. 18. The bone marrow of MG155-reconstituted mice contained approximately twice as many Mac1/Gr1-expressing cells, very few Ter-119+ erythroid precursors, and a reduction in B220+ B cells as compared to the control vector.

Figure 19:
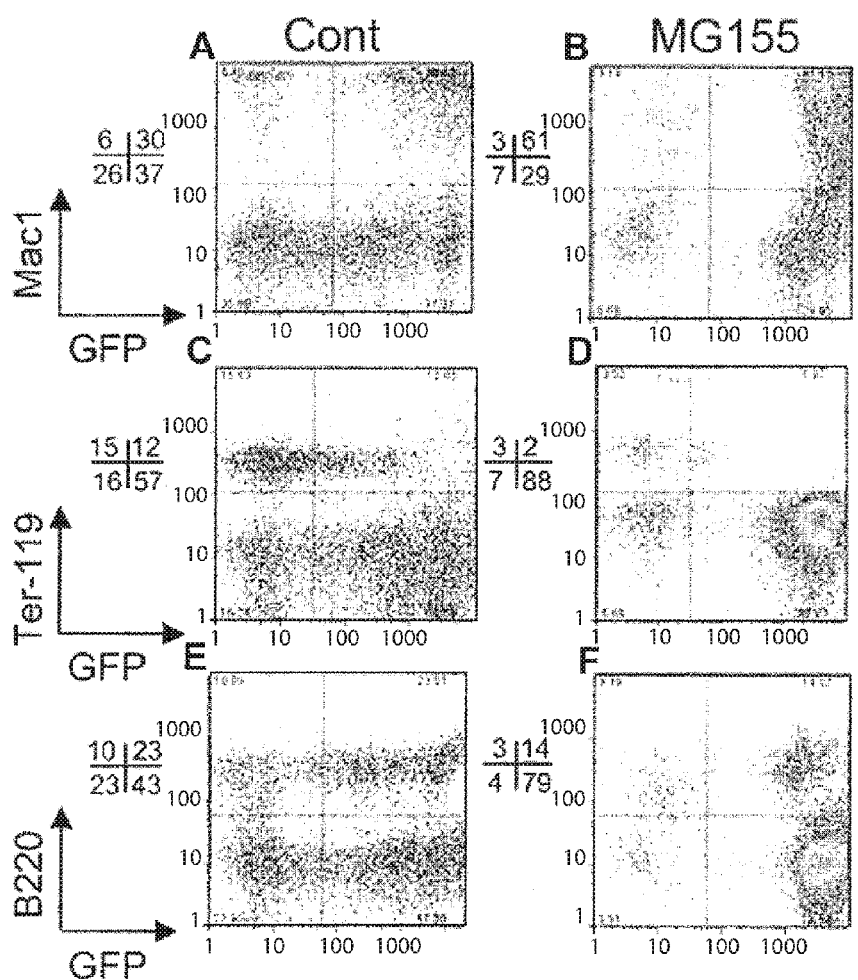
FIGS. 19A-19F are FACS plots showing the distribution of bone marrow cells from mice reconstituted with HSC's transformed with MG155 or control vector. Shown is the distribution of cells expressing Mac1 (FIGS. 19A, 19B), Ter-119 (FIGS. 19C, 19D), and B220 (FIGS. 19E, 19F) on both GFP$^+$ and GFP$^-$ cells.
Figure 20:
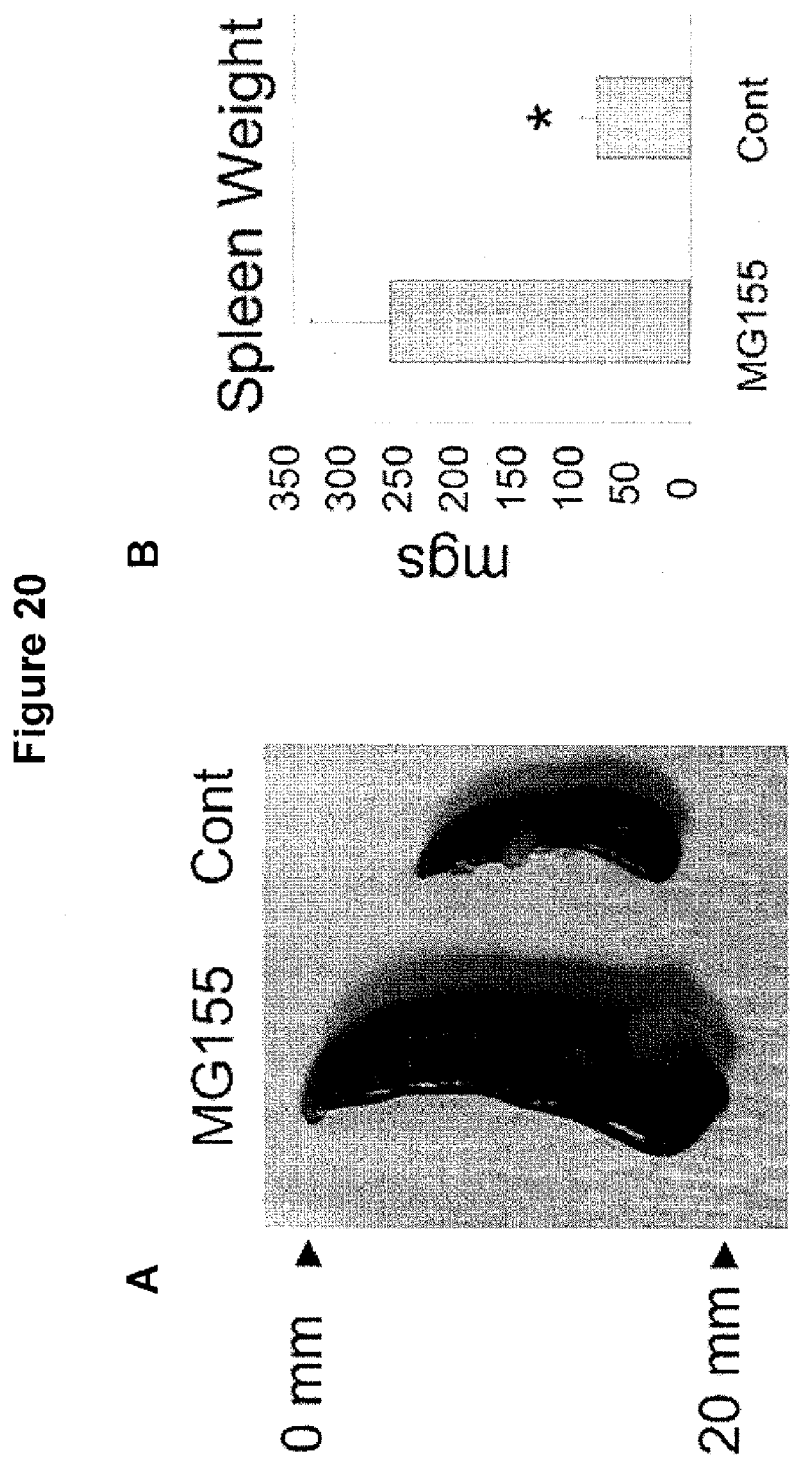
FIG. 20A is a photograph of a spleen removed from mice reconstituted with HSC's transformed with MG155 or control vector, two months after reconstitution.
FIG. 20B is a bar graph of the average spleen weight of mice reconstituted with HSC's transformed with MG155 or control vector two months after reconstitution.

GFP$^+$-gated bone marrow cells from mice reconstituted with MG155 or control vector HSCs were analyzed for FSC and SSC counts and expression of Mac1 and Gr1. FIGS. 19A-19D are plots of the FACS data. GFP$^+$ cells expressing miR-155 showed a dramatic increase in large granular cells, as defined by having high forward scatter (FSC) and side scatter (SSC) (FIGS. 19A-19B). Back-gating was used to confirm that these cells were Mac1$^+$, with a majority also positive for Gr1 (FIGS. 19C-19D). FIGS. 20A-20F are plots of FACS of the bone marrow. The cells responsible for the overall GM, B, and erythroid precursor differences between MG155 and control vector cells were largely GFP$^+$.

The data above demonstrate that expression of miR-155 in bone marrow cells leads to profound myeloid proliferation with dysplastic changes, when compared with controls.

Example 10

Forced Expression of miR-155 in HSC's Causes Splenomegaly and Extramedullary Hematopoiesis The following experiments were conducted to assess the effect of forced miR-155 expression in HSC's on the morphology and cellular constitution of spleens.

Generation of HSC's stably transformed with either a GFP (control) or miR-155/GFP expression (MG155) vector is described in Example 9. Reconstitution of lethally-irradiated mice with transformed HSC's is described in Example 9.

Figure 21:
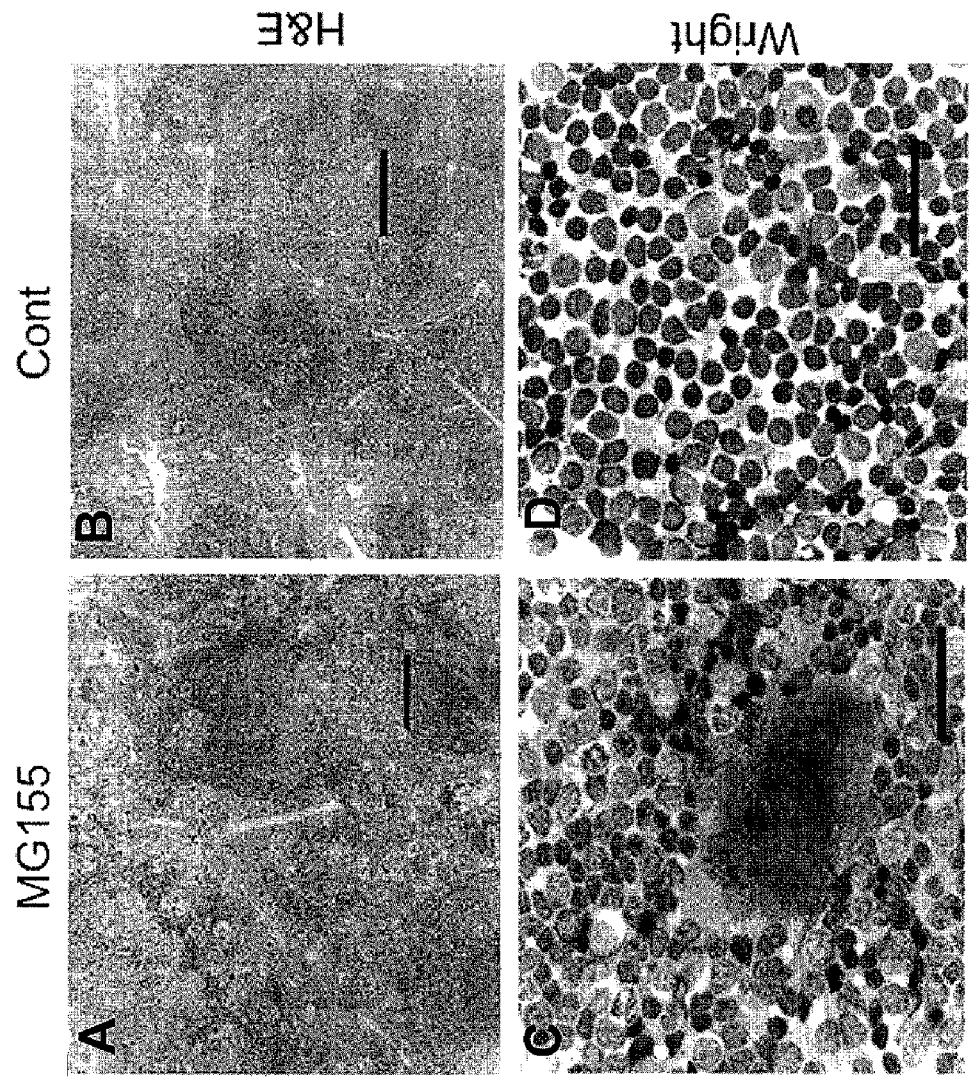
FIGS. 21A-21D are photographs of hematoxylin & eosin (H&E) stained sections (FIGS. 21A, 21B) or Wright's stained sections (FIGS. 21C, 21D) from spleens of mice reconstituted with HSC's transformed with MG155 or control vector. The bar indicates 25 µm.

Two months after reconstitution, spleens were removed from the mice and photographed. Splenomegaly was observed in the mice reconstituted with miR-155-expressing HSC's. Mice reconstituted with HSC's transformed with control vector were normal. FIG. 21.

Figure 22:
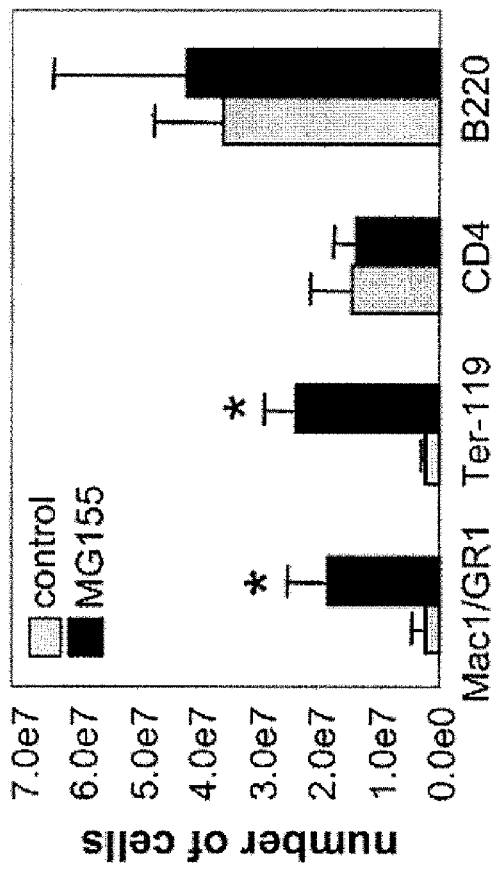
FIG. 22 is a bar graph of the average number of cells expressing Mac1/GR1, Ter-199, CD4 and B220 cell surface markers in mice reconstituted with HSC's transformed with MG155 or control vector.

Spleens were placed into 10% neutral-buffered formalin immediately after necropsy, fixed for 12-18 hours, washed and transferred to 70% ethanol, and embedded in paraffin using standard protocols. Spleens were sectioned and stained with hematoxylin & eosin (H&E) (FIGS. 22A-22B) or Wright's stain (FIGS. 22C-22D). H&E staining revealed expanded interfollicular regions containing various hematopoietic elements, as well as constricted and disrupted B cell follicles compared with control spleens. Wright's staining revealed a large number of erythroid precursors, megakaryocytes, and some developing GM cells in the spleens of mice reconstituted with miR-155 expressing HSC's, whereas very few of these cell types were observed in control spleens.

Figure 23:
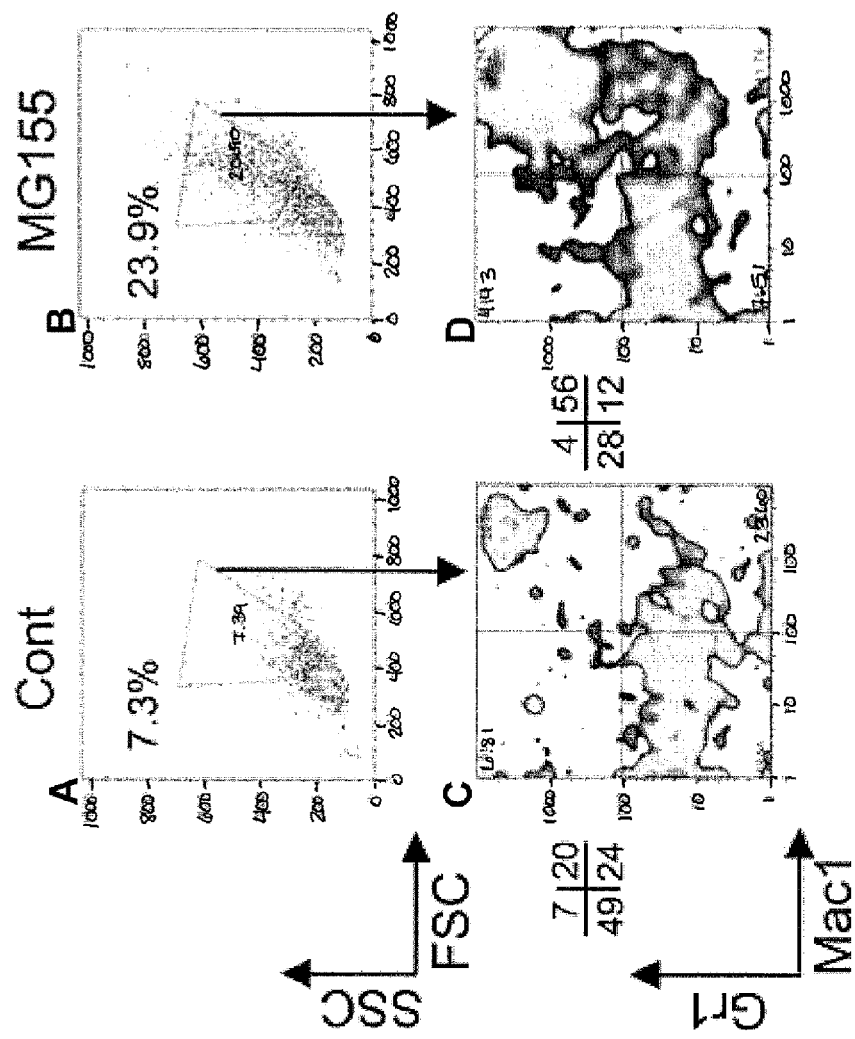
FIGS. 23A-23D are plots showing the cell distribution of GFP-gated spleen cells from mice reconstituted with MG155 (FIGS. 23B, 23D) or control vector HSC's (FIGS. 23A, 23C), assessing SSC and FSC, or Gr1/Mac1 cell surface markers, as measured by FACS.

Splenocytes were also analyzed by FACS to determine cell type and expression of cell surface markers, as described in Example 9. The numbers of Mac1/Gr1, Ter-119, CD4 and B220 expressing splenocytes from mice reconstituted with HSC's expressing GFP alone (control), or HSC's expressing MG155 are indicated in FIG. 23. As expected, the spleens from mice reconstituted with MG155 HSC's had elevated numbers of Mac1+/Gr1+myeloid cells and Ter-119+ erythroid cells, with little change in CD4+ T cells and B220+ B cells.

Figure 24:
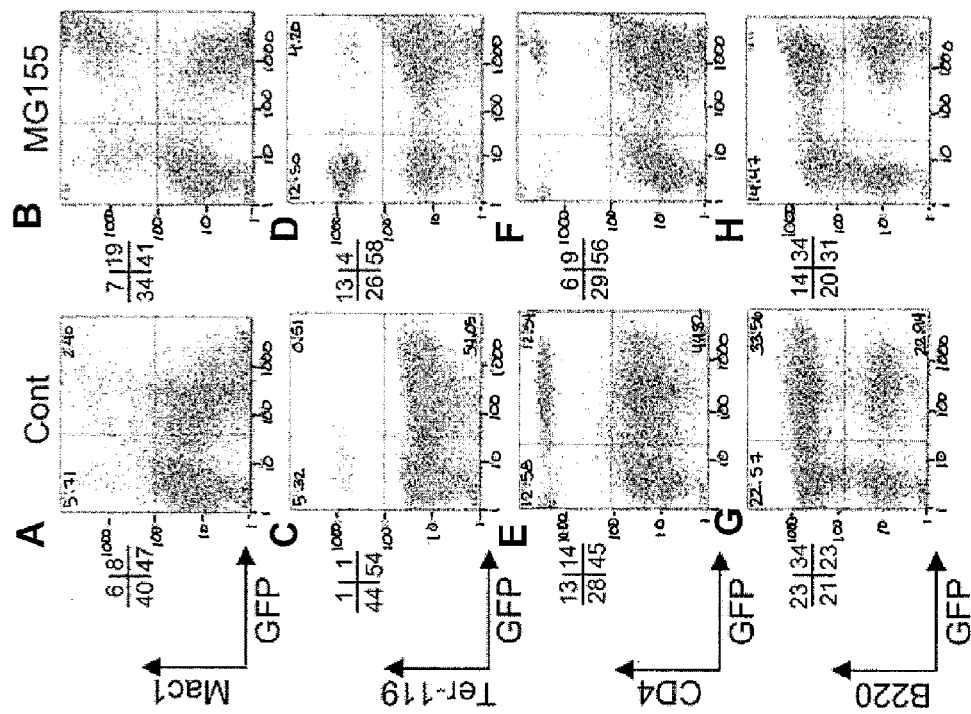
FIGS. 24A-24H are plots showing the distribution of both GFP+ and GFP− splenocytes from mice reconstituted with control vector or MG155 HSC's. The plots show the distribution of cells expressing the cell surface markers Mac1 (FIGS. 24A, 24B), Ter-119 (FIGS. 24C, 24D), CD4 (FIGS. 24E, 24F), and B220 (FIGS. 24G, 24H).
Figure 25:
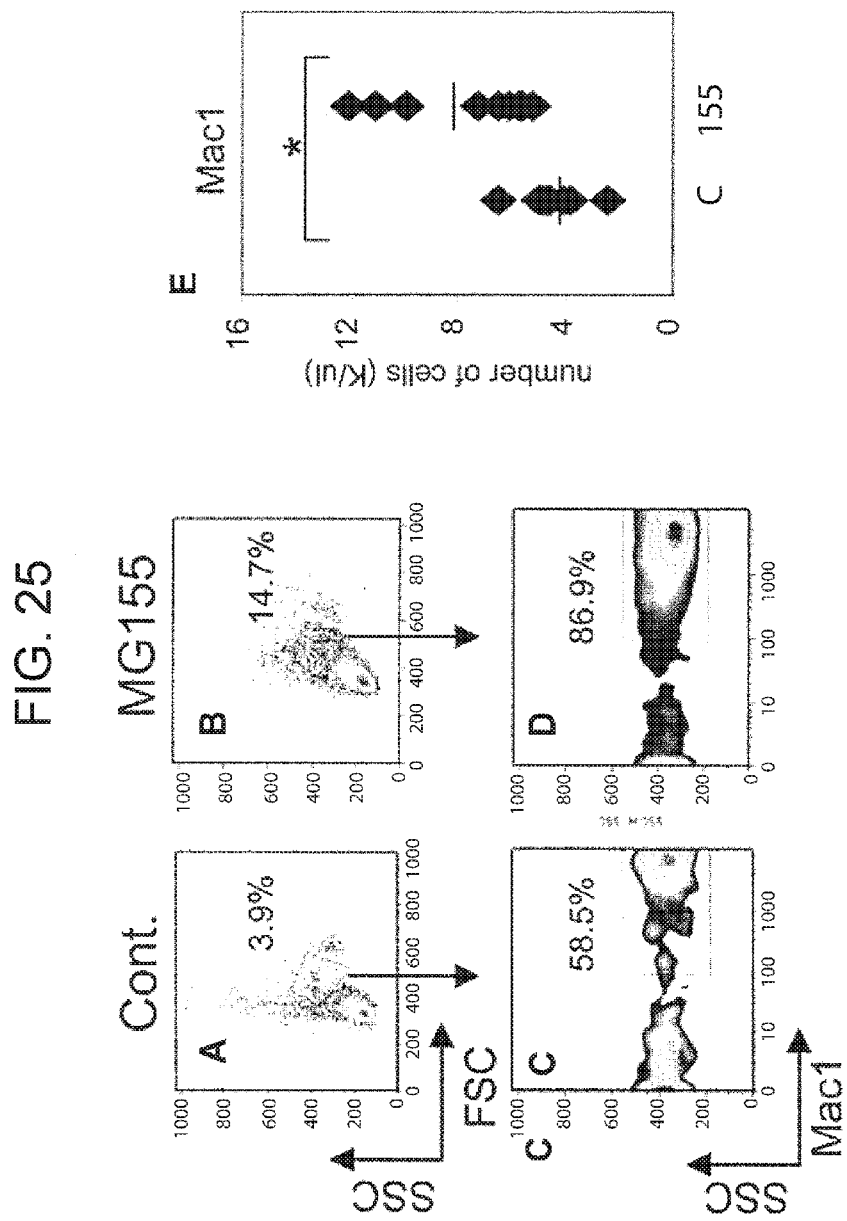
FIGS. 25A-25D are plots showing the distribution of peripheral blood cells expressing SSC, FSC, or SSC and Mac1, in mice reconstituted with control vector or MG155, two months after reconstitution.
FIG. 25E is a graph showing the total number of Mac1-expressing peripheral blood cells (K/µl)

GFP+-gated splenocytes from mice reconstituted with MG155 or control vector HSCs were analyzed for FSC and SSC counts and expression of Mac1 and Gr1. FIGS. 24A-24D are plots of the FACS data. GFP cells expressing miR-155 showed a dramatic increase in large granular cells, as defined by having high forward scatter (FSC) and side scatter (SSC) (FIGS. 24A-24B). Back-gating was used to confirm that these cells were Mac1+, with a majority also positive for Gr1 (FIGS. 24C-24D). FIGS. 25A-25H are plots of FACS of the splenocytes, determining the co-distribution of cells expressing Mac1 and GFP (FIGS. 25A-215B), Ter-119 and GFP (FIGS. 25C-25D), CD4 and GFP (FIGS. 25E-25F) and B220 and GFP (FIGS. 25G-25H). miR-155-expressing splenocytes contained overall higher numbers of Mac1+ cells, that expressed GFP compared with controls. Conversely, the Ter-119+ cell population of miR-155 expressing spleens was largely negative for GFP, possibly arising from non-transduced HSC's.

The data above demonstrate the presence of splenic extramedullary hematopoiesis in miR-155 expressing mice, likely compensating for the bone marrow defects in these mice.

Example 11

Forced Expression of miR-155 in HSC's Perturbs Peripheral Blood Cell Populations The following experiments were conducted to assess the effect of forced miR-155 expression in HSC's on the cellular constitution of peripheral blood.

Generation of HSC's stably transformed with either a GFP (control) or miR-155/GFP expression (MG155) vector is described in Example 10. Reconstitution of lethally-irradiated mice with transformed HSC's is described in Example 10.

Figure 26:
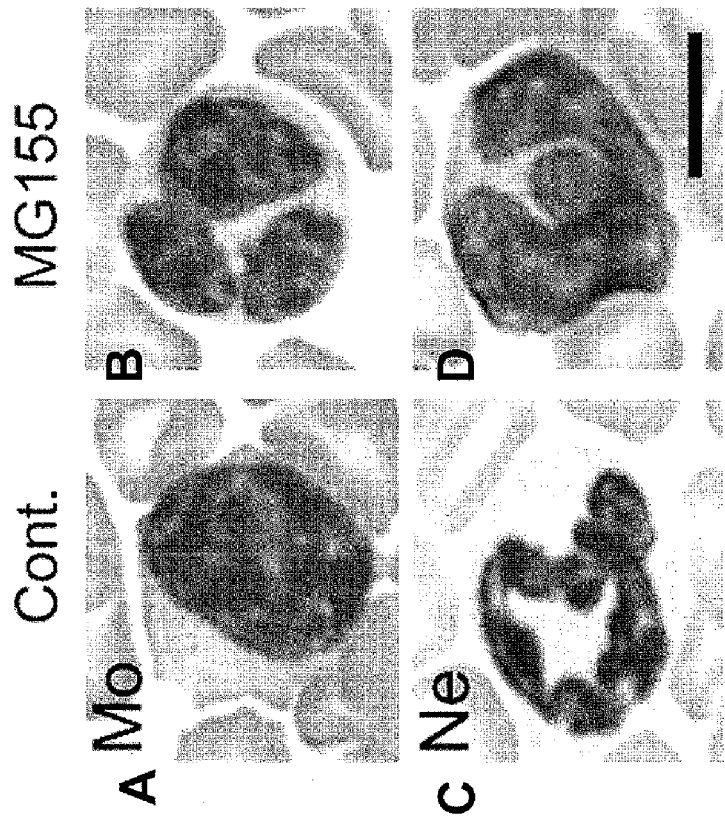
FIGS. 26A-26D are photomicrographs of a normal Wright's-stained monocyte (Mo) (FIG. 26A, 26B) and neutrophil (Ne) (FIG. 26C, FIG. 26D) from the blood of mice reconstituted with control vector HSC's or MG155 HSC's.

Peripheral blood was collected from mice reconstituted with MG155 or control vector HSC's for two months and analyzed by FACS to correlate GFP expression and FSC and SSC counts, as well as to determine the expression of Mac1 as described in Example 1. The data are presented in FIGS. 26A-26D. The total number of Mac1+ cells was also determined (FIG. 26E). By two months after reconstitution, there were significantly elevated numbers of Mac1+ cells in the peripheral blood of mice reconstituted with MG155, compared to mice reconstituted with control vector HSC's.

Figure 27:
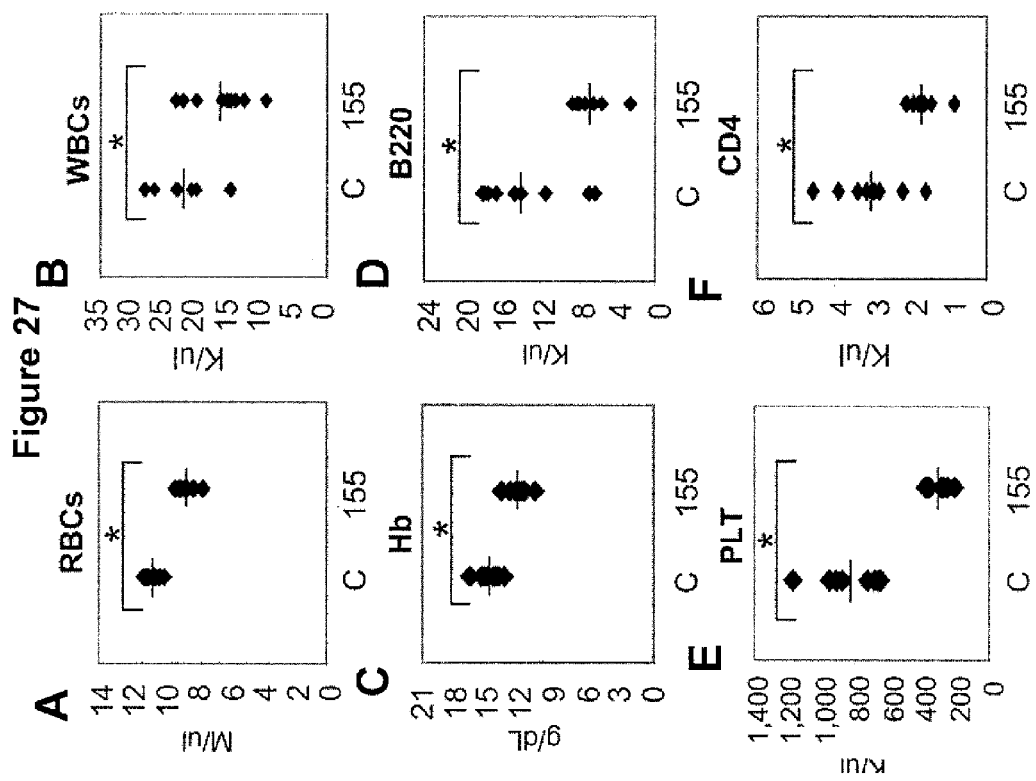
FIG. 27A-27F are graphs showing the levels of red blood cells (RBC's) (FIG. 27A), white blood cells (WBC's)(FIG. 27B), hemoglobin-expressing cells (Hb) (FIG. 27C), B220 B cells (B220)(FIG. 2D), platelet (PLT) (FIG. 27E), and CD4 T cell levels (FIG. 27F) in the blood of mice reconstituted with MG155 (155) or control vector (c) HSC's.
Figure 28A:
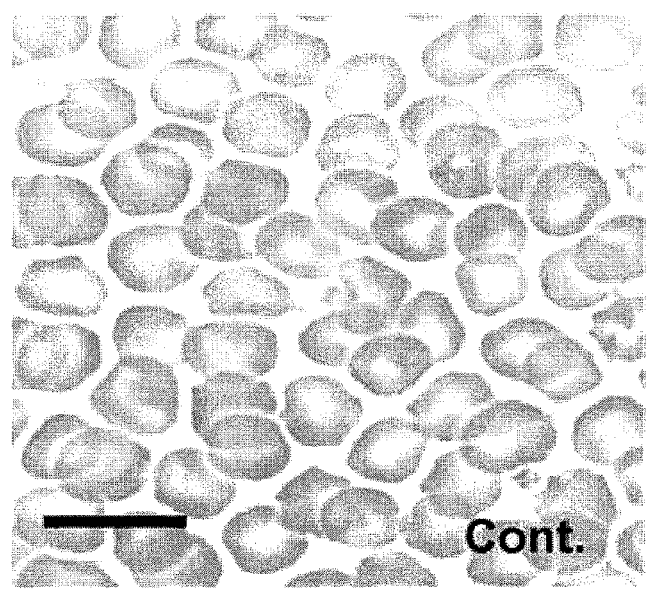
FIGS. 28A-28B are photographs of Wright-stained peripheral blood red blood cells from mice reconstituted with control vector (FIG. 28A) or MG155 (FIG. 28B) HSC's, two months after reconstitution. The bar represents 10 µm.
Figure 28B:
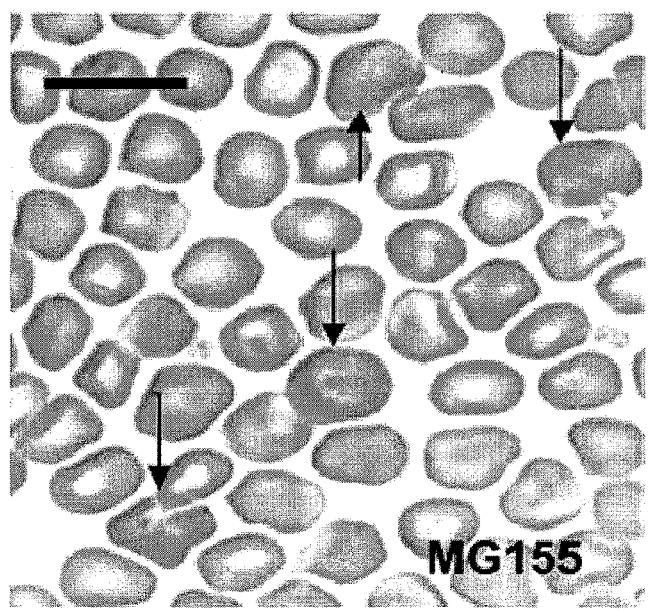
Figure 29:
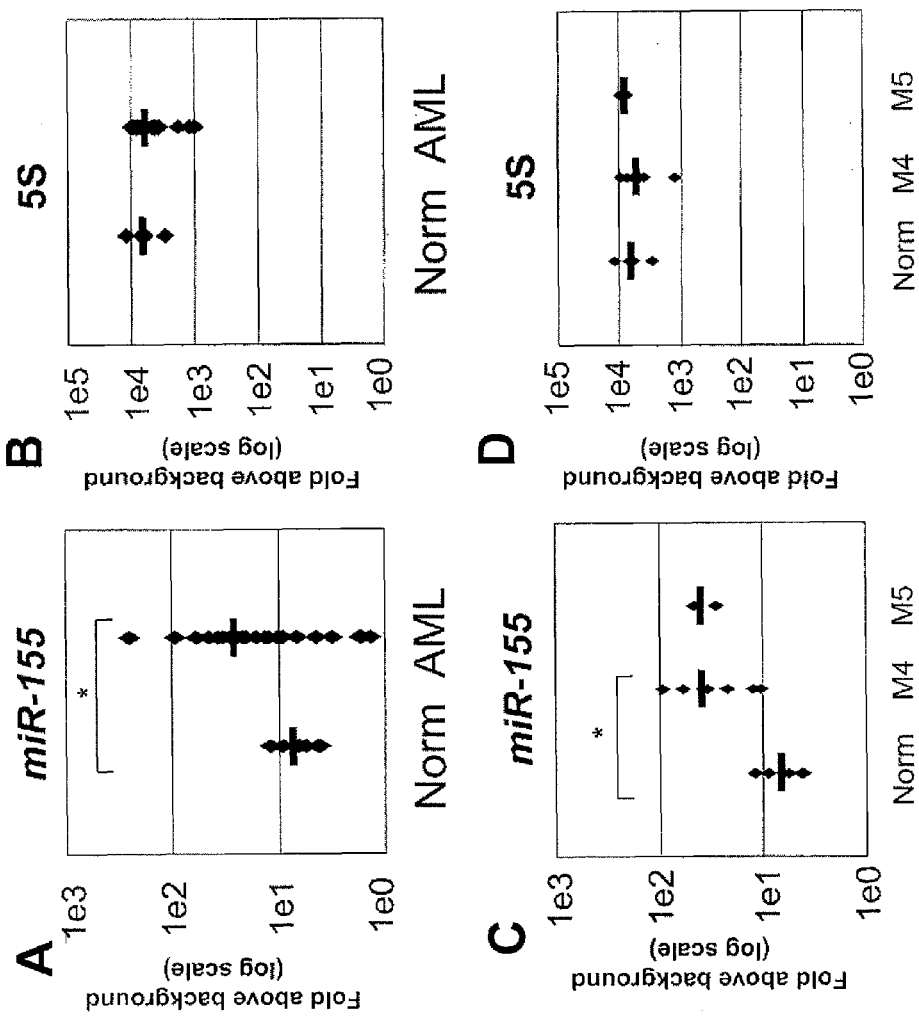
FIGS. 29A-29B are graphs showing the relative levels of miR-155RNA (FIG. 29A) and 5S RNA (FIG. 29B) in bone marrow cells of normal subjects (Norm) or subjects diagnosed with acute myeloid lymphoma (AML). Levels are expressed as fold above background (log scale).
FIGS. 29C-29D are graphs showing the relative levels of miR-155 RNA (FIG. 29C) and 5S RNA (FIG. 29D) in bone marrow cells of normal subjects (Norm) or subjects diagnosed with acute myeloid lymphoma of the FAB subtype M4 or M5.

Peripheral blood smears were prepared from the mice reconstituted with HSC's transfected with the control vector or the MG155 vector. The preparation was air-dried and stained with Wright's stain (FIGS. 27A-16D). The preparations were examined on an Olympus BX-511 microscope and photographed using a Spot Digital Camera and software. FIGS. 27A-27C are photographs of Wright-stained monocytes and neutrophils, respectively, from mice reconstituted with HSC's transfected with control vector. FIGS. 27C-27D are photographs of exemplary Wright-stained myeloid cells from mice reconstituted with HSC's transfected with MG155. The morphology of the peripheral blood cells of miR-155 expressing mice was abnormal. FIGS. 29A-29B are photographs of Wright-stained RBC's from mice reconstituted with HSC's transfected with the control vector (FIG. 29A), or HSC's transfected with the miR-155 expression vector (FIG. 29B). The photographs show several immature erythrocytes demonstrating polychormatophilia in miR-155 expressing animals. Data represent at least nine independent animals in each group, and p-values (*) of <0.05 were considered significant after a Student's two-tailed test.

Complete blood cell counts were performed on the blood of reconstituted mice. The data are presented in FIGS. 28A-28F. The cell counts revealed a significant reduction in red blood cell, hemoglobin and platelet levels in mice reconstituted with MG155-expressing HSC's compared to mice reconstituted with control vector HSC's.

Example 12

Human AML Patients have Increased miR-155 Expression

Several of the pathological features observed in miR-155 expressing mice are associated with human myeloid malignancies, including acute myeloid leukemia (AML). The following experiments were performed to assess miR-155 expression levels in the bone marrow of human AML patients compared to healthy patients.

Bone marrow samples from 24 AML patients and 6 healthy subjects were collected and flash frozen at −80° C. The samples were rapidly thawed. Total RNA was isolated from the bone marrow samples using a TRIzol® RNA purification kit (Invitrogen, Carlsbad, Calif.) according to the manufacturer's instructions. AML cases were categorized according to the WHO "Classification of Tumors" using anonymous clinical reports. The RNA was used in quantitative PCR (qPCR) to determine miR-155 and 5S expression levels as described in Example 1. FIGS. 29A-29B show the levels of miR-155 and 5S expression, respectively, in bone marrow from normal subjects and AML patients. Overall, on average, the AML samples significantly overexpressed miR-155 compared with healthy donors, with a level approximately 4.5 times higher. A few AML samples had miR-155 levels that were lower than the normal samples, whereas the overall AML sample distribution had a wide variance. In contrast, no significant difference in the average expression levels of 5S RNA was observed between the groups. FIGS. 29C-29D show the levels of miR-155 and 5S expression, respectively, in bone marrow from normal subjects, subjects with M4 AML, and subjects with M5 AML. Patients with acute myelomonocytic leukemia and acute monocytic leukemia, corresponding to FAB-AML-M4 and FAB-AML-M5, respectively, exhibited significant overepxession of miR-155 compared with normal samples.

The data above demonstrate that miR-155 expression in the bone marrow is significantly elevated in a subset of patients suffering from AML.

Example 13 miR-155 Directly Represses Genes Implicated in Hematopoietic Development and Disease The following experiments were conducted to identify miR-155 target genes that may be involved in the myeloproliferative phenotype observed in the experiments described above.

miR-155 expressing retroviruses were created as described in Example 9. RAW 264.7 cells were transduced with the MSCVpuro-155 or empty expression vector, or empty control vector, as described in Example 9. Briefly, to generate VsVgpseudotyped retroviruses containing the miR-155 expression cassette, $2\times10^6$ 293T cells were transfected with pMSCVpuro-miR-155, pGag-Pol and pVsVg using a standard calcium phosphate protocol. After 48 hours, viral supernatant was harvested and used to infect $5\times10^5$ RAW 264.7 cells for 8 h in the presence of polybrene at 10 μg/ml. After 48 h, stably transduced cells were selected using puromycin at 7 μg/ml for 7-10 days.

Total RNA was isolated using the RNeasy® mini RNA preparation kit (Qiagen, Valencia, Calif.), according to the manufacturer's instructions. The RNA was labeled and used to probe the Affymetrix Mouse Genome 430 2.0 microarray according to the protocols provided by the manufacturer (available at the website affymetrix.com/products/arrays/sepcific/mouse430_2.affx). Microarray data were analyzed using the Rosetta Resolver software and deposited in the GEO database under accession number GSE10467.

1,080 transcripts were down-regulated >1.2-fold with a p-value of <0.08. 89 of the repressed mRNA's contained conserved (human and mouse) miR-155 binding sites with 7- or 8-mer seeds in their 3/UTR's, according to published lists of computationally predicted target genes found on the Targetscan 4.0 website (See, Grimson, et al. (2007) *Mol. Cell.* 27:91-105; see also, Lewis et al. (2003) *Cell* 115:787-798, the entire contents of which are hereby expressly incorporated by reference in their entireties). Genes with reported roles in myeloid hyperplasia and/or hematopoiesis were identified through literature searching. The following genes were selected for further analysis, based on the microarray data, the presence of miR-155 binding sites, and the literature search: Bach1, Sla, Cutl1, Csflr, Jarid2, Cebpβ, PU.1, Arntl, Hif1α, and Picalm. To confirm the microarray results, quantitative PCR was performed on the RNA from the transduced cells using the gene-specific primers listed in Table A.

TABLE A

PRIMER SEQUENCES USED FOR QUANTITATIVE PCR

| Primer Name | Sequence | SEQ ID NO: |
|---|---|---|
| Bach1 F | TGAGTGAGAGTGCGGTATTTGC | 3 |
| Bach1 R | GTCAGTCTGGCCTACGATTCT | 4 |
| Sla F | ATGGGGAATAGCATGAAATCAC | 5 |
| Sla R | GGAGATGGGTAGTCAGTCAGC | 6 |
| Cutl1 F | CGCAGAGAACTGTTCATTGAGG | 7 |
| Cutl1 R | GAGCTGAAGGTGAGTCGCT | 8 |
| Csflr F | TGTCATGCAGCCTAGTGGC | 9 |
| Csflr R | CGGGAGATTCAGGGTCCAAG | 10 |
| Jarid2 F | GAAGGCGGTAAATGGGCTTCT | 11 |
| Jarid2 R | TCGTTGCTAGTAGAGGACACTT | 12 |
| Cebpβ F | GACAAGCACAGCGACGAGTA | 13 |
| Cebpβ R | AGCTGCTCCACCTTCTTCTG | 14 |
| PU.1 F | ATGTTACAGGCGTGCAAAATGG | 15 |
| PU.1 R | TGATCGCTATGGCTTTCTCCA | 16 |
| Arntl F | ACCACAGGAACTTCTAGGTACAT | 17 |
| Arntl R | GGACATTGGCTAAAACAACAGTG | 18 |

TABLE A-continued

PRIMER SEQUENCES USED FOR QUANTITATIVE PCR

| Primer Name | Sequence | SEQ ID NO: |
|---|---|---|
| Hif1a F | ACCTTCATCGGAAACTCCAAAG | 19 |
| Hif1a R | ACTGTTAGGCTCAGGTGAACT | 20 |
| Picalm F | GTCTGTCCACGCCATGTCG | 21 |
| Picalm R | TAGCAGAGAAAGGATCTCCCC | 22 |

Figure 30:
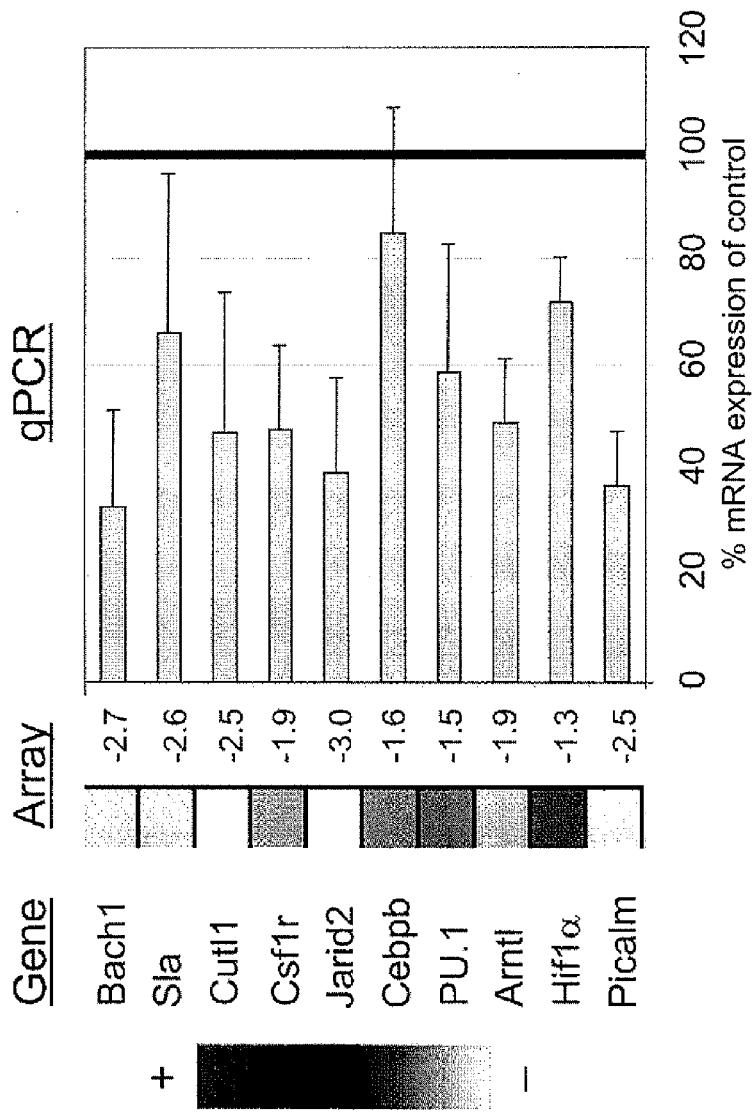
FIG. 30 is a bar graph showing the percent mRNA expression of the indicated genes in Raw 264.7 cells infected with MSCVpuro-155 or empty vector, as analyzed by micro-array and quantitative PCR. Numerical repression values for each mRNA are listed. For both the array and qPCR data, all values were normalized to L32 RNA levels, are displayed as the percent expression of control, and are the average of three independent experiments.

The microarray data and qPCR data are shown in FIG. 30. qPCR values were normalized to L32 mRNA levels and displayed as percent expression of control. Data are the average of three independent experiments. Bach1, Sla, Cutl1, Csflr, Jarid2, Cebpβ, PU.1, Arntl, Hif1α, and Picalm were down-regulated approximately 20%-70% in RAW 264.7 cells expressing miR-155 versus empty vector control. Western blotting was performed using standard protocols and the following antibodies from Santa Cruz Biotechnology: Cebpβ (C-19), PU.1 (T-21), Cutl1 (M-222), Picalm (C-18), and α Tubulin (AA12). Protein expression differences were determined using Scion Image Software. Western Blot confirmed repression of protein levels of Cepbβ, PU.1, Cutl1, and Picalm, in cells expressing miR-155. FIG. 31A is an image of an exemplary Western Blot.

Figure 31:
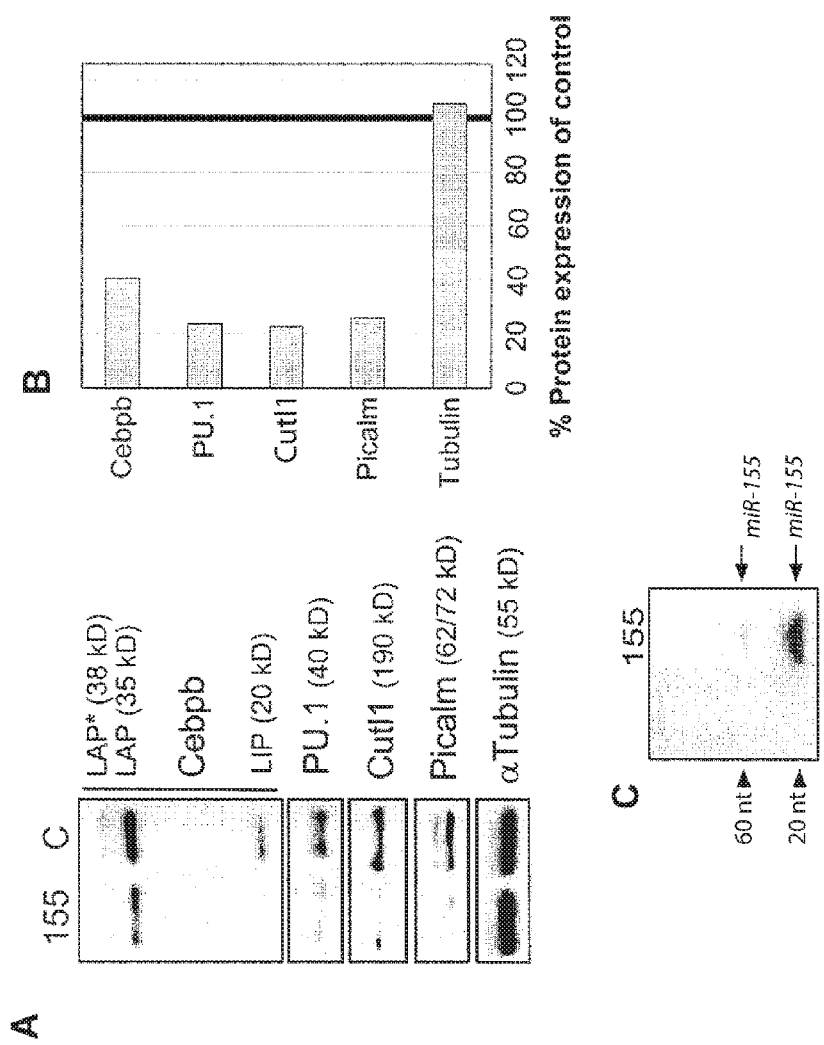
FIG. 31A is an image of a Western Blot to assay Cebpb, PU.1 cut 1, Picalm and α-Tubulin in Raw 264.7 cells stably expressing miR-155 (155) or empty vector (c).
FIG. 31B is a bar graph showing the % protein expression of control of Cebpb, PU.1, Cutl1, Picalm and Tubulin in Raw 264.7 cells stably expressing miR-155.
FIG. 31C is an image of a Northern Blot probing for miR-155, using RNA isolated from Raw 264.7 cells stably expressing miR-155 (155) or empty vector (−).
Figure 32:
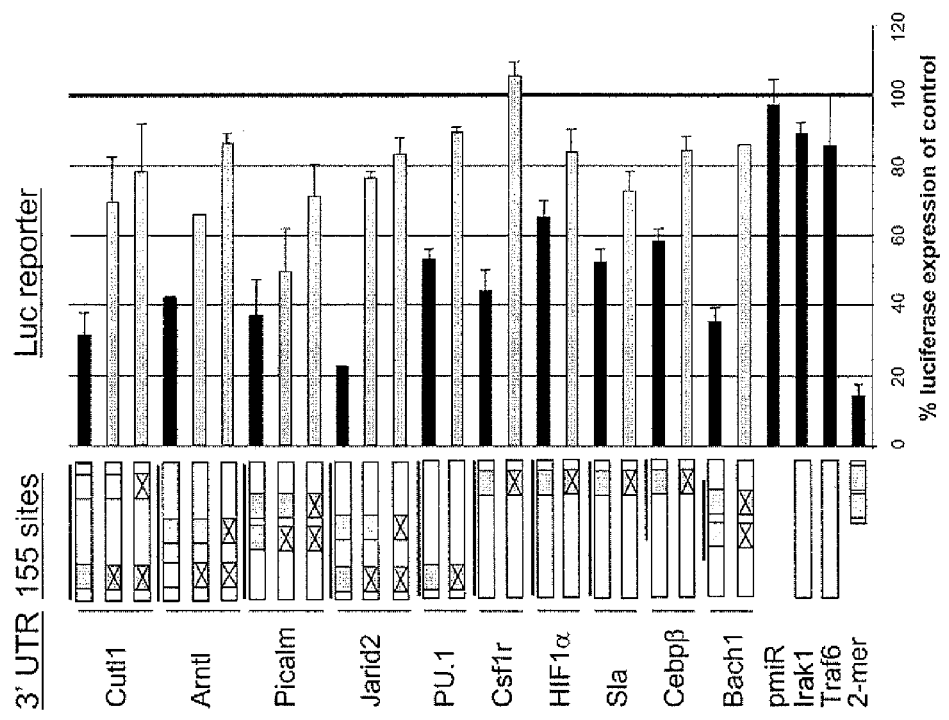
FIG. 32 shows a graphical depiction of the location of conserved miR-155 sites in 3' untranslated regions (3' UTRs) of the indicated genes. Grey boxes denote conserved 7 or 8-mer seeds, white boxes denote non-conserved 7-mer seeds, or conserved 6-mer seeds. The X's through boxes indicate mutations to seed regions. The line above the shown 3' UTR's indicates regions that were cloned downstream of from a luciferase reporter gene. Shown to the right is the % luciferase expression of control in 293T cells co-transformed with the indicated luciferase reporter constructs and a β-galactosidase expression plasmid, and an miR-155 expression vector or empty vector control. Data using wild-type 3'UTR's are in black. Data using mutant 3' UTR's are shown in gray. Data are a triplicate set representing three independent experiments.

To determine whether miR-155 could directly repress the identified mRNA targets through 3'UTR interactions, full length 3'UTRs, or in the case of Bach1 and Cebpβ the region of the UTR containing the miR-155 binding sites was cloned into pmiReport® (Ambion, Austin, Tex.), after amplification from a mouse macrophage cDNA library. Primer sequences for the cloning are listed in Table B. The Bach1 3' UTR region was amplified from a human B cell library. The 2-mer control insert consists of a tandem repeat of the complementary sequence to the mature mouse miR-155 sequences. Cloning of the TRAF6 and IRAK1 3" UTRs into pmiReport® was performed as described in Taganov, et al. (2006) *Proc. Nat. Acad. Sci. USA* 103:1241-12486, the contents of which are herein incorporated by reference in their entirety. $8\times10^4$ 293T cells were plated in DMEM media containing 5% FBS for 18 hours, followed by transfection of relevant plasmids using lipofectamine (Invitrogen, Carlsbad, Calif.), per manufacturer's instructions. Luciferase assays were preformed 48 hours after transfection using a dual luciferase kit (Promega, Madison, Wis.) according to the manufacturer's protocols. A β-galactosidase expression vector was co-transfected with the luciferase reporter constructs. β-galactosidase levels were assayed and sued to normalize the luciferase values. The data are shown in FIG. 31. Luciferase expression of the indicated constructs was repressed between 25-78%. TA rough correlation between the quantitative PCR results in RAW 264.7 and luciferase repression in 293T cells was observed.

TABLE B

PRIMERS USED FOR REPORTER CONSTRUCT CLONING

| Primer Name | SEQUENCE | SEQ ID NO: |
|---|---|---|
| Bach1 F | CCAGAGCTTAAATATAATTTGTAAAGC | 23 |
| Bach1 R | ACATTGAGAAGGCCAGTTCATAA | 24 |
| Sla F | GTAACTAGTTGACCTGGCTTGTACACAC | 25 |

TABLE B-continued

PRIMERS USED FOR REPORTER CONSTRUCT CLONING

| Primer Name | SEQUENCE | SEQ ID NO: |
|---|---|---|
| Sla R | GTTAAGCTTTAAATACATGATTTGGCAAAGTGTAA | 26 |
| Cutl1 F | TCAAGAGCTCGGCAAAATCGCCATAGGC | 27 |
| Cutl1 R | AGCTACGCGTCCCTTCCTAACAATCAGATTAATAAAAT | 28 |
| Csflr F | GTAACTAGTTCCTGCCGCTCTCTACGT | 29 |
| Csflr R | GTTAGCTTCTGGCTGTGTTAATGCTGTTAGTT | 30 |
| Jarid2 F | GTAACTAGTAGATGCCGAACCCATGGT | 31 |
| Jarid2 R | GTTAAGCTTATGAAGAGAAAAAATAGACAAGAGGA | 32 |
| Cebpβ F | GTAACTAGTTGCAATCCGGATCAAACG | 33 |
| Cebpβ R | GTTAAGCTTGGCTTTTAAACATTCTCCAAAAA | 34 |
| PU.1 F | GTAACTAGTCCGGCCATAGCATTAACC | 35 |
| PU.1 R | GTTAAGCTTGGGAGAATGACTGTCAATAATTTTACT | 36 |
| Arntl F | GTAACTAGTACACTACATTTGCTTTGGCAAC | 37 |
| Arntl R | AGCTACGCGTAGAACAAGGGAAACATTTATTAAAAT | 38 |
| Hifla F | TCAAGAGCTCCTGAGCGTTTCCTAATCTCATTC | 39 |
| Hifla R | AGCTACGCGTCCTGGTCCACAGAAGATGTTT | 40 |
| Picalm F | TCAAGAGCTCATGGAAGAGAATGGAATTACTCCA | 41 |
| Picalm R | GTTAAGCTTTGTTTTGTGGAAGCTGCATT | 42 |

To demonstrate a direct interaction between miR-155 and the 3" UTR's tested, site-directed mutagenesis of the reporter vectors was used to change specific nucleotides found within the miR-155 seed regions. See, Table C. The 2-mer control miR-155 construct was repressed approximately 80%. However, luciferase levels were relatively unaffected when the Traf6 or Irak1 3' UTR's were tested, consistent with their lack of miR-155 binding sites.

TABLE C

MIR-155 WT AND MUTANT SEED SEQUENCES

| miR-155 Seed | WT | SEQ ID NO: | Mutant | SEQ ID NO: |
|---|---|---|---|---|
| Bach1 1 | AGCATTAA | 43 | AGGTAAAA | 57 |
| Bach1 2 | AGCATTA | 44 | AGGTAAA | 58 |
| PU.1 | AGCATTAA | 45 | AGGTAAAA | 59 |
| Cutl1 1 | AGCATTAA | 46 | AGGTAAAA | 60 |
| Cutl1 2 | GCATTA | 47 | GCTAAA | 61 |
| Picalm 1 | GCATTAA | 48 | GGAGTGA | 62 |
| Picalm 2 | AGCATTA | 49 | AGCTAAA | 63 |
| Arntl 1 | GCATTAA | 50 | GCAATA | 64 |
| Arntl 2 | GCATTAA | 51 | AGCAAATA | 65 |
| Csflr | AGCATTAA | 52 | AGCAAAT | 66 |

TABLE C-continued

MIR-155 WT AND MUTANT SEED SEQUENCES

| miR-155 Seed | WT | SEQ ID NO: | Mutant | SEQ ID NO: |
|---|---|---|---|---|
| Sla | AGCATTA | 53 | GCAAATA | 67 |
| Jarid2 1 | AGCATTAA | 54 | ACGTAATA | 68 |
| Jarid2 2 | AGCATTAA | 55 | AGCAAATA | 69 |
| Hifla | AGCATTA | 56 | AGCAAAT | 70 |

The data presented above demonstrate that miR-155 can directly regulate several genes, including but not limited to Bach1, PU.1, Cutl1, Picalm, Arntl, Csflr, Sla, Jarid2, and HIfla, that are relevant to hematopoiesis and myeloproliferation.

Example 14

Diagnosis of Myeloproliferative Disorders

This example illustrates the diagnosis of a subject having, or suspected of having a myeloproliferative disorder. A subject suffering from, or at risk of developing a myeloproliferative disorder is identified. For example, a subject that exhibits symptoms of acute myeloid leukemia, or that has been identified as being at risk of developing acute myeloid leukemia is identified. For example, an individual exposed to a risk factor(s) associated with AML, e.g., carcinogens including but not limited to benzene, tobacco smoke, and ionizing radiation, or who has received chemotherapy to treat other cancers, or who has been diagnosed as having myelodysplasia, is identified. The subject can also exhibit one or more symptoms including fatigue, fever, recurrent infections, weight loss, night sweats, or bleeding.

A bone marrow sample is obtained from the subject. RNA is isolated from the bone marrow. The level of miR-155 (either mature or pre-miR-155) is measured, for example, by qPCR (as described in Example 12), or by microarray analysis (as described in Example 1, modified for a human array). Other methods known to those skilled in the art can be used to detect miR-155 levels. The miR-155 levels from the bone marrow of the subject are compared to miR-155 levels in a control. The subject is identified as having AML if the subject's miR-155 levels are significantly elevated (e.g., 2-fold, 3-fold, 4-fold, 5-fold, or more, or any number in between) compared to miR-155 levels in normal subjects.

Example 15

Treatment of Myeloproliferative Disorders

This example illustrates the treatment of a subject suffering from a myeloproliferative disorder, such as acute myeloid leukemia (AML).

A subject suffering from or at risk of developing a myeloid proliferative disease or disorder is identified. The subject is identified by any means known to those skilled in the art, including the methods described in Example 14 herein. The subject is administered an effective amount of an miR-155 antagonist, such as an miR-155 antisense compound. A typical daily dose for an miR-155 antagonist might range from about 0.01 µg/kg to about 1 mg/kg of patient body weight or more per day, depending on the factors mentioned above. Preferably the dose ranges from about 10 µg/kg/day to about 100 µg/kg/day. The appropriate dosage and treatment regimen can be readily determined by the skilled artisan based on a number of factors, including but not limited to the nature of the miR-155 antagonist, the route of administration, and the subject's disease state. AML treatment efficacy is evaluated by observing a delay or slowing of the disease progression, amelioration or palliation of the disease state or symptoms, and/or remission.

Example 16

Treatment or Modulation of Inflammation

This example illustrates the treatment of a subject suffering from inflammation, or inflammatory-related conditions, such as inflammation arising from a macrophage-induced inflammatory response, mediated through a Toll-like Receptor(s) (TLRs). The inflammation can arise as a result of activation of TLR2, TLR3, TLR4, TLR9, pathways, or the like, for example caused by cancer, viral infection, microbial infection or the like, as described herein.

A subject suffering from or at risk of developing a condition associated with TLR-mediated inflammation is identified. The subject is administered an effective amount of an miR-155 antagonist, such as an miR-155 antisense compound. A typical daily dose for an miR-155 antagonist might range from about 0.01 µg/kg to about 1 mg/kg of patient body weight or more per day, depending on the factors mentioned above. Preferably the dose ranges from about 10 µg/kg/day to about 100 µg/kg/day. The appropriate dosage and treatment regimen can be readily determined by the skilled artisan based on a number of factors, including but not limited to the nature of the miR-155 antagonist, the route of administration, and the subject's state. Efficacy is evaluated by observing a delay or slowing inflammatory progression.

Example 17

Modulation of miR-155 Target Gene Expression

This example illustrates the modulation of miR-155 target gene expression in a subject.

A target cell(s) is identified as being in need of modulation of miR-155 target gene expression. For example, a target cell(s) is identified by identifying a subject having, or at risk of developing a myeloproliferative disease such as AML, or as experiencing TLR-mediated inflammation. Cells such as hematopoietic cells, bone marrow cells, myeloid precursor cells, myeloid cells, macrophages, and the like of said subject are identified as target cells. Target cells are contacted with an miR-155 antagonist, such as an miR-155 antisense compound. The subject is provided daily dose of an miR-155 antagonist, which might range from about 0.01 µg/kg to about 1 mg/kg of subject body weight or more per day, depending on the factors mentioned above. Preferably the dose ranges from about 10 µg/kg/day to about 100 µg/kg/day. The appropriate dosage and treatment regimen can be readily determined by the skilled artisan based on a number of factors, including but not limited to the nature of the miR-155 antagonist, the route of administration, and the subject's disease state, or condition. Levels of miR-155 target genes such as Cutl1, Arntl, Picalm, Jarid2, PU.1, Csflr, HIF1α, Sla, Cepbβ, and Bach within the target cell(s) can be determined before and after administration of the miR-155 antagonist.

All patents and publications are herein incorporated by reference in their entireties to the same extent as if each individual publication was specifically and individually indicated to be incorporated by reference.

The invention illustratively described herein suitably can be practiced in the absence of nay element or elements, limitation or limitations that is not specifically disclosed herein. The terms and expression which have been employed are used as terms of description and not of limitation, and there is no intention that the use of such terms and expressions indicates the exclusion of equivalents of the features shown and described, or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

What is claimed is:

1. A method of modulating the expression of Bach1 gene in a subject having or suspected of suffering from inflammation or an inflammatory-related condition, comprising:
    administering to the subject an miR-155 antisense compound comprising a modified oligonucleotide consisting of 12 to 30 linked nucleosides in an amount effective to modulate the expression of Bach1 gene, wherein the nucleobase sequence of the modified oligonucleotides is complementary to a sequence at least 90% identical to mature microRNA-155 (SEQ ID NO: 73).

2. The method of claim 1, wherein the nucleobase sequence of the modified oligonucleotide has no more than two mismatches to the nucleobase sequence of mature miR-155 (SEQ ID NO: 73).

3. The method of claim 1, wherein the modified oligonucleotide comprises a sequence fully complementary to the sequence of mature miR-155 (SEQ ID NO: 73).

4. The method of claim 1, wherein the modified oligonucleotide comprises at least 15 contiguous nucleobases of SEQ ID NO: 74.

5. The method of claim 4, wherein the modified oligonucleotide comprises SEQ ID NO: 74.

6. The method of claim 1, wherein the modified oligonucleotide comprises at least one sugar-modified nucleoside.

7. The method of claim 6, wherein the sugar-modified nucleoside comprises a modified sugar selected from a bicyclic sugar moiety, a 2'-fluoro sugar, a 2'-O-methyl sugar, and a 2'-O-methoxyethyl sugar.

8. The method of claim 1, wherein the inflammation is inflammation arising from a macrophage-induced inflammatory response.

9. The method of claim 1, wherein the inflammation is mediated by a Toll-like receptor (TLR).

10. The method of claim 9, wherein said TLR is selected from the group consisting of TLR2, TLR3, TLR, 4 and TLR9.

11. The method of claim 1, wherein the inflammation or inflammatory-related condition is caused by cancer, viral infection or microbial infection.

12. The method of claim 1, wherein the inflammation or inflammatory-related condition is selected from sepsis, septic shock, neurodegeneration, neutrophilic alveolitis, asthma, hepatitis, inflammatory bowel disease, ischemia, glomerulonephritis, rheumatoid arthritis and Crohn's disease.

13. The method of claim 1, wherein the subject is human.

14. The method of claim 1, wherein administration comprises parenteral administration.

15. The method of claim 1, comprising administering at least one therapy in addition to the miR-155 antisense compound.

16. The method of claim 15, wherein the additional therapy comprises an immunosuppressant.

17. The method of claim 16, wherein the immunosuppressant is a corticosteroid.

18. The method of claim 15, wherein the additional therapy comprises a pharmaceutical agent that enhances the body's immune system.

19. The method of claim 18, wherein the pharmaceutical agent is selected from low-dose cyclophosphamide, thymostimulin, vitamins, nutritional supplements and vaccines.

20. The method of claim 1, wherein the modified oligonucleotide consists of 15 to 25 linked nucleosides.

* * * * *

SEQUENCE LISTING

<160> NUMBER OF SEQ ID NOS: 74

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
ttggcctctg actgactcct                                             20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
gcagggtgac tcttggactt                                             20

```
<210> SEQ ID NO 3
<211> LENGTH: 22
<212> TYPE: DNA
<213> ORGANISM: Artificial Sequence
<220> FEATURE:
<223> OTHER INFORMATION: oligonucleotide

<400> SEQUENCE: 3
tgagtgagag tgcggtattt gc                                              22

<210> SEQ ID NO 4
<211> LENGTH: 21
<212> TYPE: DNA
<213> ORGANISM: Artificial Sequence
<220> FEATURE:
<223> OTHER INFORMATION: oligonucleotide

<400> SEQUENCE: 4
gtcagtctgg cctacgattc t                                               21

<210> SEQ ID NO 5
<211> LENGTH: 22
<212> TYPE: DNA
<213> ORGANISM: Artificial Sequence
<220> FEATURE:
<223> OTHER INFORMATION: oligonucleotide

<400> SEQUENCE: 5
atggggaata gcatgaaatc ac                                              22

<210> SEQ ID NO 6
<211> LENGTH: 21
<212> TYPE: DNA
<213> ORGANISM: Artificial Sequence
<220> FEATURE:
<223> OTHER INFORMATION: oligonucleotide

<400> SEQUENCE: 6
ggagatgggt agtcagtcag c                                               21

<210> SEQ ID NO 7
<211> LENGTH: 22
<212> TYPE: DNA
<213> ORGANISM: Artificial Sequence
<220> FEATURE:
<223> OTHER INFORMATION: oligonucleotide

<400> SEQUENCE: 7
cgcagagaac tgttcattga gg                                              22

<210> SEQ ID NO 8
<211> LENGTH: 19
<212> TYPE: DNA
<213> ORGANISM: Artificial Sequence
<220> FEATURE:
<223> OTHER INFORMATION: oligonucleotide

<400> SEQUENCE: 8
gagctgaagg tgagtcgct                                                  19

<210> SEQ ID NO 9
<211> LENGTH: 19
<212> TYPE: DNA
<213> ORGANISM: Artificial Sequence
<220> FEATURE:
<223> OTHER INFORMATION: oligonucleotide
```

```
<400> SEQUENCE: 9
tgtcatgcag cctagtggc                                          19

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
cgggagattc agggtccaag                                         20

<210> SEQ ID NO 11
<211> LENGTH: 21
<212> TYPE: DNA
<213> ORGANISM: Artificial Sequence
<220> FEATURE:
<223> OTHER INFORMATION: oligonucleotide

<400> SEQUENCE: 11
gaaggcggta aatgggcttc t                                       21

<210> SEQ ID NO 12
<211> LENGTH: 22
<212> TYPE: DNA
<213> ORGANISM: Artificial Sequence
<220> FEATURE:
<223> OTHER INFORMATION: oligonucleotide

<400> SEQUENCE: 12
tcgttgctag tagaggacac tt                                      22

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
gacaagcaca gcgacgagta                                         20

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
agctgctcca ccttcttctg                                         20

<210> SEQ ID NO 15
<211> LENGTH: 22
<212> TYPE: DNA
<213> ORGANISM: Artificial Sequence
<220> FEATURE:
<223> OTHER INFORMATION: oligonucleotide

<400> SEQUENCE: 15
atgttacagg cgtgcaaaat gg                                      22

<210> SEQ ID NO 16
<211> LENGTH: 21
```

<212> TYPE: DNA
<213> ORGANISM: Artificial Sequence
<220> FEATURE:
<223> OTHER INFORMATION: oligonucleotide

<400> SEQUENCE: 16
tgatcgctat ggctttctcc a                                              21

<210> SEQ ID NO 17
<211> LENGTH: 23
<212> TYPE: DNA
<213> ORGANISM: Artificial Sequence
<220> FEATURE:
<223> OTHER INFORMATION: oligonucleotide

<400> SEQUENCE: 17
accacaggaa cttctaggta cat                                            23

<210> SEQ ID NO 18
<211> LENGTH: 23
<212> TYPE: DNA
<213> ORGANISM: Artificial Sequence
<220> FEATURE:
<223> OTHER INFORMATION: oligonucleotide

<400> SEQUENCE: 18
ggacattggc taaaacaaca gtg                                            23

<210> SEQ ID NO 19
<211> LENGTH: 22
<212> TYPE: DNA
<213> ORGANISM: Artificial Sequence
<220> FEATURE:
<223> OTHER INFORMATION: oligonucleotide

<400> SEQUENCE: 19
accttcatcg gaaactccaa ag                                             22

<210> SEQ ID NO 20
<211> LENGTH: 21
<212> TYPE: DNA
<213> ORGANISM: Artificial Sequence
<220> FEATURE:
<223> OTHER INFORMATION: oligonucleotide

<400> SEQUENCE: 20
actgttaggc tcaggtgaac t                                              21

<210> SEQ ID NO 21
<211> LENGTH: 19
<212> TYPE: DNA
<213> ORGANISM: Artificial Sequence
<220> FEATURE:
<223> OTHER INFORMATION: oligonucleotide

<400> SEQUENCE: 21
gtctgtccac gccatgtcg                                                 19

<210> SEQ ID NO 22
<211> LENGTH: 21
<212> TYPE: DNA
<213> ORGANISM: Artificial Sequence
<220> FEATURE:
<223> OTHER INFORMATION: oligonucleotide

<400> SEQUENCE: 22
tagcagagaa aggatctccc c    21

<210> SEQ ID NO 23
<211> LENGTH: 27
<212> TYPE: DNA
<213> ORGANISM: Artificial Sequence
<220> FEATURE:
<223> OTHER INFORMATION: oligonucleotide

<400> SEQUENCE: 23
ccagagctta aatataattt gtaaagc    27

<210> SEQ ID NO 24
<211> LENGTH: 23
<212> TYPE: DNA
<213> ORGANISM: Artificial Sequence
<220> FEATURE:
<223> OTHER INFORMATION: oligonucleotide

<400> SEQUENCE: 24
acattgagaa ggccagttca taa    23

<210> SEQ ID NO 25
<211> LENGTH: 30
<212> TYPE: DNA
<213> ORGANISM: Artificial Sequence
<220> FEATURE:
<223> OTHER INFORMATION: oligonucleotide

<400> SEQUENCE: 25
gtaactagtt gacctggctt gtacacacac    30

<210> SEQ ID NO 26
<211> LENGTH: 35
<212> TYPE: DNA
<213> ORGANISM: Artificial Sequence
<220> FEATURE:
<223> OTHER INFORMATION: oligonucleotide

<400> SEQUENCE: 26
gttaagcttt aaatacatga tttggcaaag tgtaa    35

<210> SEQ ID NO 27
<211> LENGTH: 28
<212> TYPE: DNA
<213> ORGANISM: Artificial Sequence
<220> FEATURE:
<223> OTHER INFORMATION: oligonucleotide

<400> SEQUENCE: 27
tcaagagctc ggcaaaatcg ccataggc    28

<210> SEQ ID NO 28
<211> LENGTH: 38
<212> TYPE: DNA
<213> ORGANISM: Artificial Sequence
<220> FEATURE:
<223> OTHER INFORMATION: oligonucleotide

<400> SEQUENCE: 28
agctacgcgt cccttcctaa caatcagatt aataaaat    38

<210> SEQ ID NO 29
<211> LENGTH: 27
<212> TYPE: DNA
<213> ORGANISM: Artificial Sequence
<220> FEATURE:
<223> OTHER INFORMATION: oligonucleotide

<400> SEQUENCE: 29
gtaactagtt cctgccgctc tctacgt                                    27

<210> SEQ ID NO 30
<211> LENGTH: 32
<212> TYPE: DNA
<213> ORGANISM: Artificial Sequence
<220> FEATURE:
<223> OTHER INFORMATION: oligonucleotide

<400> SEQUENCE: 30
gttagcttct ggctgtgtta atgctgttag tt                              32

<210> SEQ ID NO 31
<211> LENGTH: 27
<212> TYPE: DNA
<213> ORGANISM: Artificial Sequence
<220> FEATURE:
<223> OTHER INFORMATION: oligonucleotide

<400> SEQUENCE: 31
gtaactagta gatgccgaac ccatggt                                    27

<210> SEQ ID NO 32
<211> LENGTH: 35
<212> TYPE: DNA
<213> ORGANISM: Artificial Sequence
<220> FEATURE:
<223> OTHER INFORMATION: oligonucleotide

<400> SEQUENCE: 32
gttaagctta tgaagagaaa aaatagacaa gagga                           35

<210> SEQ ID NO 33
<211> LENGTH: 27
<212> TYPE: DNA
<213> ORGANISM: Artificial Sequence
<220> FEATURE:
<223> OTHER INFORMATION: oligonucleotide

<400> SEQUENCE: 33
gtaactagtt gcaatccgga tcaaacg                                    27

<210> SEQ ID NO 34
<211> LENGTH: 32
<212> TYPE: DNA
<213> ORGANISM: Artificial Sequence
<220> FEATURE:
<223> OTHER INFORMATION: oligonucleotide

<400> SEQUENCE: 34
gttaagcttg gcttttaaac attctccaaa aa                              32

<210> SEQ ID NO 35
<211> LENGTH: 27
<212> TYPE: DNA
<213> ORGANISM: Artificial Sequence
<220> FEATURE:
<223> OTHER INFORMATION: oligonucleotide

<400> SEQUENCE: 35
gtaactagtc cggccatagc attaacc                                    27

<210> SEQ ID NO 36
<211> LENGTH: 36
<212> TYPE: DNA
<213> ORGANISM: Artificial Sequence
<220> FEATURE:
<223> OTHER INFORMATION: oligonucleotide

<400> SEQUENCE: 36
gttaagcttg ggagaatgac tgtcaataat tttact                          36

<210> SEQ ID NO 37
<211> LENGTH: 31
<212> TYPE: DNA
<213> ORGANISM: Artificial Sequence
<220> FEATURE:
<223> OTHER INFORMATION: oligonucleotide

<400> SEQUENCE: 37
gtaactagta cactacattt gctttggcaa c                               31

<210> SEQ ID NO 38
<211> LENGTH: 37
<212> TYPE: DNA
<213> ORGANISM: Artificial Sequence
<220> FEATURE:
<223> OTHER INFORMATION: oligonucleotide

<400> SEQUENCE: 38
agctacgcgt agaacaaggg aaacatttat taaaaat                         37

<210> SEQ ID NO 39
<211> LENGTH: 33
<212> TYPE: DNA
<213> ORGANISM: Artificial Sequence
<220> FEATURE:
<223> OTHER INFORMATION: oligonucleotide

<400> SEQUENCE: 39
tcaagagctc ctgagcgttt cctaatctca ttc                             33

<210> SEQ ID NO 40
<211> LENGTH: 31
<212> TYPE: DNA
<213> ORGANISM: Artificial Sequence
<220> FEATURE:
<223> OTHER INFORMATION: oligonucleotide

<400> SEQUENCE: 40
agctacgcgt cctggtccac agaagatgtt t                               31

<210> SEQ ID NO 41
<211> LENGTH: 34
<212> TYPE: DNA
<213> ORGANISM: Artificial Sequence
<220> FEATURE:
<223> OTHER INFORMATION: oligonucleotide

<400> SEQUENCE: 41
tcaagagctc atggaagaga atggaattac tcca                            34

<210> SEQ ID NO 42
<211> LENGTH: 29
<212> TYPE: DNA
<213> ORGANISM: Artificial Sequence
<220> FEATURE:
<223> OTHER INFORMATION: oligonucleotide

```
<400> SEQUENCE: 42
gttaagcttt gttttgtgga agctgcatt                                29

<210> SEQ ID NO 43
<211> LENGTH: 8
<212> TYPE: DNA
<213> ORGANISM: Artificial Sequence
<220> FEATURE:
<223> OTHER INFORMATION: oligonucleotide

<400> SEQUENCE: 43 agcattaa                                                        8

<210> SEQ ID NO 44
<211> LENGTH: 7
<212> TYPE: DNA
<213> ORGANISM: Artificial Sequence
<220> FEATURE:
<223> OTHER INFORMATION: oligonucleotide

<400> SEQUENCE: 44 agcatta                                                         7

<210> SEQ ID NO 45
<211> LENGTH: 8
<212> TYPE: DNA
<213> ORGANISM: Artificial Sequence
<220> FEATURE:
<223> OTHER INFORMATION: oligonucleotide

<400> SEQUENCE: 45 agcattaa                                                        8

<210> SEQ ID NO 46
<211> LENGTH: 8
<212> TYPE: DNA
<213> ORGANISM: Artificial Sequence
<220> FEATURE:
<223> OTHER INFORMATION: oligonucleotide

<400> SEQUENCE: 46 agcattaa                                                        8

<210> SEQ ID NO 47
<211> LENGTH: 6
<212> TYPE: DNA
<213> ORGANISM: Artificial Sequence
<220> FEATURE:
<223> OTHER INFORMATION: oligonucleotide

<400> SEQUENCE: 47 gcatta                                                          6

<210> SEQ ID NO 48
<211> LENGTH: 7
<212> TYPE: DNA
<213> ORGANISM: Artificial Sequence
<220> FEATURE:
<223> OTHER INFORMATION: oligonucleotide

<400> SEQUENCE: 48 gcattaa                                                         7

<210> SEQ ID NO 49
```

```
<211> LENGTH: 7
<212> TYPE: DNA
<213> ORGANISM: Artificial Sequence
<220> FEATURE:
<223> OTHER INFORMATION: oligonucleotide

<400> SEQUENCE: 49 agcatta                                                                  7

<210> SEQ ID NO 50
<211> LENGTH: 7
<212> TYPE: DNA
<213> ORGANISM: Artificial Sequence
<220> FEATURE:
<223> OTHER INFORMATION: oligonucleotide

<400> SEQUENCE: 50 gcattaa                                                                  7

<210> SEQ ID NO 51
<211> LENGTH: 7
<212> TYPE: DNA
<213> ORGANISM: Artificial Sequence
<220> FEATURE:
<223> OTHER INFORMATION: oligonucleotide

<400> SEQUENCE: 51 gcattaa                                                                  7

<210> SEQ ID NO 52
<211> LENGTH: 8
<212> TYPE: DNA
<213> ORGANISM: Artificial Sequence
<220> FEATURE:
<223> OTHER INFORMATION: oligonucleotide

<400> SEQUENCE: 52 agcattaa                                                                 8

<210> SEQ ID NO 53
<211> LENGTH: 7
<212> TYPE: DNA
<213> ORGANISM: Artificial Sequence
<220> FEATURE:
<223> OTHER INFORMATION: oligonucleotide

<400> SEQUENCE: 53 agcatta                                                                  7

<210> SEQ ID NO 54
<211> LENGTH: 8
<212> TYPE: DNA
<213> ORGANISM: Artificial Sequence
<220> FEATURE:
<223> OTHER INFORMATION: oligonucleotide

<400> SEQUENCE: 54 agcattaa                                                                 8

<210> SEQ ID NO 55
<211> LENGTH: 8
<212> TYPE: DNA
<213> ORGANISM: Artificial Sequence
<220> FEATURE:
<223> OTHER INFORMATION: oligonucleotide

<400> SEQUENCE: 55
```

```
agcattaa                                                    8

<210> SEQ ID NO 56
<211> LENGTH: 7
<212> TYPE: DNA
<213> ORGANISM: Artificial Sequence
<220> FEATURE:
<223> OTHER INFORMATION: oligonucleotide

<400> SEQUENCE: 56 agcatta                                                     7

<210> SEQ ID NO 57
<211> LENGTH: 7
<212> TYPE: DNA
<213> ORGANISM: Artificial Sequence
<220> FEATURE:
<223> OTHER INFORMATION: oligonucleotide

<400> SEQUENCE: 57 aggtaaa                                                     7

<210> SEQ ID NO 58
<211> LENGTH: 7
<212> TYPE: DNA
<213> ORGANISM: Artificial Sequence
<220> FEATURE:
<223> OTHER INFORMATION: oligonucleotide

<400> SEQUENCE: 58 aggtaaa                                                     7

<210> SEQ ID NO 59
<211> LENGTH: 8
<212> TYPE: DNA
<213> ORGANISM: Artificial Sequence
<220> FEATURE:
<223> OTHER INFORMATION: oligonucleotide

<400> SEQUENCE: 59 aggtaaaa                                                    8

<210> SEQ ID NO 60
<211> LENGTH: 8
<212> TYPE: DNA
<213> ORGANISM: Artificial Sequence
<220> FEATURE:
<223> OTHER INFORMATION: oligonucleotide

<400> SEQUENCE: 60 aggtaaaa                                                    8

<210> SEQ ID NO 61
<211> LENGTH: 6
<212> TYPE: DNA
<213> ORGANISM: Artificial Sequence
<220> FEATURE:
<223> OTHER INFORMATION: oligonucleotide

<400> SEQUENCE: 61 gctaaa                                                      6

<210> SEQ ID NO 62
<211> LENGTH: 7
<212> TYPE: DNA
```

```
<213> ORGANISM: Artificial Sequence
<220> FEATURE:
<223> OTHER INFORMATION: oligonucleotide

<400> SEQUENCE: 62 ggagtga                                                                 7

<210> SEQ ID NO 63
<211> LENGTH: 7
<212> TYPE: DNA
<213> ORGANISM: Artificial Sequence
<220> FEATURE:
<223> OTHER INFORMATION: oligonucleotide

<400> SEQUENCE: 63 agctaaa                                                                 7

<210> SEQ ID NO 64
<211> LENGTH: 6
<212> TYPE: DNA
<213> ORGANISM: Artificial Sequence
<220> FEATURE:
<223> OTHER INFORMATION: oligonucleotide

<400> SEQUENCE: 64 gcaata                                                                  6

<210> SEQ ID NO 65
<211> LENGTH: 8
<212> TYPE: DNA
<213> ORGANISM: Artificial Sequence
<220> FEATURE:
<223> OTHER INFORMATION: oligonucleotide

<400> SEQUENCE: 65 agcaaata                                                                8

<210> SEQ ID NO 66
<211> LENGTH: 7
<212> TYPE: DNA
<213> ORGANISM: Artificial Sequence
<220> FEATURE:
<223> OTHER INFORMATION: oligonucleotide

<400> SEQUENCE: 66 agcaaat                                                                 7

<210> SEQ ID NO 67
<211> LENGTH: 7
<212> TYPE: DNA
<213> ORGANISM: Artificial Sequence
<220> FEATURE:
<223> OTHER INFORMATION: oligonucleotide

<400> SEQUENCE: 67 gcaaata                                                                 7

<210> SEQ ID NO 68
<211> LENGTH: 8
<212> TYPE: DNA
<213> ORGANISM: Artificial Sequence
<220> FEATURE:
<223> OTHER INFORMATION: oligonucleotide

<400> SEQUENCE: 68 acgtaata                                                                8
```

<210> SEQ ID NO 69
<211> LENGTH: 8
<212> TYPE: DNA
<213> ORGANISM: Artificial Sequence
<220> FEATURE:
<223> OTHER INFORMATION: oligonucleotide

<400> SEQUENCE: 69 agcaaata                                                                      8

<210> SEQ ID NO 70
<211> LENGTH: 7
<212> TYPE: DNA
<213> ORGANISM: Artificial Sequence
<220> FEATURE:
<223> OTHER INFORMATION: oligonucleotide

<400> SEQUENCE: 70 agcaaat                                                                       7

<210> SEQ ID NO 71
<211> LENGTH: 1487
<212> TYPE: DNA
<213> ORGANISM: Homo sapien

<400> SEQUENCE: 71

```
cgcggcttcc tgtgcgcggc cgagcccggg cccagcgccg cctgcagcct cgggaaggga      60
gcggatagcg gagccccgag ccgcccgcag agcaagcgcg gggaaccaag agacgctcc      120 tggcactgca gataacttgt ctgcatttca agaacaacct accagagacc ttacctgtca     180
ccttggctct cccacccaat ggagatggct ctaatggtgg cacaaaccag gaaggggaaa     240
tctgtggttt aaattcttta tgcctcatcc tctgagtgct gaaggcttgc tgtaggctgt     300
atgctgttaa tgctaatcgt gatagggggtt tttgcctcca actgactcct acatattagc    360
attaacagtg tatgatgcct gttactagca ttcacatgga acaaattgct gccgtgggag     420
gatgacaaag aagcatgagt caccctgctg gataaactta gacttcaggc tttatcattt     480
ttcaatctgt taatcataat ctggtcactg ggatgttcaa ccttaaacta agttttgaaa     540
gtaaggttat ttaaaagatt tatcagtagt atcctaaatg caaacatttt catttaaatg     600
tcaagcccat gtttgttttt atcattaaca gaaaatatat tcatgtcatt cttaattgca     660
ggttttggct tgttcattat aatgttcata acacctttg attcaactgt tagaaatgtg      720
ggctaaacac aaatttctat aatatttttg tagttaaaaa ttagaaggac tactaacctc     780
cagttatatc atggattgtc tggcaacgtt ttttaaaaga tttagaaact ggtactttcc     840
cccaggtaac gattttctgt tcaggcaact tcagtttaaa attaatactt ttatttgact     900
cttaaaggga aactgaaagg ctatgaagct gaatttttt aatgaaatat ttttaacagt      960
tagcagggta ataacatct gacagctaat gagatatttt tccatacaa gataaaaaga     1020 tttaatcaaa aatttcatat ttgaaatgaa gtcccaaatc taggttcaag ttcaatagct    1080
tagccacata atacggttgt gcgagcagag aatctacctt tccacttcta agcctgtttc    1140
ttcctccata aaatgtgggat aatactttac aaggttgttg tgaggcttag atgagataga   1200
gaattattcc ataagataat caagtgctac attaatgtta tagttagatt aatccaagaa    1260
ctagtcaccc tactttatta gagaagagaa aagctaatga tttgatttgc agaatattta    1320
aggtttggat ttctatgcag tttttctaaa taaccatcac ttacaaatat gtaaccaaac    1380
```

```
gtaattgtta gtatatttaa tgtaaacttg ttttaacaac tcttctcaac attttgtcca    1440
ggttattcac tgtaaccaaa taaatctcat gagtctttag ttgattt                 1487

<210> SEQ ID NO 72
<211> LENGTH: 61
<212> TYPE: DNA
<213> ORGANISM: Homo sapien

<400> SEQUENCE: 72
uuaaugcuaa ucgugauagg gguuuuugcc uccaacugac uccuacauau uagcauuaac    60
a                                                                   61

<210> SEQ ID NO 73
<211> LENGTH: 22
<212> TYPE: DNA
<213> ORGANISM: Homo sapien

<400> SEQUENCE: 73
uuaaugcuaa ucgugauagg gg                                            22

<210> SEQ ID NO 74
<211> LENGTH: 22
<212> TYPE: DNA
<213> ORGANISM: oArtificial Sequence
<220> FEATURE:
<223> OTHER INFORMATION: oligonucleotide

<400> SEQUENCE: 74
ccccuaucac gauuagcauu aa                                            22
```